US012667717B2

(12) United States Patent (10) Patent No.: US 12,667,717 B2
Moss et al. (45) Date of Patent: Jun. 30, 2026

(54) ELECTRICAL APPLICATORS FOR APPLYING ENERGY TO TISSUE SURFACES OR REGIONS SUPERFICIAL TO THE SURFACE

(71) Applicant: Pulse Biosciences, Inc., Hayward, CA (US)

(72) Inventors: Kevin L. Moss, Lathrop, CA (US); David J. Danitz, San Jose, CA (US); Richard J. Connolly, Riverview, FL (US); Katherine P. Weilbacher, Miami, FL (US); Cameron D. Hinman, Thurmond, NC (US)

(73) Assignee: Pulse Biosciences, Inc., Hayward, CA (US)

(*) Notice: Subject to any disclaimer, the term of this patent is extended or adjusted under 35 U.S.C. 154(b) by 137 days.

(21) Appl. No.: 18/682,890

(22) PCT Filed: Aug. 8, 2022

(86) PCT No.: PCT/US2022/074666
§ 371 (c)(1),
(2) Date: Feb. 9, 2024

(87) PCT Pub. No.: WO2023/019108
PCT Pub. Date: Feb. 16, 2023

(65) Prior Publication Data
US 2024/0342465 A1      Oct. 17, 2024

Related U.S. Application Data

(60) Provisional application No. 63/231,698, filed on Aug. 10, 2021.

(51) Int. Cl.
| | | |
|---|---|---|
| A61N 1/04 | (2006.01) | |
| A61N 1/05 | (2006.01) | |
| A61N 1/32 | (2006.01) | |

(52) U.S. Cl.
CPC ......... *A61N 1/0476* (2013.01); *A61N 1/0502* (2013.01); *A61N 1/328* (2013.01)

(58) Field of Classification Search
None
See application file for complete search history.

(56) References Cited

U.S. PATENT DOCUMENTS

| | | | |
|---|---|---|---|
| 3,267,364 A | 8/1966 | Page et al. | |
| 5,449,378 A | 9/1995 | Schouenborg | |

(Continued)

FOREIGN PATENT DOCUMENTS

| | | |
|---|---|---|
| KR | 20130014211 A | 2/2013 |
| WO | WO02/067797 A2 | 9/2002 |

(Continued)

OTHER PUBLICATIONS

International Search Report and Written Opinion mailed Jan. 10, 2023 for PCT/US2022/074666; 21 pages.

*Primary Examiner* — Carl H Layno
*Assistant Examiner* — Bryan McAllister Lee
(74) *Attorney, Agent, or Firm* — Shay Glenn LLP

(57)                ABSTRACT

Treatment applicators and methods including treatment applicators for delivering electrical energy to a target tissue that are configured to reduce or eliminate arcing as well as provide enhance targeting to tissue surfaces or regions just below the surface of the tissue.

34 Claims, 29 Drawing Sheets

(56)                References Cited

U.S. PATENT DOCUMENTS

| | | | |
|---|---|---|---|
| 6,326,177 | B1 | 12/2001 | Schoenbach et al. |
| 6,352,534 | B1 | 3/2002 | Paddock et al. |
| 6,866,626 | B2 | 3/2005 | Long et al. |
| 6,964,643 | B2 | 11/2005 | Hovland et al. |
| 7,060,054 | B2 | 6/2006 | Nissels |
| 7,278,991 | B2 | 10/2007 | Morris et al. |
| 7,399,304 | B2 | 7/2008 | Gambale et al. |
| 7,422,586 | B2 | 9/2008 | Morris et al. |
| 7,618,429 | B2 | 11/2009 | Mullholland |
| 8,000,813 | B2 | 8/2011 | Schoenbach et al. |
| 8,048,089 | B2 | 11/2011 | Ignon et al. |
| 8,273,080 | B2 | 9/2012 | Mehta |
| 8,401,668 | B2 | 3/2013 | Deem et al. |
| 8,480,596 | B2 | 7/2013 | Jacobs |
| 8,512,334 | B2 | 8/2013 | Nuccitelli et al. |
| 8,518,069 | B2 | 8/2013 | Clark, III et al. |
| 8,696,545 | B2 | 4/2014 | Nicoson et al. |
| 8,822,222 | B2 | 9/2014 | Beebe et al. |
| 8,920,452 | B2 | 12/2014 | Clark, III et al. |
| 9,050,133 | B1 | 6/2015 | Boone, III et al. |
| 9,101,764 | B2 | 8/2015 | Nuccitelli et al. |
| 9,724,155 | B2 | 8/2017 | Nuccitelli et al. |
| 10,271,866 | B2 | 4/2019 | Clark, III et al. |
| 10,357,641 | B2 | 7/2019 | Ignon et al. |
| 10,638,963 | B2 | 5/2020 | Beyerlein et al. |
| 10,850,095 | B2 | 12/2020 | Ebbers et al. |
| 10,857,347 | B2 | 12/2020 | Danitz et al. |
| 10,918,859 | B2 | 2/2021 | Kang |
| 11,167,125 | B2 | 11/2021 | Moss et al. |
| 11,324,534 | B2 | 5/2022 | Ginggen et al. |
| 11,577,071 | B2 | 2/2023 | Hinman et al. |
| 2005/0124975 | A1 | 6/2005 | Law |
| 2007/0106143 | A1 | 5/2007 | Flaherty |
| 2007/0142885 | A1 | 6/2007 | Hantash et al. |
| 2008/0269851 | A1 | 10/2008 | Deem et al. |
| 2009/0093864 | A1 | 4/2009 | Anderson |
| 2009/0112205 | A1 | 4/2009 | McGill et al. |
| 2009/0177171 | A1 | 7/2009 | Ignon et al. |
| 2009/0192442 | A1 | 7/2009 | Ignon et al. |
| 2009/0198189 | A1 | 8/2009 | Simons et al. |
| 2010/0010484 | A1 | 1/2010 | Mehta et al. |
| 2010/0038971 | A1 | 2/2010 | Sanders et al. |
| 2010/0262135 | A1 | 10/2010 | Berube |
| 2011/0028941 | A1 | 2/2011 | Nagano et al. |
| 2011/0092973 | A1 | 4/2011 | Nuccitelli et al. |
| 2012/0158100 | A1 | 6/2012 | Schomacker |
| 2013/0345616 | A1 | 12/2013 | Chang |
| 2014/0343481 | A1 | 11/2014 | Ignon |
| 2014/0364797 | A1 | 12/2014 | Schoenbach et al. |
| 2015/0201991 | A1 | 7/2015 | Zemlin |
| 2017/0245928 | A1 | 8/2017 | Xiao et al. |
| 2018/0078755 | A1 | 3/2018 | Kreis et al. |
| 2018/0140317 | A1 | 5/2018 | Richardson et al. |
| 2018/0271589 | A1 | 9/2018 | Lei et al. |
| 2018/0303515 | A1 | 10/2018 | Shadduck et al. |
| 2019/0217080 | A1* | 7/2019 | Moss .................. A61N 1/0502 |
| 2021/0290941 | A1 | 9/2021 | Fischer et al. |
| 2024/0164833 | A1 | 5/2024 | Turovskiy et al. |

FOREIGN PATENT DOCUMENTS

| | | |
|---|---|---|
| WO | WO2011/071482 A1 | 6/2011 |
| WO | WO2011/163264 A2 | 12/2011 |
| WO | WO2014/096275 A1 | 6/2014 |
| WO | WO2021/247500 A1 | 12/2021 |
| WO | WO2022/104158 A2 | 5/2022 |
| WO | WO2022/271469 A1 | 12/2022 |
| WO | WO2023/019108 A1 | 2/2023 |

* cited by examiner

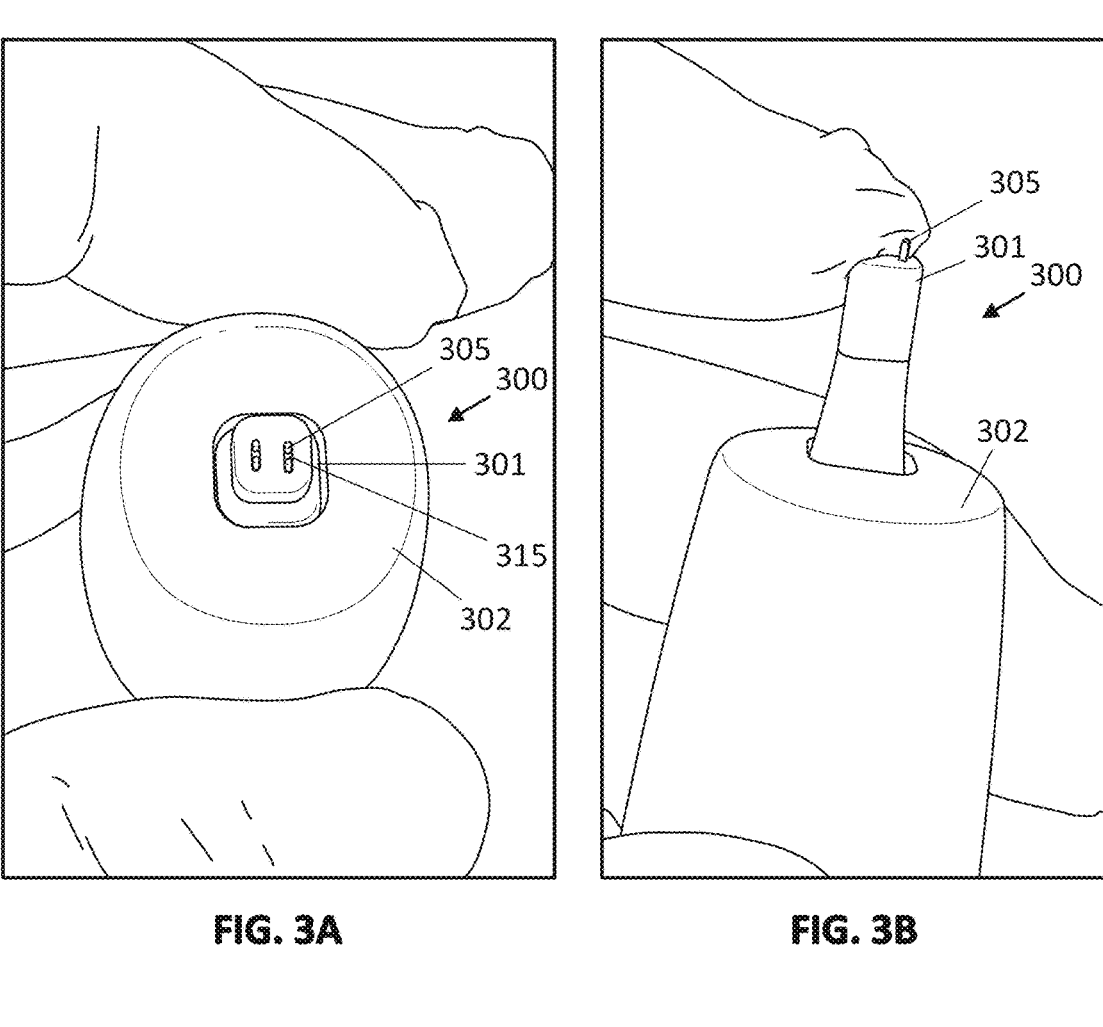
FIG. 3A                                    FIG. 3B
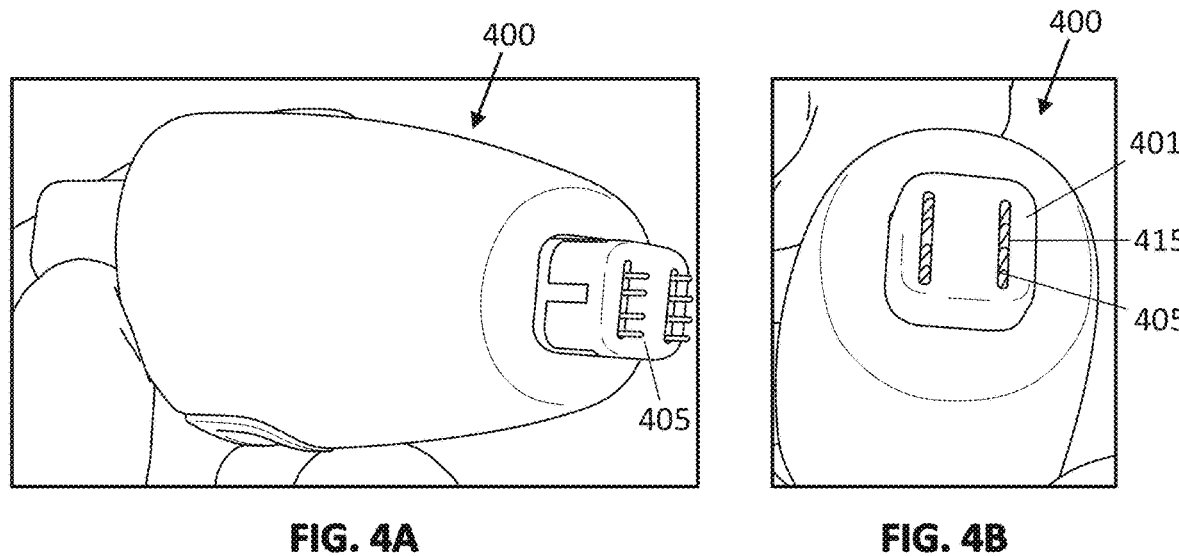
FIG. 4A                                    FIG. 4B 600
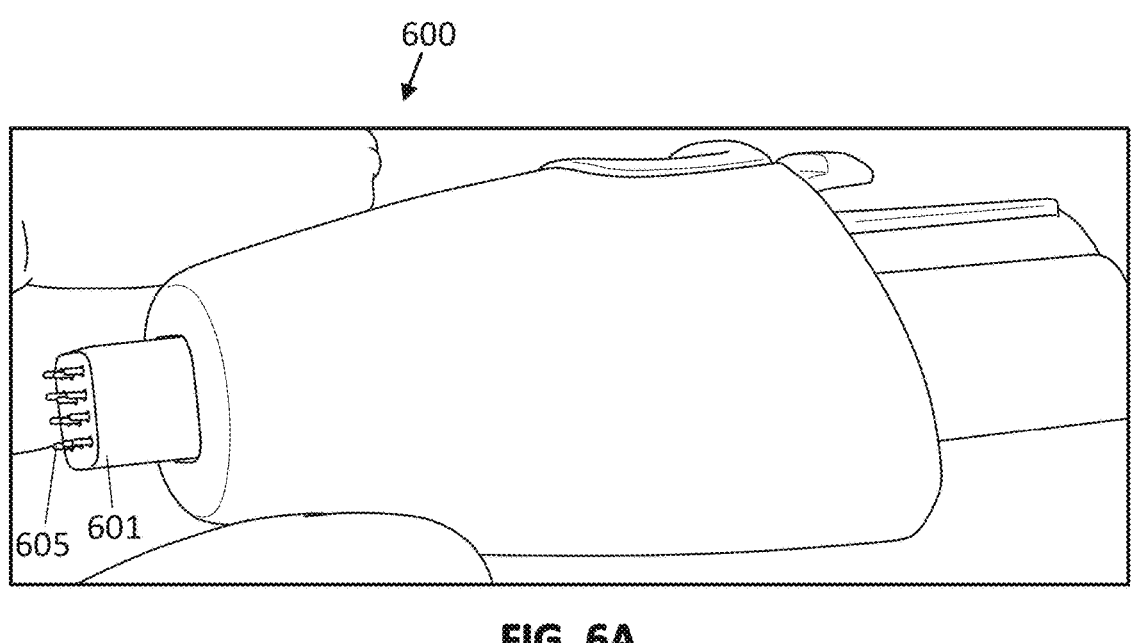
FIG. 6A
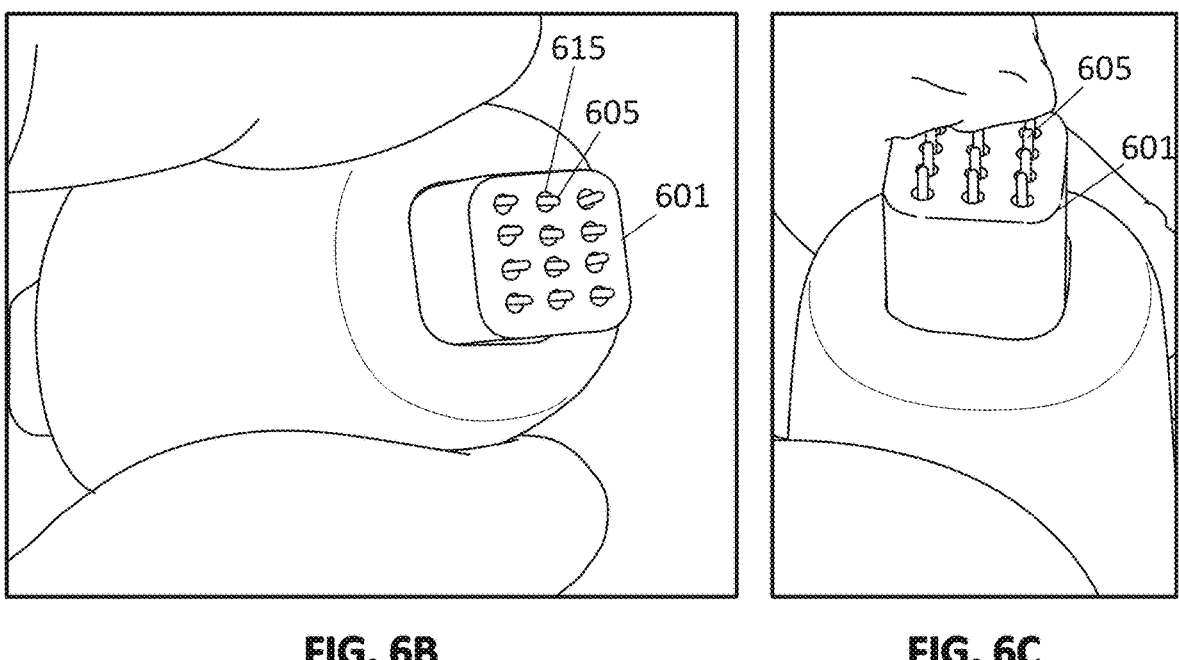
FIG. 6B                    FIG. 6C

700
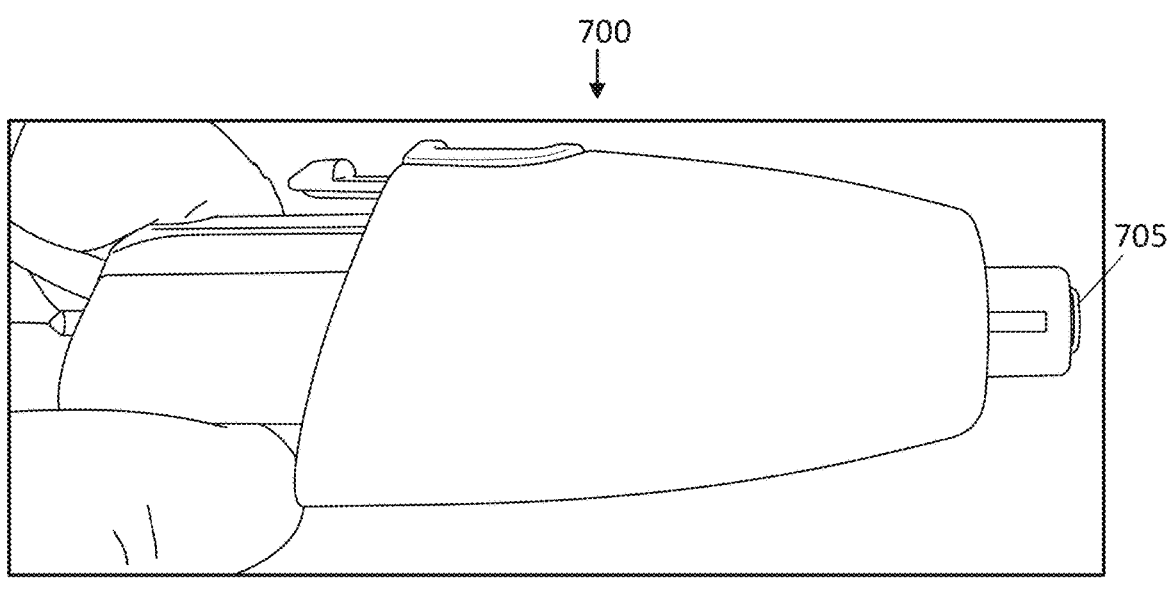
FIG. 7A
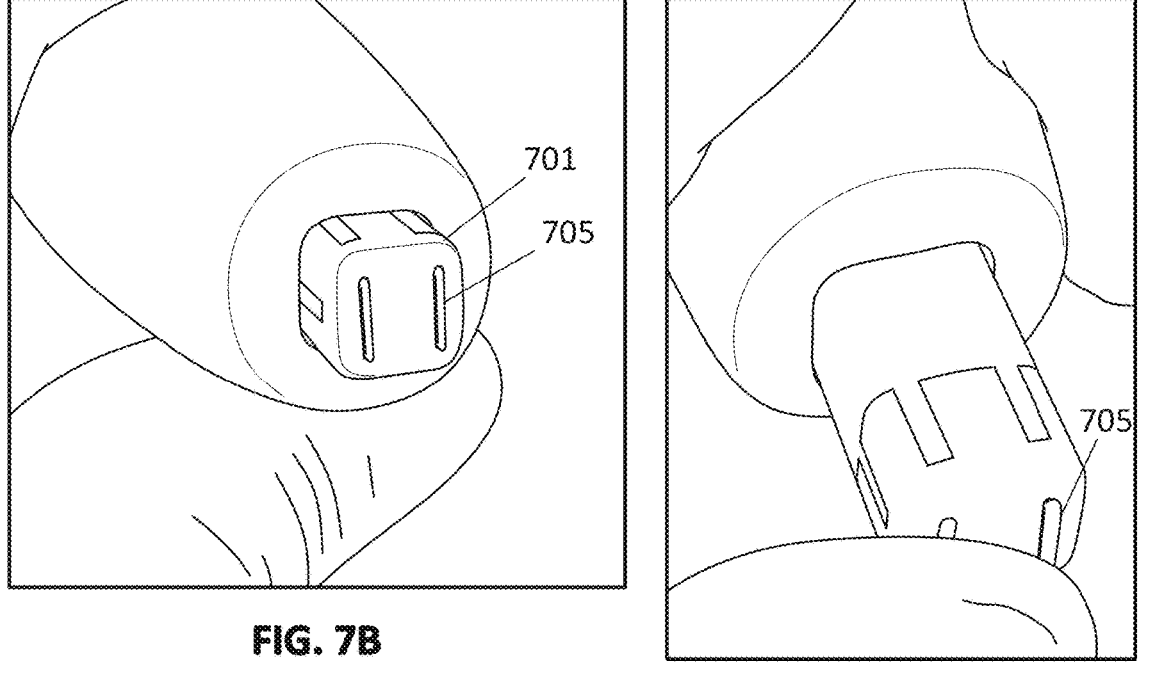
701
705
FIG. 7B
705
FIG. 7C

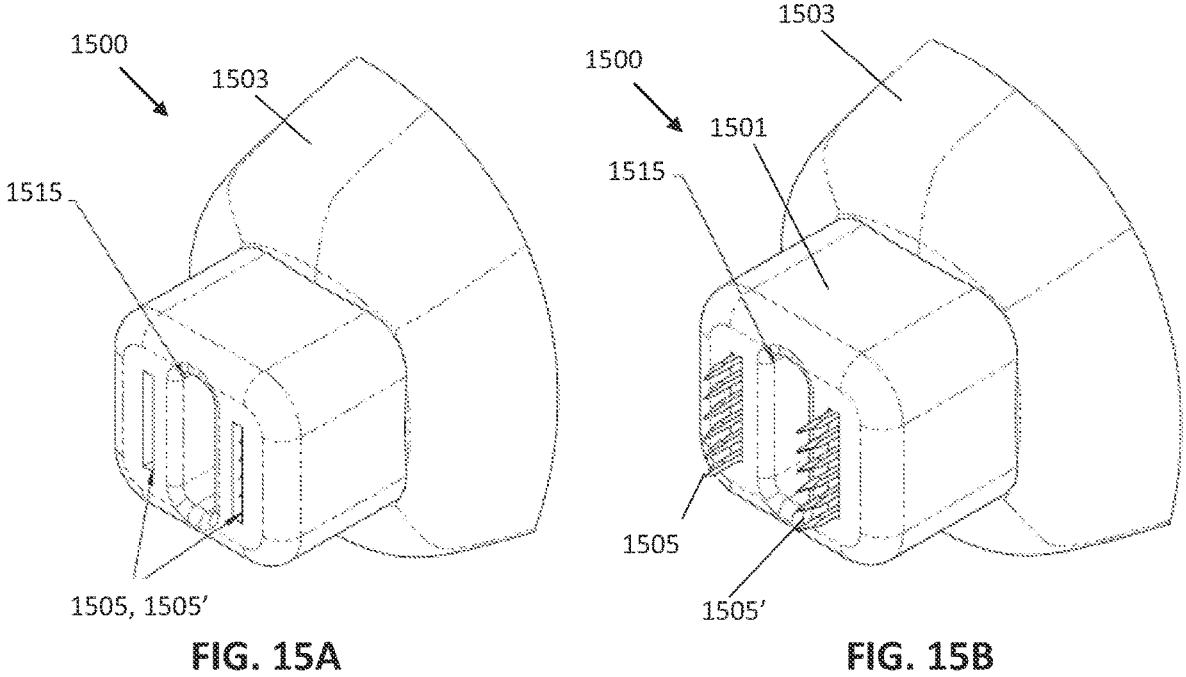
FIG. 15A
FIG. 15B
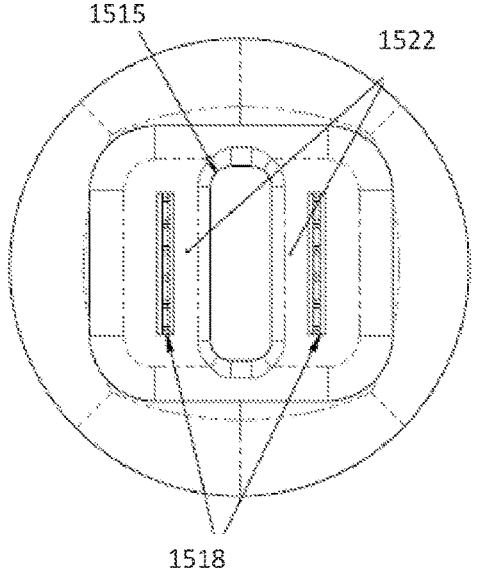
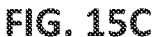
FIG. 15C
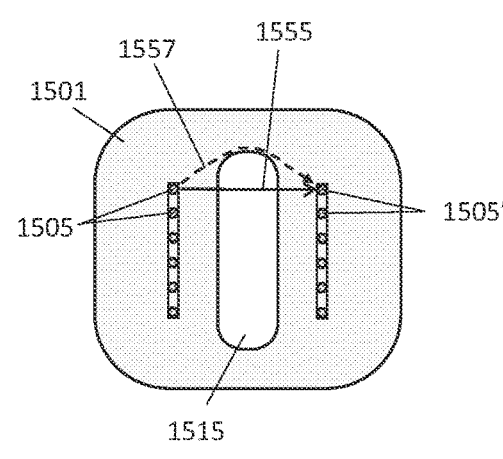
FIG. 15D

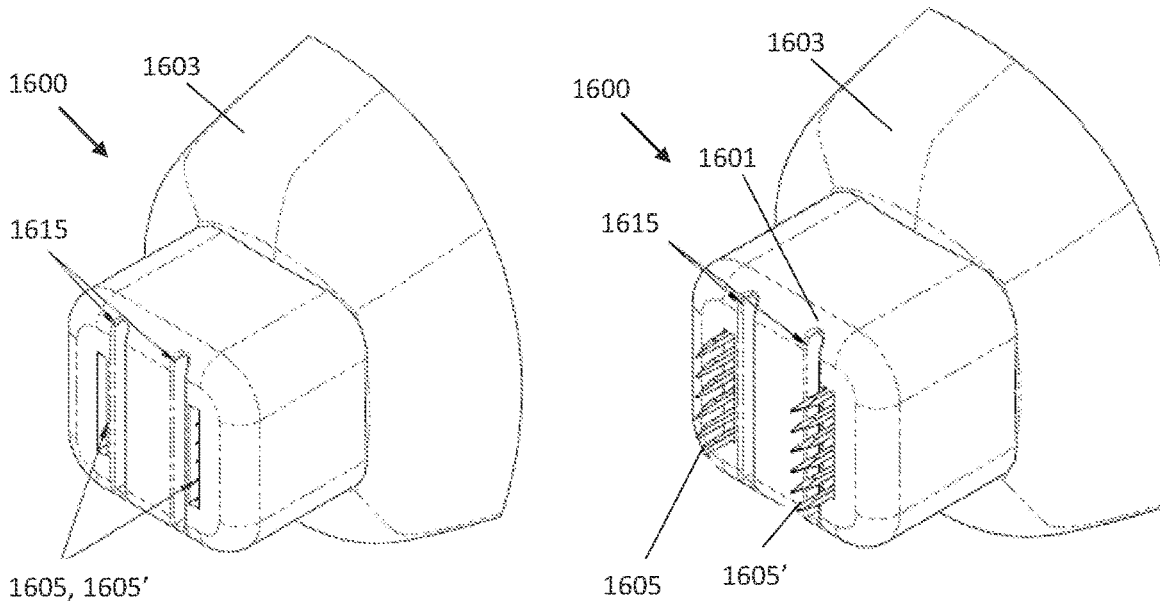
FIG. 16A                FIG. 16B
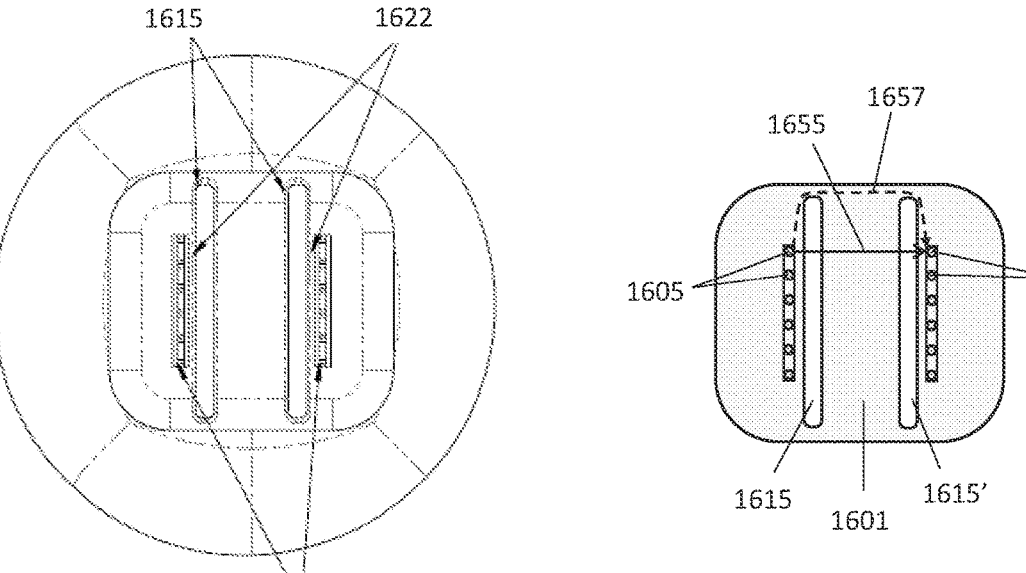
FIG. 16D
FIG. 16C

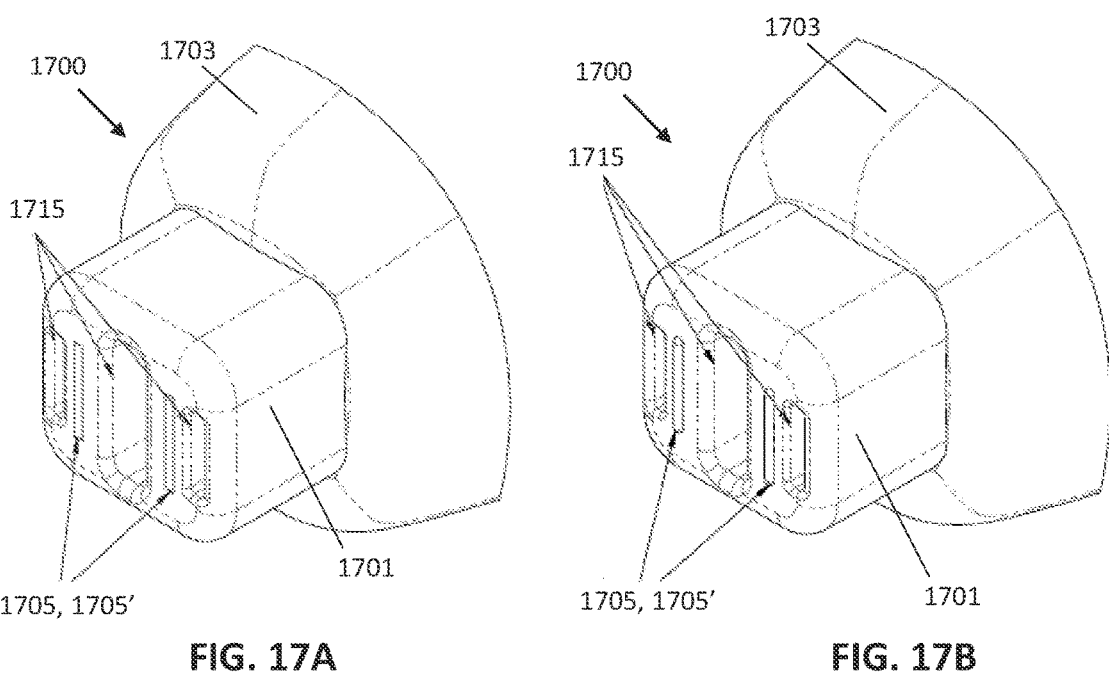
FIG. 17A
FIG. 17B
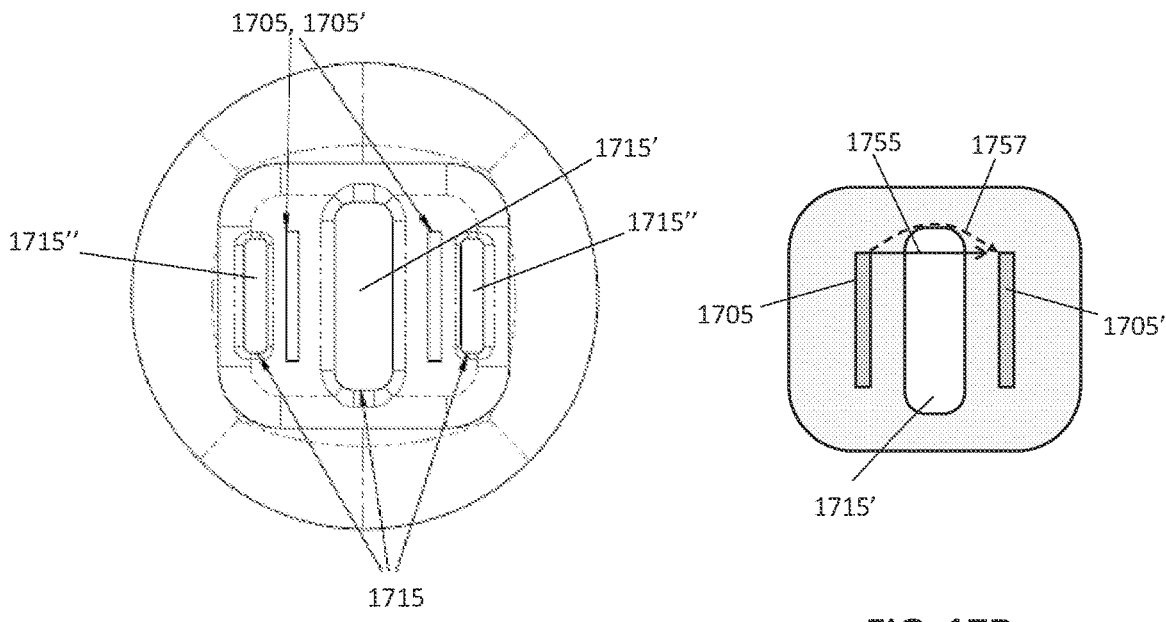
FIG. 17C
FIG. 17D

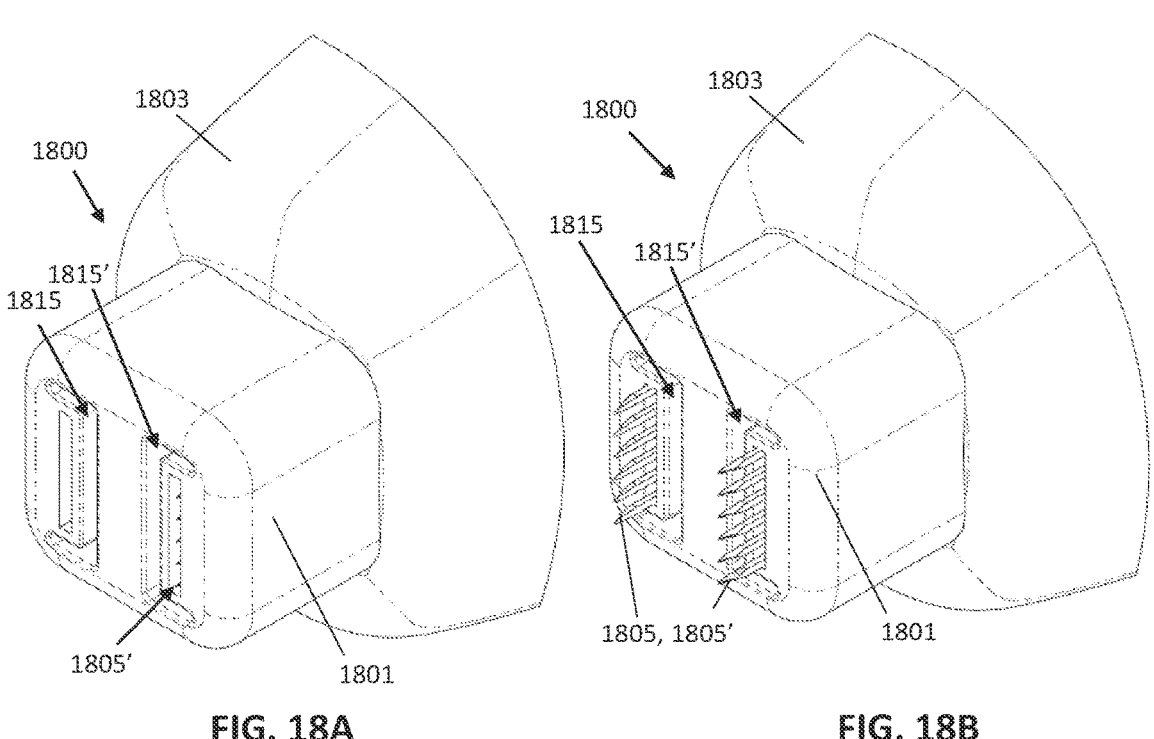
FIG. 18A                    FIG. 18B
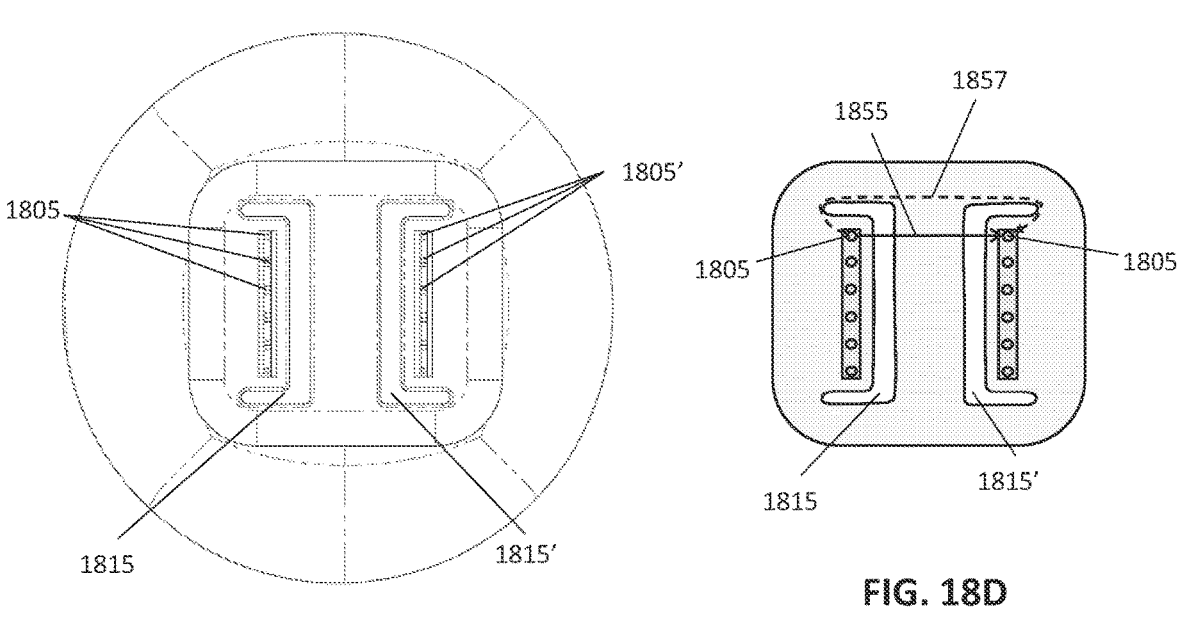
FIG. 18C
FIG. 18D

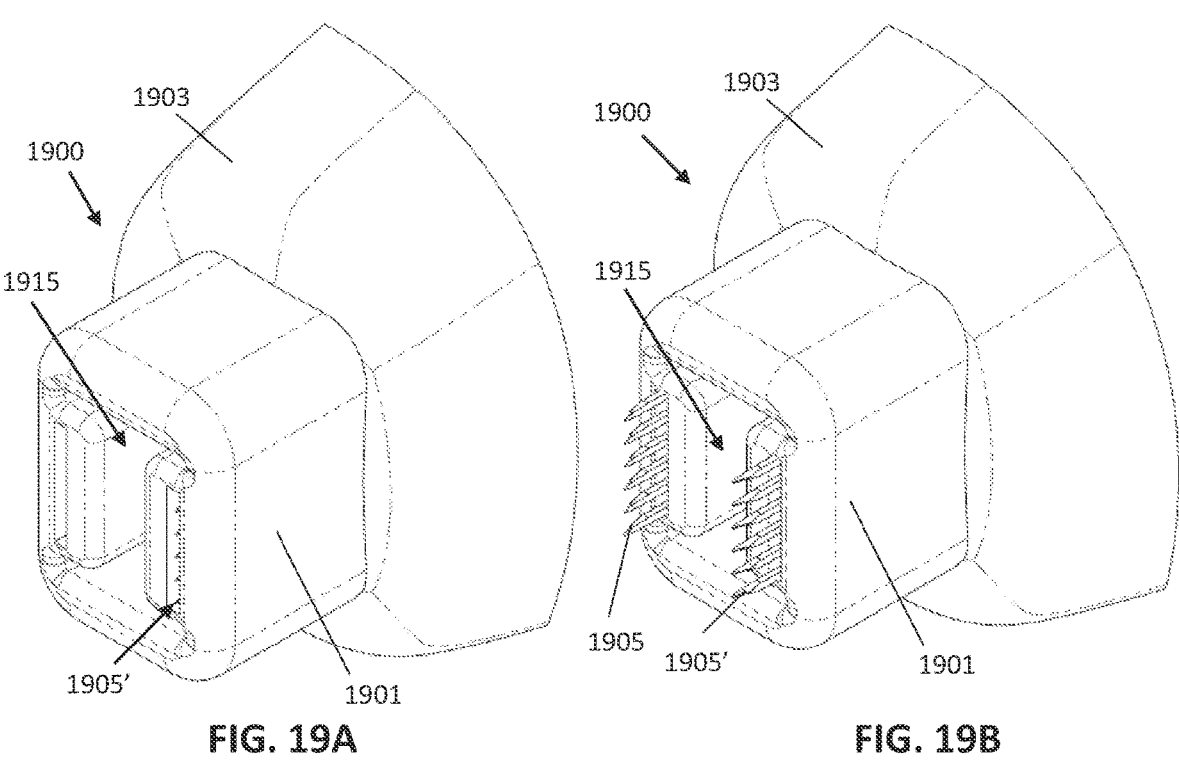
FIG. 19A                        FIG. 19B
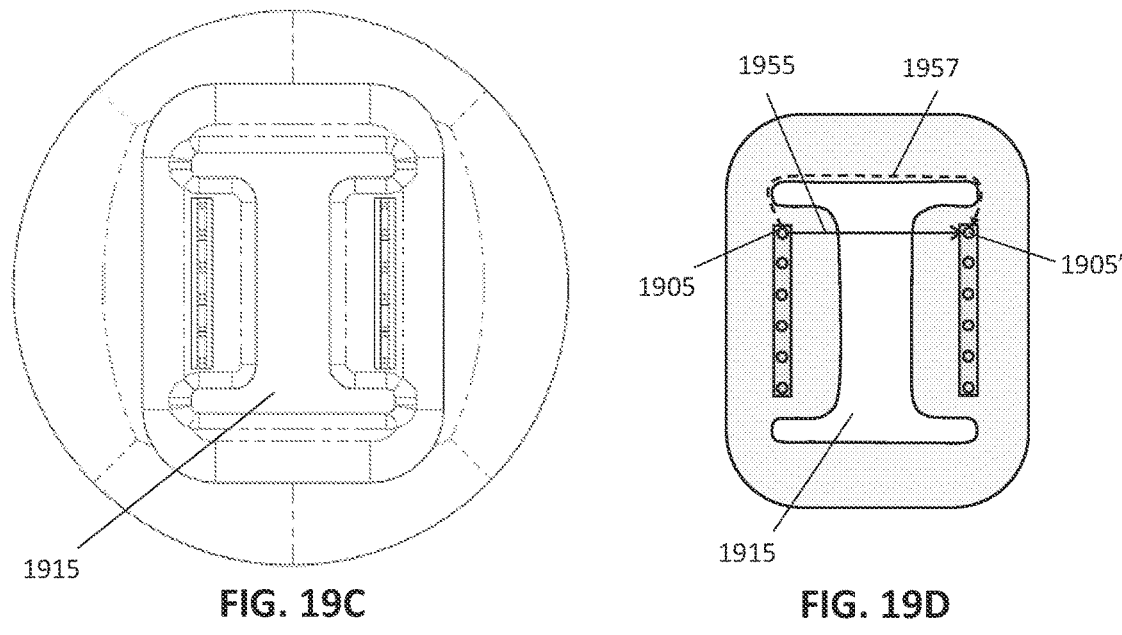
FIG. 19C                        FIG. 19D

2000

2001

2005

2035

2002

2031

2033

2100

2105

2101

2131

2135

2133

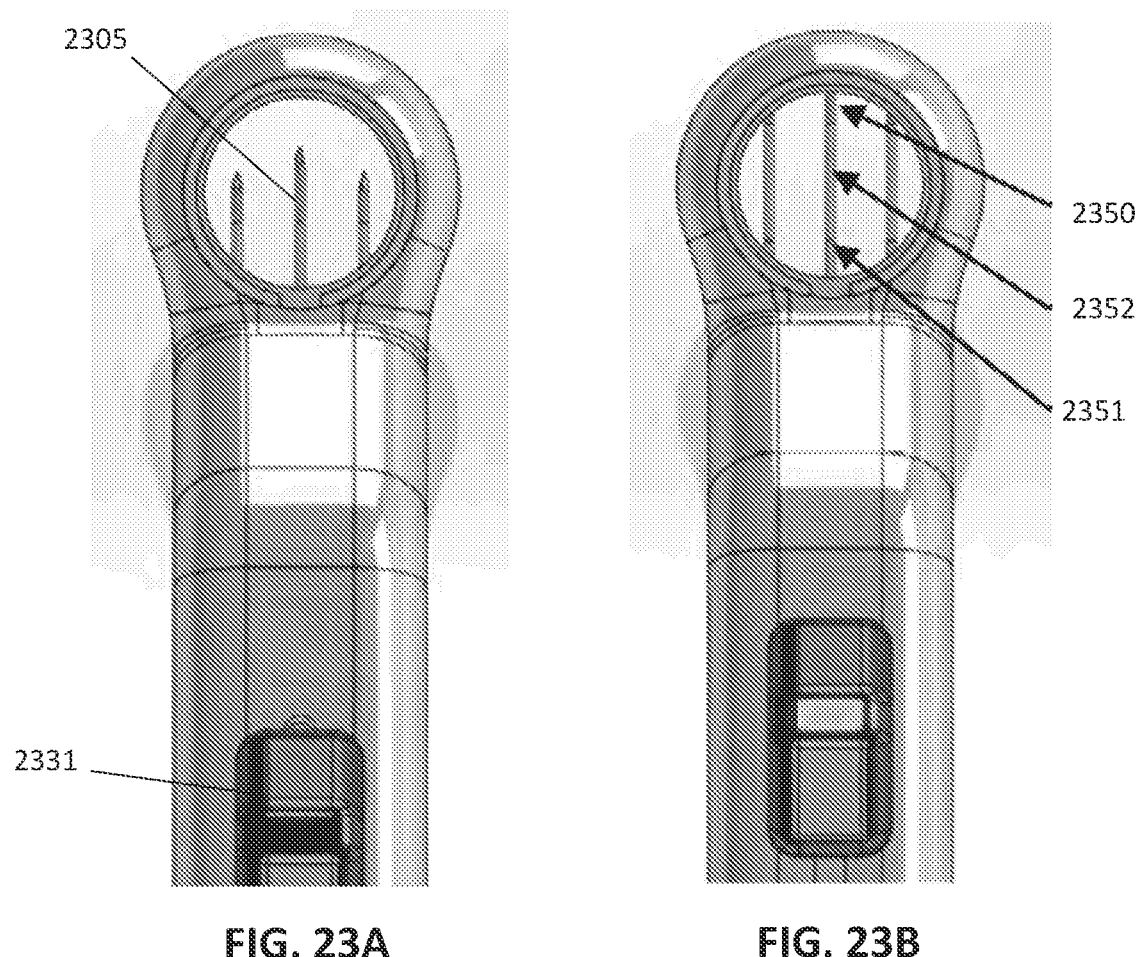
FIG. 23A                    FIG. 23B
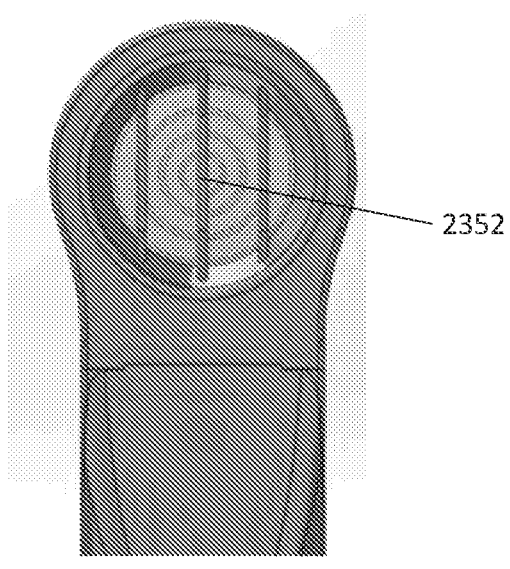
FIG. 23C

2415

2445

2415

2405

2445          2463

2415

2405

2445

2405

2462

2445          2452

2600

2603

2613

2601

2605

2607

2609

2600

2611

2600

D

A

2611

2601

2613

2605

2700

2703

2704

2702

2701

2706

2705

2700

2703'

2704

2702

2701

2706

2705

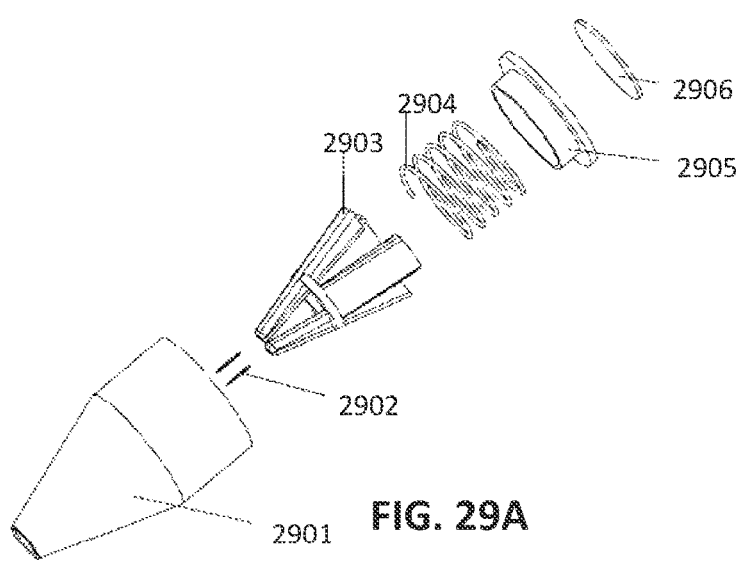
FIG. 29A
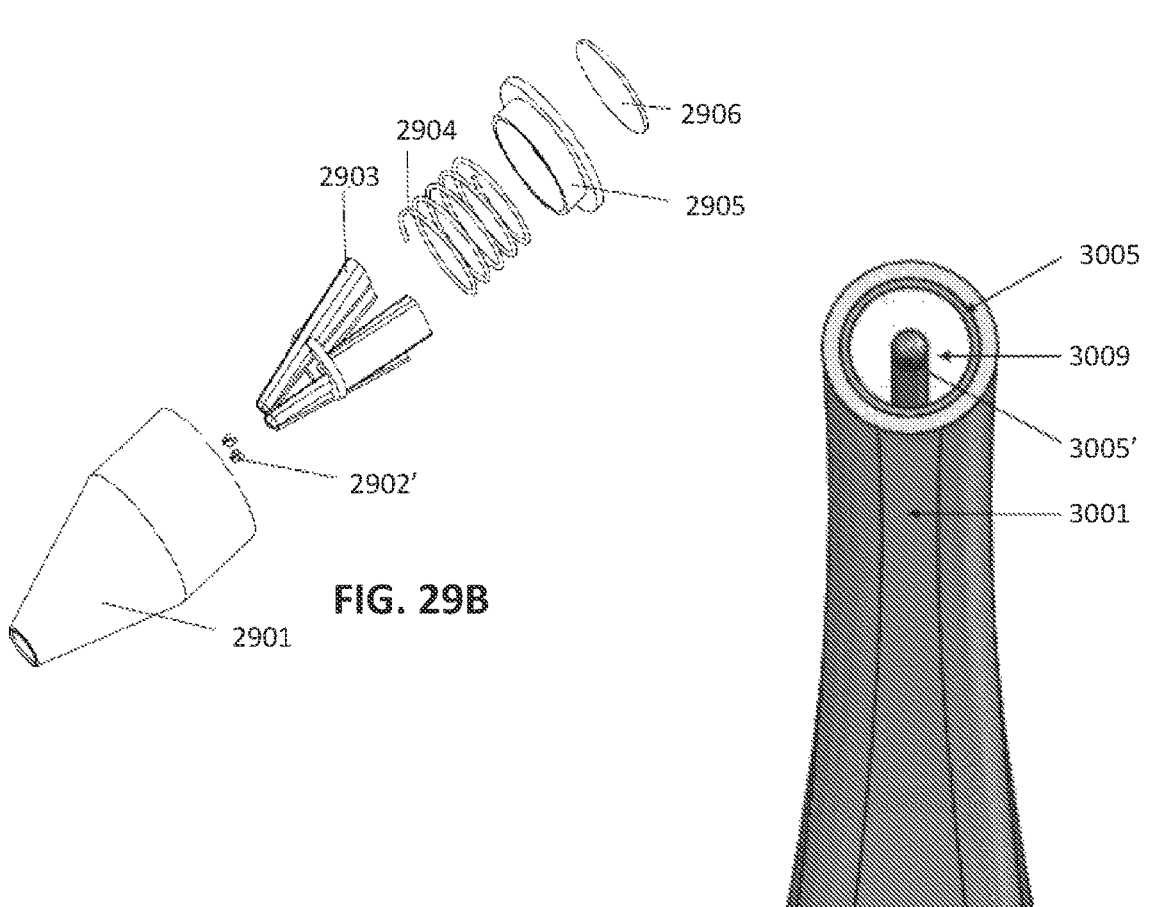
FIG. 29B
FIG. 30

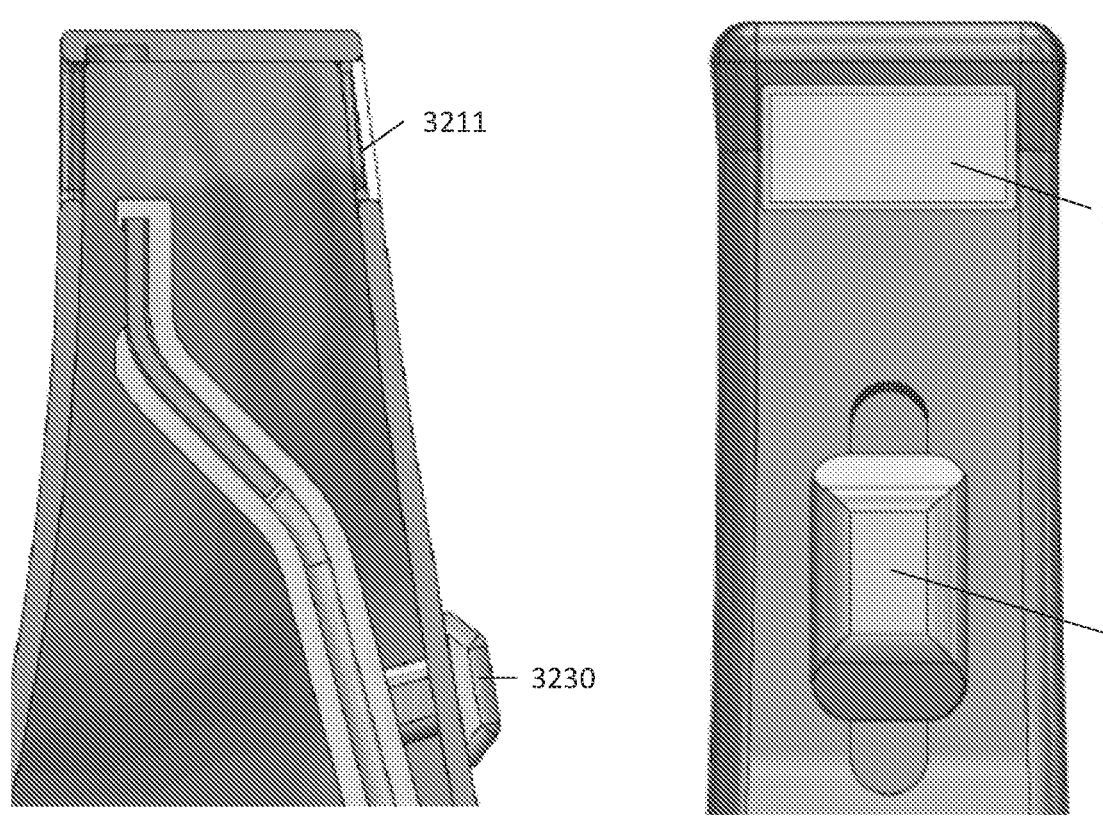
FIG. 32D
FIG. 32E
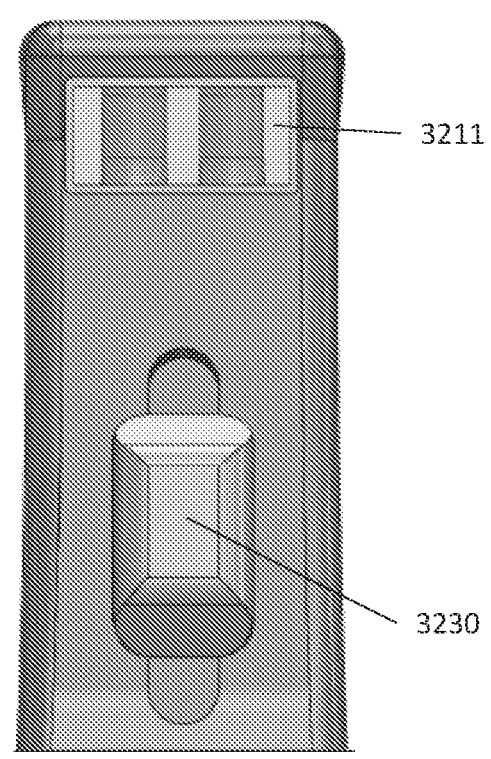
FIG. 32F

ELECTRICAL APPLICATORS FOR APPLYING ENERGY TO TISSUE SURFACES OR REGIONS SUPERFICIAL TO THE SURFACE

CROSS REFERENCE TO RELATED APPLICATIONS

This patent application is a national phase application under 35 U.S.C. 371 of International Patent No. PCT/US2022/074666, titled "ELECTRICAL APPLICATORS FOR APPLYING ENERGY TO TISSUE SURFACES OR REGIONS SUPERFICIAL TO THE SURFACE," filed on Aug. 8, 2022, now International Publication No. WO 2023/019108, which claims priority to U.S. provisional patent application No. 63/231,698, titled "ELECTRICAL APPLICATORS FOR APPLYING ENERGY TO TISSUE SURFACES OR REGIONS SUPERFICIAL TO THE SURFACE," filed on Aug. 10, 2021, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods and apparatuses described herein may be related to electrodes for the application of electrical energy to a subject, for example, a patient. More specifically, the methods and apparatuses described herein relate to the electrodes that may apply pulsed electrical energy (e.g., nanosecond pulsed electrical energy) to a surface of a patient's tissue, such as skin, or regions that are superficial to the tissue surface. These apparatuses and methods described herein may be particularly useful for improved targeting and positioning, as well as for avoiding or minimizing undesirable electrical modification of the tissues, including preventing or limiting electrical arcing.

BACKGROUND

Electrical energy may be applied within the tissue for a variety of purposes, including for the treatment of medical conditions. Electrical energy may be provided through an electrode of a treatment applicator that is placed on and/or inserted into the tissue. In some cases, the application of electrical energy by an electrode may result in the undesirable modification of the tissue at or around the electrode. Poor or inconsistent contact between the treatment applicator, including the electrode(s), and the tissue may result in such undesirable modifications, particularly when applying high-voltage or high power energy, and result in an uncontrolled electrical discharge, such as an arc.

These problems may be particularly acute when applying rapid, high-energy pulses, e.g., to treat patients. For example, nanosecond high voltage pulse generators have been described for biological and medical applications. See, e.g., U.S. Patent Application Publication No. 2010/0038971. The entire content of these publications is incorporated herein by reference.

Because of the very high therapeutic voltages, as well as the very fast pulse times, applicators for delivery of such sub-microsecond pulsing devices should ideally be configured so as to avoid, or at least minimize, arcing between the electrodes. Further, it would be beneficial to improve contact between the tissue and the applicator and electrodes, including preventing tenting of tissue around and/or between electrodes of the applicator. Tenting may occur when the tissue that is being penetrated or pressed against by the applicator, and/or one or more electrodes on the treatment tip, stretches around the electrode(s), leaving gaps. Tenting may lead to issues with targeting and controlling of the applied energy, including arcing, which may result in less favorable results of the electrical treatment.

The methods and apparatuses described herein may address various issues raised above, including improvement of the targeting of the treatment area.

SUMMARY OF THE DISCLOSURE

Described herein are apparatuses and methods for applying electrical energy to a subject's tissue using a treatment applicator (also referred to herein as simply an "applicator" or as an "applicator device") with one or more electrodes. These electrodes may be configured to be used in conjunction with suction, which may be locally applied to assist in establishing or maintaining contact with the tissue surface and/or superficial regions of the tissue. For example, described herein are treatment applicators having arrays of electrodes that may each be biased to apply a predetermined force against the tissue. These electrodes, which in some examples may be blunt or otherwise configured not to penetrate the tissue, may have an extended position so that contact with the surface of the tissue may drive the electrodes so that they at least partially retract into the treatment applicator while being driven with constant force against the tissue. In some examples these electrodes may be used in conjunction with suction applied around the electrodes, which may stabilize contact with the target tissue. The suction may be coupled with the electrodes, so that contact with the tissue (detected by retracting the electrodes) may trigger the application of suction.

The methods and apparatuses described herein may address the issues of arcing and tenting, as well as the targeting discussed above. For example, these methods and apparatuses may improve targeting a lesion area by giving the user ability to clearly see the targeted lesion when placing the treatment applicator on the tissue as well as continuing to see the lesion throughout the treatment.

Thus, energy may be applied directly to the skin surface using the one or more electrodes, which may reduce the physical trauma of inserting all the individual needles into the skin. These methods and apparatuses may also reduce the amount of arcing between the electrodes along the surface of the skin through any air gaps around the electrodes. This gap/air path between electrodes is one of the reasons for arcing. Various designs of the treatment applicator devices of the present application provide for vacuum between the electrodes that creates a seal between the tip of the treatment applicator and the tissue and blocks the gap/air between electrodes. These methods and apparatuses may further reduce the holding forces required to keep the constant contact with the tissue throughout a treatment. Removing the air gaps (e.g., tenting) and/or reducing the forces needed to apply the treatment applicator may improve the overall usability or case of use when treating tissue.

In some examples, the electrodes are biased so that contact with the tissue drives the electrodes (individually or collectively) to retract slightly, so that a bias associated with the electrode applies a counterforce against the tissue. In some examples, the electrodes are non-penetrating pin electrodes that are configured with a bias (e.g., spring) within and/or outside of the pin electrode. In some examples these electrodes may be configured with the bias (e.g., spring) within the pin electrode, similar to a POGO pin. A spring-loaded electrode may apply the force of the spring to make continuous contact with the tissue (e.g., skin). The non-penetrating electrode may have a smooth and/or round distal end (e.g., tip) and other external smooth surfaces, thus may be less likely to experience arcing. Sharp points are typically more susceptible to arcing when using high voltage pulses such as a nanosecond pulsed electrical treatment. Because the electrodes do not penetrate the skin they can be used in sensitive regions of the body, such as around the eyes or other places on the face and may minimize potential tissue damage from electrodes.

Any of the treatment applicators described herein may include non-penetrating (e.g., spring loaded) electrodes that are integrated with vacuum or suction ports; these suction ports may be located under and around each of the electrodes, and may help remove any air gaps around the electrode to help achieve a better or more complete contact with the tissue. Removing the air gaps around the electrodes may also reduce delays in the procedure due to arcing, which in turn will lead to a better or more consistent procedural outcomes. In case of the use of the penetrating electrodes (e.g., needle electrodes), these vacuum ports may also assist with the insertion of the needle electrodes into the tissue as well as reduce the forces the user needs to apply to the treatment applicator to start the procedure and/or during the ongoing procedure. The use of suction ports around each of the needles may create sufficient suction around the treatment area to hold the treatment applicator in place without requiring much force to be applied before and during a procedure. The suction may hold the electrodes against the surface of the tissue throughout the procedure, which may, in turn, reduce the likelihood of the arcs occurring thereby improving the outcome of the procedure.

In general, described herein are devices for delivering electrical treatment, including in particular treatment applicators (including those configured as removable/disposable treatment tips) for delivering electrical treatment. The electrical treatment may be pulsed (e.g., sub-microsecond, nanosecond, etc.) electrical energy. These tips may generally apply suction before and/or during the application of electrical treatment. In some examples each electrode (e.g., tissue penetrating or non-penetrating electrodes) may be surrounded by and/or may extend out of a suction port from which suction may be applied.

Also described herein are devices for delivery of electrical treatment that include: an electrode housing extending from a distal end of a treatment applicator; a first electrode or set of electrodes extending or configured to extend from the electrode housing, wherein the first electrode or set of electrodes are arranged across a first length of the electrode housing; a second electrode or set of electrodes extending or configured to extend from the electrode housing, wherein the second electrode or set of electrodes are arranged across a second length of the electrode housing that is parallel to the first length; and a suction port opening through the electrode housing and extending continuously between the first electrode or set of electrodes and the second electrode or set of electrodes, wherein the suction port extends further than the first length and the second length across the electrode housing so as to prevent arcing between the first electrode or set of electrodes and the second electrode or set of electrodes.

A device for delivery of electrical treatment may include: an electrode housing extending from a distal end of a treatment applicator; a first electrode or set of electrodes extending or configured to extend from the electrode housing; a second electrode or set of electrodes extending or configured to extend from the electrode housing; and a suction port opening through the electrode housing and extending continuously between the first electrode or set of electrodes and the second electrode or set of electrodes, wherein a strike distance, comprising a minimum path length between the first electrode or set of electrodes and the second electrode or set of electrodes and around the first suction port is 5% or more longer than a minimum distance between the first electrode or sets of electrodes and the second electrode or set of electrodes extending across the suction port so as to prevent arcing between the first electrode or set of electrodes and the second electrode or set of electrodes.

Also described herein are methods of operation and/or using any of these apparatuses (e.g., devices, systems, etc.). For example a method may include: applying a distal end of a treatment applicator against a tissue; contacting the tissue with a first electrode or first set of electrodes and a second electrode or second set of electrodes on an electrode housing of the treatment applicator; and preventing arcing between the first electrode or first set of electrodes and the second electrode or second set of electrodes by applying suction through a continuous suction port on the electrode housing extending between the first electrode or first set of electrodes and the second electrode or second set of electrodes so that tissue contacts the continuous suction port between and extending beyond on either side of the first electrode or first set of electrodes and the second electrode or second set of electrodes. The method further comprises applying a pulsed electrical treatment to the tissue from first electrode or first set of electrodes and the second electrode or second set of electrodes.

Any of the apparatuses (e.g., devices and systems, including applicators and applicators configured as disposable/removable treatment tips) for delivery of electrical treatment to a tissue described herein may include a viewing window for viewing the target tissue within the suction chamber of the apparatus. For example, a device may include: a suction chamber having an open bottom, a top surface and one or more sides, wherein the suction chamber comprises a viewing window; one or more electrodes configured to extend within the suction chamber and at least partially visible in the viewing window; and a suction port in fluid communication with the suction chamber to apply negative pressure therein.

For example, a treatment applicator device for delivery of electrical treatment to a tissue may include: a housing forming a suction chamber, the suction chamber having an open bottom, a top surface and one or more sides; one or more electrodes configured to move within the suction chamber; and a suction port in fluid communication with the suction chamber; wherein the suction chamber comprises a viewing window that is optically transparent, permitting a user to view a target tissue through the open bottom; one or more electrical connectors configured to electrically couple the one or more electrodes to a source of electrical energy; a control coupled to the one or more electrodes and configured to extend and retract the one or more electrodes within the suction chamber; and a vacuum connector configured to fluidly couple the suction port to a source of negative pressure.

Any of the apparatuses (devices and systems, including tips) may include a control for controlling the application of suction through the apparatus, including in particular through the tip or a suction chamber into which the tissue may be drawn for treatment or through which the apparatus may be held against the skin for treatment. In any of these apparatuses the control may include a bleed valve, allowing the user to manually turn on/off suction from a suction port or suction chamber on the tips of the apparatus and out of the bleed valve quickly and easily. For example, any of these apparatuses may include a bleed valve, e.g., on a handle of the apparatus, that may divert suction from a suction port and/or suction chamber until the user occludes it (e.g., by covering it), wherein the suction may be applied through the suction port and/or chamber. The bleed port may be part of the handle. Suction may be applied continuously but may only be directed to the suction chamber and/or suction ports at the treatment tip when activated by the user closing the bleed valve.

A method of using such an apparatus may include: applying a suction chamber of a treatment applicator against a tissue so that an open end of the suction chamber is held against the tissue and a target region of the tissue is visible through a viewing window of the suction chamber; applying a negative pressure in the suction chamber from a suction port in fluid communication with the suction chamber; and extending one or more electrodes within the suction chamber so that the one or more electrodes are in contact with the target tissue within the suction chamber. The method may further comprise applying a pulsed electrical treatment to the target tissue through the one or more electrodes.

For example, a method may include: applying a suction chamber of a treatment applicator against a tissue so that an open end of the suction chamber is held against the tissue and a target region of the tissue is visible through a viewing window of the suction chamber; applying a negative pressure in the suction chamber from a suction port in fluid communication with the suction chamber to draw the target tissue into the suction chamber; and extending one or more tissue-penetrating electrodes from out of the one or more sides and laterally across the suction chamber so that the one or more tissue-penetrating electrodes penetrate the tissue within the suction chamber. The method may further comprise applying a pulsed electrical treatment to the target tissue through the one or more electrodes.

Also described herein are methods of treating a condition, disease or disorder using any of these apparatuses. In particular, described herein are methods of treating syringoma. For example a method of treating syringoma may include: applying a suction chamber of a treatment applicator over a target syringoma on a subject's skin so that the target syringoma is visible through a viewing window of the suction chamber; applying a negative pressure in the suction chamber from a suction port in fluid communication with the suction chamber to draw the syringoma into the suction port and out of a plane of the subject's skin; contacting the target syringoma with one or more electrodes within the suction chamber; and applying sub-microsecond pulsed electrical energy to the syringoma through the one or more electrodes.

For example, also described herein are devices for delivery of electrical treatment or therapy to a surface of a tissue, the device comprising: an electrode housing extending from a distal end of a treatment applicator; one or more (e.g., a plurality of) suction ports opening into the electrode housing; and a plurality non-penetrating electrodes (in some examples, spring-loaded electrodes) extending from the electrode housing and configured not to penetrate the tissue, wherein the non-penetrating electrodes extend out of the suction ports in an extended configuration, further wherein each of the non-penetrating electrodes is configured to retract into the electrode housing when driven against the tissue; and a plurality of biases, wherein each non-penetrating electrode is coupled with a bias of the plurality of biases to push against the tissue when driven to restore the non-penetrating electrode to the extended configuration.

These devices may be treatment applicators that include the electrode housing and the electrodes described above. In some examples, these treatment applicators are configured as removable and/or replaceable treatment tips that include the electrode housing and non-penetrating electrodes; the removable/replaceable tip may be used with a reusable handpiece that is coupled to the pulse generator. For clarity and avoidance of any doubt, the term "handpiece" and the like, as used herein, is intended to describe a proximal portion of a treatment applicator assembly and is not limiting. It refers to any structure to support, hold or attach to the electrode portion of the device, whether it is intended to be hand-held, or attached to the robotic arm, or for percutaneous or other minimally invasive applications and for catheter-based delivery. In some examples the handpiece may be configured to be hand-held and may include a manual grip. In some examples, the handpiece may be configured to be held by a robotic manipulator (e.g., arm, etc.). In some examples, the handpiece may be configured for introduction through the scope or a catheter.

For example, described herein are devices, including devices for delivery of electrical treatment to a surface of a tissue that include: an electrode housing extending from a distal end of a treatment applicator; one or more (e.g., a plurality) of suction ports opening into the electrode housing; and one or more circumferential seals around the one or more (e.g., plurality) of suction ports and configured to seal the distal end of the treatment applicator against the tissue when suction is applied through the plurality of suction ports; a plurality of non-penetrating electrodes extending from the electrode housing and configured to not penetrate the tissue, wherein the non-penetrating electrodes extend out of the suction ports beyond the one or more circumferential seals in an extended configuration, further wherein each of the non-penetrating electrodes is configured to retract into the electrode housing when driven against the tissue; and a plurality of biases, wherein each non-penetrating electrode is coupled with a bias of the plurality of biases to push against the tissue when driven to restore the non-penetrating electrode to the extended configuration.

Any of these devices may include one or more circumferential seals around the one or more suction ports and configured to seal the distal end of the treatment applicator against the tissue when suction is applied through the plurality of suction ports. In some examples, the electrode housing may include an insulating distal end forming one or more seals around the plurality of suction ports and configured to seal the distal end of the treatment applicator against the tissue when suction is applied through the plurality of suction ports.

The distal end of the treatment applicator may be angled, e.g., relative to a long axis of the treatment applicator, so that the tissue-engaging face from which the electrodes extend is angled. For example, the distal end of the treatment applicator may be angled between about 5 and about 90 degrees relative to a long axis of the electrode housing.

The suction channel within the electrode housing may be in fluid communication with the plurality of suction ports. Any of these devices may include a suction connector at a proximal end of the electrode housing configured to couple with a source of negative pressure, for example, when a treatment tip of the treatment applicator is coupled with a handpiece. The connector may sealingly engage the connection on the handpiece.

Any of the devices described herein may be configured so that the application of negative pressure (suction) from the suction ports is coordinated with the non-penetrating electrodes. For example, the device may be configured so that vacuum is applied through the suction ports when the non-penetrating electrodes are pushed against the tissue (which may deflect them proximally into the electrode housing, opening suction channel to apply negative pressure (suction) from the suction port(s).

The non-penetrating electrodes may generally be configured as spring-loaded pins. For example, the plurality of non-penetrating electrodes may each comprise a blunt pin having an internal chamber housing a spring comprising the bias coupled with the non-penetrating electrode. Thus, in some examples each of the plurality of non-penetrating electrodes comprises a pogo-pin structure (e.g., having an internal spring element). Alternatively or additionally, each of the plurality of non-penetrating electrodes may comprise a wire electrode extending laterally across the distal end of the treatment applicator (e.g., a tip portion of the applicator); a portion of the electrode within the electrode housing may be coupled to a bias (e.g., spring) that may allow the electrode to be pushed into the housing and may exert a force against the tissue. In general, the biases include springs (e.g., coil springs, leaf springs, etc.), etc. The bias may be configured to apply a constant force against the tissue when driven to restore the non-penetrating electrode to the extended configuration.

Any of these devices may include one or more mechanical and/or electrical connectors at a proximal end of the treatment tip configured to removably couple the treatment tip to a handpiece (e.g., forming a treatment applicator assembly). The mechanical and electrical connector(s) may be integrated together. In some examples the treatment applicator (e.g., treatment tip) may include a separate suction connector and/or the suction connector(s) may be integrated with the mechanical and/or electrical connector(s).

As mentioned, the non-penetrating electrode may comprise a smooth, rounded and blunt tissue-contacting surface. In some examples the non-penetrating electrode has an enlarged distal end region that is larger in diameter than the more proximal region. The non-penetrating electrode may have a flat or flattened distal end tip.

Any of these devices (treatment applicators, treatment tips, etc.) may be part of a system that includes the pulse generator and/or a source of negative pressure. For example, described herein are systems including: a reusable handpiece comprising one or more electrical connectors and a vacuum connector at a distal end of the handpiece and any of the devices described herein. The treatment applicator (configured as a treatment tip) may be configured to releasably couple to the handpiece through the one or more electrical connectors and the vacuum connector. Any of these systems may include a pulse generator coupled to the reusable handpiece and/or a source of negative pressure within the reusable handpiece.

Also described herein are methods of using any of these apparatuses (devices, systems, e.g., treatment applicators). For example, a method may include: applying a distal end of a treatment tip against a tissue; drawing negative pressure at the distal end of the treatment tip so that each of a plurality of non-penetrating electrodes are driven against the tissue, and retracted at least partially into an electrode housing of the treatment tip, wherein a bias coupled to each of the non-penetrating electrodes applies a constant force against the tissue; and applying a pulsed electrical treatment to the tissue through the plurality of non-penetrating electrodes.

In particular, any of these methods may be used for cosmetic treatments, such as reducing or removing wrinkles, skin blemishes, etc.

Any of these methods may include sealing the distal end of the treatment tip against the tissue. In some examples, drawing negative pressure may include drawing negative pressure at the distal end of the treatment tip so that each of a plurality of non-penetrating electrodes are driven against the tissue, and independently retracted partially into the electrode housing.

Any of these methods may include coupling the treatment tip to a reusable handpiece of a pulse generator before applying the distal end of the treatment tip against the tissue.

In addition to the methods and apparatuses that include treatment applicators having non-penetrating electrodes that are self-biasing against the surface of the tissue, also described herein are treatment applicators having side-deploying needle electrodes (e.g., tissue penetrating electrodes) that are configured to penetrate transversely into the superficial region of the tissue just beneath the surface of the tissue. These treatment applicators may include a suction chamber that may have an open bottom into which tissue may be drawn by suction so that one or more needle electrodes may extend from out of a side of the suction chamber and into the tissue (e.g., skin) in parallel with the open bottom of the treatment applicator. The top of the suction chamber may be optically transparent so that the user may see the tissue (and identify the target region to be treated) through the top. In some examples the top may magnify the view through the tissue. The vacuum port may be in or next to the top surface of the suction chamber.

These vacuum-assisted, side-deploying treatment applicators may allow treatment of tissue near the surface, with fewer electrodes and/or less trauma to the tissue than other treatment applicators that penetrate the tissue transverse (rather than substantially parallel) to the tissue surface. Thus, these treatment applicators may cause less mechanical trauma to the tissue (e.g., skin tissue or epidermis), and may allow the overall treatment to occur below the skin. In addition, these treatment applicators may improve the targeting capabilities of the treatment applicator, by giving the users the ability to clearly see the targeted lesion when placing the treatment tip on the tissue as well as continue to see the lesion throughout the treatment.

In general, any of the apparatuses or methods described herein including deployable electrodes (such as, but not limited to side-deploying needle electrodes or non-penetrating electrodes) may be automatically, manually or semi-automatically deployed and/or retracted. For example, any of these apparatuses may include one or more solenoids to deploy and/or retract electrodes. In some examples the apparatus may also or alternatively include one or more biases (e.g., springs) to deploy and/or retract the needles. In some examples a biased solenoid may be used to both deploy (e.g., extend) and retract the one or more electrodes. A control for triggering the solenoid, e.g., to deploy or retract the electrode(s) may be included on the apparatus, such as on a handle portion of the apparatus, and/or as a pedal (e.g., foot pedal), switch, button, etc.

For example, described herein are treatment applicator devices for delivery of electrical treatment or therapy to a tissue, the device comprising: a suction chamber having an open bottom, a top surface and one or more sides there between; one or more needle electrodes configured to extend from out of the one or more sides to traverse across the suction chamber in a path that is parallel to the open bottom; and a suction port adjacent to the top surface.

Any of these treatment applicators may be configured as a tip region that is removable and/or replaceable, for use with a reusable handpiece; the suction chamber and electrode(s) may be part of the tip, which may removably couple to the handpiece. For example, described herein are devices for delivery of electrical treatment to a tissue, the device comprising: an applicator housing forming a suction chamber having an open bottom, a top surface and one or more sides there between; one or more needle electrodes configured to extend from within one of the one or more side traverse the suction chamber parallel to the open bottom; and a suction port adjacent to the top surface; wherein the top surface comprises a viewing window that is optically transparent, and comprises one or more marks indicting a path of the one or more needle electrodes into the suction chamber; one or more electrical connectors configured to electrically couple the one or more needle electrodes to a handpiece for a source of electrical energy; and a vacuum connector configured to fluidly couple the suction port to a source of negative pressure.

The top surface may include a viewing window that is optically transparent. The viewing window may include one or more marks (e.g., crosshairs, etc.) indicating the path of the one or more needle electrodes into the suction chamber. The viewing window may be configured to magnify.

The one or more needle electrodes may be configured to traverse completely across the suction chamber so that a tip of each of the one or more needle electrodes extends to or within the one or more sides on an opposite end of the suction chamber from which the one or more needle electrodes extends out of. Alternatively, the one or more needle electrodes may be configured to traverse partially across the suction chamber. The needle electrode may be configured so that the electrical energy is delivered from the body of the needle (e.g., from a region proximal to the tip of the needle electrode). For example, the one or more needle electrodes may be electrically insulated at a tip region and along its length except for a region proximal to the tip region that is configured to be within a middle portion of the suction chamber when the one or more needle electrodes is fully extended. Alternatively or additionally, the needle electrode may be configured so that the electrical energy is delivered from the tip of the needle electrode.

In any of these devices the one or more sides of the suction chamber may be configured to be adjustable to adjust a height of the suction chamber. For example, the one or more sides may be inflatable and/or expandable.

The suction chambers may have any appropriate shape, including square, rectangular, circular, etc. In some examples the suction chamber is shallow; for example, the top surface may extend across the suction chamber for a length that is three or more times longer than height of the one or more sides. In some variations the suction chamber has a length that is between 5 mm and 80 mm (e.g., between 5 mm and 70 mm, between 5 mm and 60 mm, between 5 mm and 50 mm, between 5 mm and 40 mm, etc.), and a depth that is between 1 mm and 30 mm (e.g., between 1 mm and 25 mm, between 1 mm and 20 mm, between 1 mm and 15 mm, between 1 mm and 10 mm, etc.).

In any of these suction chambers, the top surface may comprise an electrode. The electrode may be on the center of the top surface and/or on the periphery. In some variations the majority of the top surface (all or more than 90%, 85%, 80%, 75%, etc. of the top surface) is an electrode (e.g., return electrode).

Any of the suction chambers may include a seal (e.g., a scaling ring) around the open bottom of the suction chamber. The sealing ring may be formed of a flexible sealing material (e.g., silicone, etc.).

As mentioned, any of these treatment applicator devices may include a reusable handpiece and a removable tip, wherein the remove tip includes the suction chamber, one or more needle electrodes and the suction port. For example, the treatment applicator may include a control on the reusable handpiece to extend and retract the one or more needle electrodes.

As mentioned above, any of these treatment applicators may be configured as a system. A system may include any of the treatment applicator devices described herein and a pulse generator electrically coupled to the one or more needle electrodes.

Also described herein are methods of operating these apparatuses. These methods may include methods for cosmetic purposes, including methods for treating wrinkles, blemishes, etc.

For example, a methods may include: applying a suction chamber of a treatment applicator against a tissue so that an open bottom of the suction chamber is held against the tissue; applying a negative pressure in the suction chamber from a suction port adjacent to a top surface of the suction chamber; extending one or more needle electrodes from out of a side of the suction chamber and transversely into a tissue in the suction chamber so that the one or more needle electrodes extend parallel to the open bottom of the suction chamber; and applying a pulsed electrical treatment to the tissue through the one or more needle electrodes.

Any of these methods may include visualizing the tissue through a viewing window (which may also be referred to herein as a targeting window) in the suction chamber to position the suction chamber over a target region of the tissue. Applying the pulsed electrical treatment may include applying the pulsed electrical treatment between the one or more needle electrodes and an electrode on the top surface. The method may include adjusting a height of the suction chamber. For example, the method may include coupling a removable tip comprising the suction chamber and the one or more needle electrodes to a reusable handpiece of a pulse generator to form the treatment applicator before applying the treatment applicator against the tissue.

As mentioned, any of these apparatuses may be configured as a device or a system, including, for example, a hand-held or hand-operated device, a computer-controlled, and/or a robotically operated, or remotely operated device. These apparatuses may be configured with one electrode or more than one electrode. The electrode may be, e.g., an array of electrodes. The electrodes described herein are generally tissue penetrating electrodes.

The treatment applicators described herein, including a treatment tip portion of a treatment applicator, may also include an electrical connector for connecting to a source of electrical energy. For example, the power connector may be configured to electrically connect the one or more needle electrodes to a power source configured to apply high voltage power to the one or more needle electrodes having a peak voltage of between about 100 volts per centimeter (e.g., 0.1 kV/cm) and about 500 kV/cm (e.g., between about 0.5 kV/cm and about 500 kV/cm, between about 1 kV/cm and about 500 kV/cm, greater than about 0.1 kV/cm, greater than about 0.5 kV/cm, greater than about 1 kV/cm, etc.).

In general, the energy delivered by any of these treatment applicators may refer to the applied electrical energy. As used herein energy is applied by the electrode(s) during the application of energy treatment or therapy. The energy treatment may be continuous or pulsed. The energy treatment may be pulsed at a single frequency or a range of frequencies, including at a modulated frequency (e.g., having a carrier frequency).

As mentioned, any appropriate electrical energy may be applied while moving the electrodes relative to the tissue. For example, applying energy may comprise applying high-voltage nanosecond electrical pulses, such as applying a train of sub-microsecond electrical pulses having a pulse width of between 0.1 nanoseconds (ns) and 1000 nanoseconds (ns). Applying high-voltage nanosecond electrical pulses may comprise applying a train of sub-microsecond electrical pulses having peak voltages of between 10 kilovolts per centimeter (kV/cm) and 500 kV/cm. Applying high-voltage nanosecond electrical pulses may comprise applying a train of sub-microsecond electrical pulses at a frequency of between 0.01 (Hz) to 10,000 Hz. Applying energy may comprise applying microsecond electrical pulses, or picosecond electrical pulses.

The methods and apparatuses described herein may be used as part of any appropriate electrical treatment or therapy in which electrical energy is applied within the tissue (or in some cases on the surface of the tissue). Various examples of the present disclosure are useful for applying electrical treatment to a surface of the tissue, for example, to a surface of the skin for treatment of various skin conditions, lesions, tumors, growth or abnormalities. Both penetrating and non-penetrating electrodes of various embodiments may be used for treatment of the surface of the tissue, including epidermis of the skin. Similarly, various example of the present disclosure, including those with both penetrating electrodes and non-penetrating electrodes may be used for applying electrical treatment to subsurface areas of the tissue, including superficial treatment areas below epidermis. For example, the method of applying energy described herein may be used to treat one or more of the following: organ tissue cancer (e.g., lung cancer, kidney cancer, pancreatic cancer, colon cancer, breast cancer, etc.), skin cancer, cherry angioma, warts, keloids/scars, aging skin, dermatological conditions and/or disease, molluscum angioma, necrobiosis lipoidica (NBL), melisma, lipoma epidermal/sebaceous cyst, basal cell carcinoma, any type of tumors or abnormal tissue growth (e.g., benign tumors, precancerous tumors). Alternatively, or additionally, these methods may be methods of any other body tissue, including non-skin tissue (respiratory tissue, soft tissue, lung tissue, breast tissue, liver tissue, etc.).

Any power connector may be configured to electrically connect the one or more treatment applicators to a power source configured to apply high voltage power to the one or more electrodes, such as (but not limited to) power having a peak voltage of between 10 kilovolts per centimeter (kV/cm) and 500 kV/cm.

For example, described herein are apparatuses (e.g., devices, including treatment applicator devices) for delivery of electrical treatment or therapy in which some or all of the individual electrodes may be independently extended or retracted, relative to each other and/or relative to electrode housing. These device may include: an electrode housing extending from a distal end of a treatment tip; one or more suction ports opening into the electrode housing; and a plurality of electrodes extending from the electrode housing, wherein each electrode is configured to independently retract into or extend out of the electrode housing when driven against the tissue; and a plurality of biases, wherein each electrode is independently coupled with a bias of the plurality of biases to push against the tissue when driven to restore the electrode to an extended configuration.

In some examples, it may be advantageous to also have the electrode housing be extendable and retractable relative to the treatment tip body and/or the electrodes. For example, in any of these treatment applicator devices the electrode housing may be also configured to extend and retract relative to distal end of the treatment tip. For example, any of these treatment applicator devices (including the tip region) may include a bias applying a force to restore the electrode housing to an extended configuration relative to the distal end of the treatment tip.

Any appropriate electrode may be used in any of these treatment applicator devices. For example, the electrodes may be non-penetrating electrodes or penetrating electrodes; the same treatment applicator device may include a combination of penetrating (tissue-penetrating) and non-penetrating. For example, each electrode of the plurality of electrodes may comprise a smooth, rounded and/or blunt tissue-contacting surface.

Any of these devices may include one or more circumferential seals around the one or more suction ports and configured to seal the distal end of the treatment tip against the tissue when suction is applied through the plurality of suction ports. The electrode housing may include an insulating distal end forming one or more seals around the one or more suction ports and configured to seal the distal end of the electrode housing against the tissue when suction is applied through the one or more suction ports.

As mentioned above, the distal end of the treatment tip may be flat or angled, e.g., angled between 5 and 90 degrees relative to a long axis of the electrode housing. Any of these apparatuses may include a suction channel within the electrode housing in fluid communication with the one or more suction ports.

In some examples the individually biased electrodes may each comprise an internal chamber comprising the bias (e.g., a spring) coupled with the electrode. For example, each of the electrodes of the plurality of electrodes may comprise a non-penetrating pogo-pin.

Any of these devices may include a mechanical and/or electrical connector at a proximal end of the treatment tip configured to removably couple the treatment tip to a handpiece.

Any of these devices described herein may be configured as a replaceable treatment tip (e.g., disposable, single patient use) that may releasably couple to the reusable handpiece through one or more electrical connectors and a vacuum connector.

Any of these apparatuses (e.g., devices) may include a pulse generator coupled to a handpiece, such as the reusable handpiece. Any of these apparatuses (e.g., devices) may include a source of negative pressure within the reusable handpiece.

Also described herein are methods of using treatment applicator devices that include individually biased tips. For example, a method (e.g., a method of treating a tissue) may include: applying a distal end of a treatment tip against a tissue; drawing negative pressure through an electrode housing at the distal end of the treatment tip so that each of a plurality of electrodes of the treatment applicator device are independently driven against the tissue and retracted at least partially into the electrode housing, wherein each of the electrodes is independently driven against the tissue by one of a plurality of biases; and applying a pulsed electrical treatment to the tissue through the plurality of electrodes. As mentioned, driving the distal end of the treatment tip against the tissue may comprise retracting the electrode housing into the treatment tip against a housing bias force, wherein the electrode housing is driven distally relative to the treatment tip by a housing bias.

Any of these methods may include scaling the distal end of the treatment tip against the tissue. The methods of the present disclosure also include methods of operation of various devices described herein. The methods described herein may include coupling the treatment tip to a reusable handpiece of a pulse generator before applying the distal end of the treatment tip against the tissue. The electrodes may extend out of one or more suction ports in the electrode housing. The plurality of electrodes that are independently driven against the tissue may be non-penetrating electrodes.

Also described herein are treatment applicator devices for delivery of electrical treatment or therapy to a tissue that include one or more windows for viewing (and targeting) the tissue to be treated. For example, an apparatus (device) may include: a suction chamber having an open bottom, a top surface and one or more sides, wherein the suction chamber comprises a viewing window; one or more electrodes configured to extend across the suction chamber to be at least partially visible in the viewing window; and a suction port in fluid communication with the suction chamber to apply negative pressure therein.

The one or more electrodes may be configured to extend from out of the one or more sides to traverse across the suction chamber in a path that is parallel to the open bottom. In some examples the one or more electrodes are configured to extend from out of the top to traverse across the suction chamber. In some examples the one or more electrodes are configured to extend in a curved path across the suction chamber. In some examples the one or more electrodes are configured to traverse completely across the suction chamber so that a tip of each of the one or more electrodes extends to or within the one or more sides of the suction chamber.

The viewing window may generally be optically transparent (including formed of a transparent material, such as a polymeric material, glass, etc.). The viewing window may be formed on any portion of the chamber, such as one or more of: the top surface, and/or in the one or more sides. As mentioned above, in general the viewing window may comprise one or more marks indicating the path of the one or more electrodes into the suction chamber. The viewing window may be configured to magnify.

In any of these apparatuses (e.g., devices, treatment tips, etc.) the one or more electrodes may be electrically insulated at a tip region and along its length but not insulated in a region proximal to the tip region that is configured to be within a middle portion of the suction chamber when the one or more electrodes is fully extended.

As mentioned, any of these treatment applicator devices may comprise a removable tip configured to be removably coupled to a handpiece. Any of these apparatuses may be part of a system including a pulse generator electrically coupled to the one or more electrodes.

According to another aspect of the present disclosure, also described herein are treatment applicator device for delivery of electrical treatment to a tissue, the devices comprising: a housing forming a suction chamber, the suction chamber having an open bottom, a top surface and one or more sides;

one or more electrodes configured to move within the suction chamber; and a suction port in fluid communication with the suction chamber; wherein the suction chamber comprises a viewing window that is optically transparent, permitting a user to view a target tissue through the open bottom; one or more electrical connectors configured to electrically couple the one or more electrodes to a source of electrical energy; an electrode movement control input coupled to the one or more electrodes and configured to extend and retract the one or more electrodes within the suction chamber; and a vacuum connector configured to fluidly couple the suction port to a source of negative pressure.

A method (e.g., a method of treatment) may include: applying a suction chamber of a treatment applicator against a tissue so that an open end of the suction chamber is held against the tissue, so that a target region of the tissue is visible through a viewing window of the suction chamber; applying a negative pressure in the suction chamber from a suction port in fluidic communication with the suction chamber; extending one or more electrodes within the suction chamber so that the one or more electrodes are in contact with the target tissue within the suction chamber; and applying a pulsed electrical treatment to the target tissue through the one or more electrodes. Applying the negative pressure may comprise applying negative pressure from the suction port that is adjacent to a second end opposite to the open end of the suction chamber. Any of the methods described herein in reference to different examples and embodiments may include visualizing the tissue through the viewing window.

Applying the pulsed electrical treatment may comprise applying the pulsed electrical treatment between the one or more electrodes and a second electrode on the surface of the suction chamber.

In general, these apparatuses and methods may allow improved targeting of a target tissue (e.g., lesion) area by giving the user the ability to clearly see the target region when placing the treatment tip on the tissue. These methods and apparatus may also allow the user to continue to see the lesion throughout the treatment. Thus, any of these apparatuses and methods may allow visualization. As described above and in further detail herein, any of these apparatuses may include a window (e.g., a viewing window or visualization window). Such apparatuses may be used with either or both penetrating and non-penetrating electrodes. These apparatuses and methods may preferably (but not necessarily) be used with suction.

In some examples the apparatus (and method of using it) may be configured as a side-deployable treatment device with penetrating electrodes that may provide sub-surface application of treatment energy. This may help minimize or prevent damage or injury to the surface area above the treatment region, including, but not limited to, in skin/epidermis.

For example, a treatment applicator device for delivery of electrical treatment to a tissue may include: a suction chamber having an open bottom, a top surface and one or more sides therebetween; a plurality of suction ports in fluid communication with the suction chamber; one or more needle electrodes, wherein each needle electrode extends from a respective suction port of the plurality of suction ports at a fixed height so that the one or more needle electrodes are driven into the tissue a predetermined depth when suction is applied when the device is held against the tissue.

A treatment applicator device for delivery of electrical treatment or therapy to a tissue may include: a applicator housing forming a suction chamber having an open bottom, a top surface and one or more sides; a first one or more electrodes within the applicator housing and configured to move within the suction chamber; a second electrode disposed on a circumference of the open bottom; wherein the suction chamber comprises a viewing window that is optically transparent; a control on the applicator housing configured to adjust position of the first one or more electrodes within the suction chamber to move the first one or more electrodes relative to a field of view of the viewing window; and a vacuum connector configured to fluidly couple the suction chamber to a source of negative pressure.

A treatment applicator device for delivery of electrical treatment to a tissue may include: an applicator housing forming a suction chamber having an open bottom and one or more sides; one or more tissue penetrating electrodes configured to extend across the suction chamber above the open bottom of the suction chamber; a viewing window into the suction chamber that is optically transparent providing a view of the open bottom of the suction chamber; a control configured to extend the one or more tissue-penetrating electrodes across the suction chamber; and a vacuum connector configured to fluidly couple the suction chamber to a source of negative pressure. The one or more tissue-penetrating electrodes may be configured to extend from out of the one or more sides and to traverse across the suction chamber in a path that is parallel to the open bottom. The one or more tissue-penetrating electrodes may be configured to extend in a curved path across the suction chamber. The one or more tissue-penetrating electrodes may be configured to traverse completely across the suction chamber so that a tip of each of the one or more tissue-penetrating electrodes extends to or within the one or more sides of the suction chamber.

As mentioned, the viewing window may be on any part (or through a part) of the chamber, such as the top surface of the suction chamber and/or the one or more sides.

According to a further aspect of the present disclosure, a method of treatment using these apparatuses may include: applying a suction chamber of a treatment applicator against a tissue so that an open end of the suction chamber is held against the tissue, and so that a target region of the tissue is visible through a viewing window of the suction chamber; applying a negative pressure in the suction chamber from a suction port in fluidic communication with the suction chamber; extending one or more tissue-penetrating electrodes from out of the one or more sides so that the one or more tissue-penetrating electrodes penetrate the tissue within the suction chamber in parallel to the open end of the suction chamber; and applying a pulsed electrical treatment to the target tissue through the one or more electrodes.

As mentioned above, and described in greater detail herein, any of these treatment applicator devices may be configured with a suction port on the tip (e.g., on the electrode housing) between and separating electrodes or groups (sets) of electrodes. The one or more suction ports may be arranged to form a suction barrier between the electrodes or groups of electrodes. For example, a treatment applicator device for delivery of electrical treatment to a tissue may include: an electrode housing extending from a distal end of a treatment tip; a first one or a set of tissue-penetrating electrodes; a second one or a set of tissue-penetrating electrodes, wherein the first one or the set of tissue-penetrating electrodes and the second one or the set of tissue-penetrating electrodes are configured to extend from a first position within the electrode housing to a second position proud of the electrode housing; and one or more suction ports between and separating the first one or the set of tissue-penetrating electrode and the second one or the set of tissue-penetrating electrodes, wherein the one or more suction ports are adjacent to the first one or the set of tissue-penetrating electrode and to the second one or the set of tissue-penetrating electrodes.

The one or more suction ports may comprise a single suction port located at a center of an outer surface of the electrode housing. The one or more suction ports may be arranged on either side of the first one or the set of tissue-penetrating electrodes and the second one or the set of tissue-penetrating electrodes. The one or more suction ports may comprise two or more suction ports each arranged in parallel across an outer surface of the electrode housing between and separating the first one or the set of tissue-penetrating electrode and the second one or the set of tissue-penetrating electrodes. As mentioned above, each of the electrodes of the first one or the set of tissue-penetrating electrode and the second one or the set of tissue-penetrating electrodes may be independently biased so that they may each independently retract relative to the electrode housing. Alternatively or additionally, the electrode housing may be biased so that it may retract relative to a body of the treatment tip.

Various example devices and methods described herein may be used for treating a relatively large treatment area by using, for example, a plurality of surface electrodes arranged as described herein. Further devices and methods of the present disclosure may be used for treatment of various specific conditions as described herein. Other features and advantages of the devices and methods of the present disclosure will become apparent from the following detailed description of one or more implementations when read in view of the accompanying figures.

BRIEF DESCRIPTION OF THE DRAWINGS

The sizes and relative positions of elements in the drawings are not necessarily drawn to scale. For example, the shapes of various elements and angles are not drawn to scale, and some of these elements are enlarged and positioned to improve drawing legibility. The novel features of the inventions described herein are set forth with particularity in the claims that follow. A better understanding of the features and advantages of the present methods and apparatuses will be obtained by reference to the following detailed description that sets forth illustrative embodiments, and the accompanying drawings of which:

FIG. 2A shows the distal end of a treatment applicator in section separated from a target tissue. FIG. 2B shows a similar sectional view of the tip of the treatment applicator of FIG. 2A placed against the tissue before suction is applied. FIG. 2C shows a sectional view of the tip pressed against the tissue with suction being applied from the suction ports.

FIGS. 3A-3B illustrate one example of a tip of a treatment applicator as described herein, showing an array of four (2x2) spring-loaded non-penetrating electrodes. FIG. 3A shows the distal end of the treatment applicator (an example of a treatment tip that is removable and/or disposable), while FIG. 3B shows a side view.

FIGS. 4A-4B illustrate another example of a tip of an applicator as described herein, showing an array of 8 (4x4) spring-loaded non-penetrating electrodes. FIG. 4A shows the distal end of the treatment applicator (e.g., a removable treatment tip) in a side perspective view, while FIG. 4B shows the distal end of the same treatment applicator.

FIG. 5A shows a side view of a treatment applicator (configured as a removable treatment tip) including spring-loaded non-penetrating electrodes. FIG. 5B shows a distal end view of the treatment tip of FIG. 5A. FIG. 5C shows a side perspective view of the treatment tip.

FIGS. 6A-6C illustrate another example of a treatment applicator as described herein. FIG. 6A shows a side view of a treatment tip (treatment applicator) including pin (and spring-biased) electrodes. FIG. 6B shows a distal perspective view of the treatment tip of FIG. 6A. FIG. 6C shows a side perspective view of the treatment tip.

FIGS. 7A-7C illustrate another example of a treatment applicator as described herein. In this example the non-penetrating electrodes are wire electrodes showing a flattened loop of wire forming the electrode that is spring-loaded as described herein. FIG. 7A shows a side view of a treatment tip including spring-loaded non-penetrating electrodes. FIG. 7B shows a distal perspective view of the treatment tip of FIG. 7A. FIG. 7C shows a side perspective view of the treatment tip.

FIG. 12A shows an exemplary side view. FIGS. 12B-12D show treatment tips of different dimensions and number of rows of electrodes each surrounded by a suction port/channel. FIG. 12E shows top perspective views of three examples of treatment tips as described.

FIG. 13B shows an enlarged view of the treatment tip of FIG. 13A.

FIG. 14B shows a perspective, section view through the treatment tip of FIG. 14A; FIG. 14C shows a side view of the treatment tip of FIG. 14A.

FIG. 15A shows an example of a treatment tip (e.g., a treatment applicator) having a central vacuum port between tissue-penetrating electrodes that may ensure contact between the electrode housing and the tissue. FIG. 15B shows the treatment tip of FIG. 15A with the tissue-penetrating (e.g., needle) electrodes extended. FIG. 15C shows a distal end view of the treatment tip of FIGS. 15A-15B.

FIG. 15D illustrates the strike distance for the electrodes in the treatment tip of FIGS. 15A-15C.

FIG. 16A shows an example of a treatment tip having a plurality (e.g., two) of vacuum ports between and adjacent to two sets of tissue-penetrating electrodes. FIG. 16B shows the treatment tip of FIG. 16A with the tissue-penetrating (e.g., needle) electrodes extended. FIG. 16C shows a distal end view of the treatment tip of FIGS. 16A-16B.

FIG. 16D illustrates the strike distance for the electrodes in the treatment tip of FIGS. 16A-16C.

FIG. 17A shows an example of a treatment tip having a central vacuum port between non-penetrating electrodes (e.g., wire electrodes) and outer vacuum ports, so that either side of each set of non-penetrating electrodes is flanked by vacuum ports. FIG. 17B shows the treatment tip of FIG. 17A with the electrodes extended. FIG. 17C shows a distal end view of the treatment tip of FIGS. 17A-17B.

FIG. 17D illustrates the strike distance for the electrodes in the treatment tip of FIGS. 17A-17C.

FIG. 18A shows an example of a treatment tip having two C-shaped vacuum ports between two sets of tissue penetrating electrodes (e.g., needle electrodes), with the vacuum ports between and partially surrounding the sets of tissue penetrating electrodes. FIG. 18B shows the treatment tip of FIG. 18A with the electrodes extended. FIG. 18C shows a distal end view of the treatment tip of FIGS. 18A-18B.

FIG. 18D illustrates the strike distance for the electrodes in the treatment tip of FIGS. 18A-18C.

FIG. 19A shows an example of a treatment tip having an I-shaped vacuum port between two sets of tissue penetrating electrodes (e.g., needle electrodes), with the vacuum port between and partially surrounding the sets of tissue penetrating electrodes. FIG. 19B shows the treatment tip of FIG. 19A with the electrodes extended. FIG. 19C shows a distal end view of the treatment tip of FIGS. 19A-19B.

FIG. 19D illustrates the strike distance for the electrodes in the treatment tip of FIGS. 19A-19C.

FIGS. 23A-23C illustrate another example of a treatment tip similar to that shown in FIGS. 22A-22C, showing a suction chamber having a transparent surface allowing targeting of the tissue. FIG. 23A shows the treatment tip with three needle electrodes partially extended across the suction chamber, parallel to the open bottom of the suction chamber. FIG. 23B shows the three needle electrodes fully extended across the suction chamber, so that they extend to the opposite side wall of the chamber. FIG. 23C shows a bottom view of the example treatment tip of FIGS. 23A-23B looking up through the open bottom to the transparent top (e.g., the viewing window that includes concentric targeting rings).

FIG. 28A shows the tip before engaging tissue, while FIG. 28B shows the tip engaged with tissue.

FIGS. 29A-29B show examples of exploded views of a treatment applicator including a vacuum treatment tip having either tissue-penetrating electrodes (FIG. 29A) or non-penetrating electrodes (FIG. 29B) similar to those shown in FIGS. 28A-28D.

FIG. 30 shows an example of a treatment tip as described herein.

FIG. 31A shows a view, showing the transparent window with the electrode advanced to contact tissue within the suction chamber. FIG. 31B shows the same view as FIG. 31A but with the electrode retracted. FIG. 31C shows a side, sectional view through the treatment tip shown in FIG. 31A. FIG. 31D shows a side, sectional view through the treatment tip shown in FIG. 31B.

FIG. 32D is a side, sectional view of the treatment tip of FIGS. 32A-32B with the electrodes retracted.

FIGS. 32E and 32F show an example of another treatment tip with the electrodes retracted (FIG. 32E) and extended (FIG. 32F), respectively.

DETAILED DESCRIPTION

Figure 1:
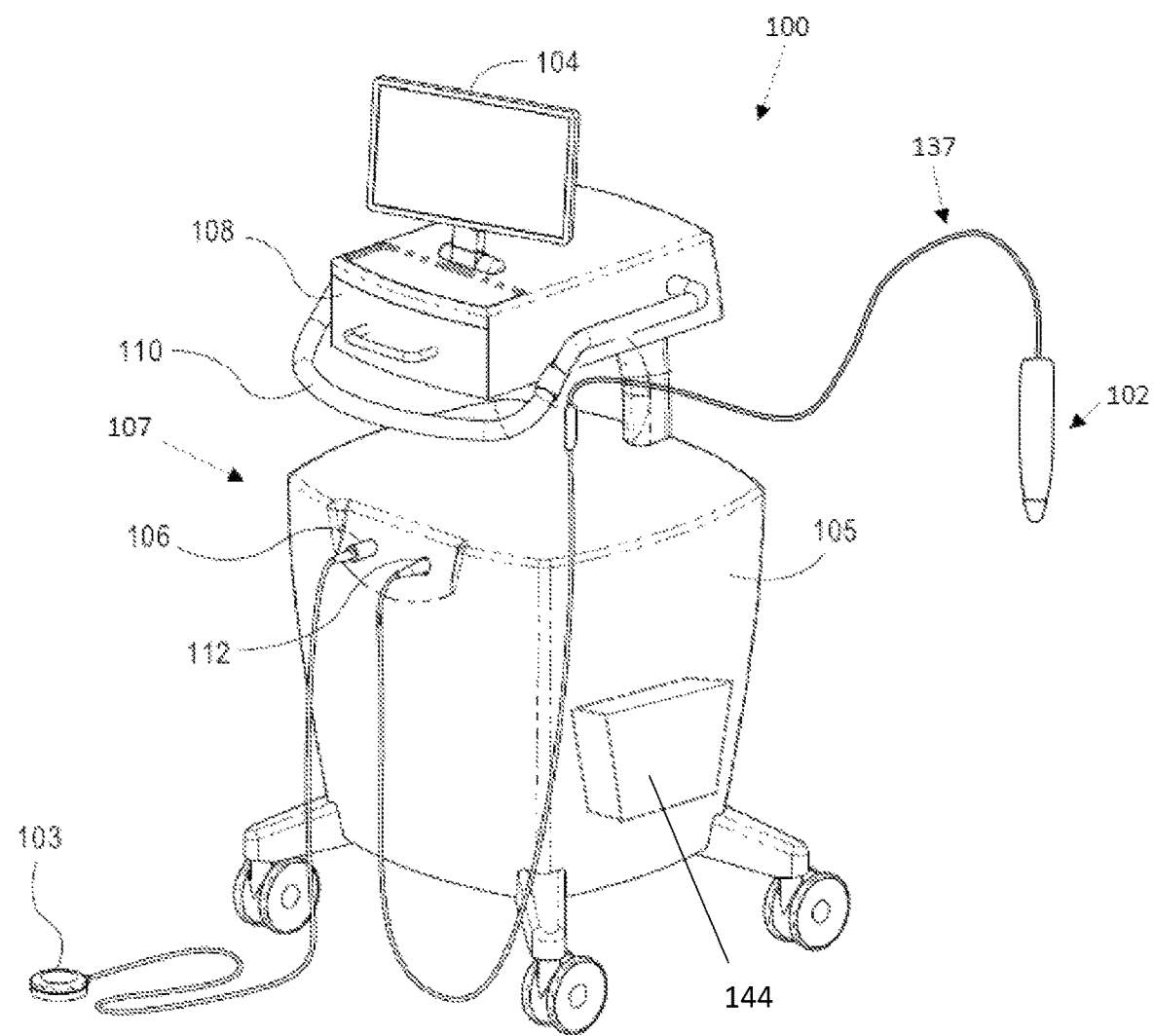
FIG. 1 illustrates one example of a system, including a treatment applicator as described herein and a pulse generator to which the treatment applicator is coupled, for delivery of high voltage, fast pulsed electrical energy.

For the sake of clarity and conciseness, certain aspects of components or steps of certain embodiments are presented without undue detail where such detail would be apparent to skilled persons in light of the teachings herein and/or where such detail would obfuscate an understanding of more pertinent aspects of the embodiments.

Described herein are apparatuses (e.g., devices, systems, etc. including treatment applicators) adapted to be used for the application of electrical energy into a target tissue.

As used herein a treatment applicator includes one or more electrodes for the application of pulsed electrical energy, and in particular sub-microsecond pulsed electrical energy, to a tissue. A treatment applicator may be equivalently referred to as simply an "applicator" or as an applicator device. The treatment applicators described herein may be configured as a disposable or removable treatment tip. A removable and disposable treatment tip is therefore a subset of treatment applicator that may be attached to and/or removed from a handpiece, including in particular a reusable handpiece. When a disposable/removable treatment tip is coupled to a handpiece, the assembly may be referred to as a treatment applicator assembly. In some examples the treatment applicator includes a treatment tip (treatment tip region) that is integrated into a handpiece.

Any of the treatment applicator described herein may include one or more electrodes or groups of electrodes. An electrode may generally be an electrically conductive portion of the treatment applicator that is configured to contact the tissue to deliver pulsed energy to the tissue. As used herein a group of electrodes may be multiplexed together so that they apply energy together, acting as if they were a single electrode although they contact the tissue at multiple discrete and/or different locations. For example, in some cases the treatment applicator may be configured to apply suction between different electrodes (e.g., needle electrodes, pin electrodes, etc.) and the different electrodes may be multiplexed together (or alternatively may be separately addressable). In some examples the treatment applicator may be configured to apply vacuum between the groups of multiple electrodes (e.g., a first set of electrodes that are multiplexed together and may act as a "positive" electrode and a second set of electrodes that are multiplexed together and may act as a "negative" electrode).

Any appropriate type of electrode may be used, including tissue penetrating (e.g., needle electrodes, knife electrodes, etc.) and non-penetrating electrodes (e.g., surface electrodes, wire electrodes, coil electrodes, etc.).

The treatment applicators described herein may be configured to use suction. In some of the treatment applicators described herein the electrodes may be non-penetrating or tissue-penetrating (e.g., sharp) electrodes that are biased (e.g., spring-loaded) so that they may be displaced slightly by contact with the tissue and may apply a force against the surface of the tissue. Suction may be used to hold the tissue and the electrodes in contact. The treatment applicators described herein may apply electrical treatment (e.g., pulsed, sub-microsecond, including nanosecond, electrical treatment) to the surface of the tissue.

In some examples of the treatment applicators described herein may be adapted to apply electrical treatment in a region of the tissue that is just below (e.g., superficial to) the surface of the tissue. For example, described herein are treatment applicators that include a suction chamber with one or more electrodes, including but not limited to tissue-penetrating electrodes that may extend transversely into the tissue. In some examples the treatment applicators described herein include a suction chamber with one or more non-penetrating electrodes that may be held secured against the tissue. In some examples the electrodes may each be independently biased against the tissue.

Any of these apparatuses may include a pulse generator as part of a system including the treatment applicator (e.g., tips, handpiece, etc.). For example, FIG. 1 illustrates one example of a system 100 that may be used with or may incorporate any of the treatment applicators described herein. The system shown in FIG. 1 (also referred to herein as a high voltage system or a sub-microsecond generation system) for delivering high voltage, fast pulses of electrical energy that may include an elongate treatment applicator tool 102, a pulse generator 107, footswitch 103, and user interface 104. Footswitch 103 is connected to housing 105 (which may enclose the electronic components) through a cable and connector 106. The treatment applicator 102 may include electrodes (e.g., as part of an electrode tip) and may be connected to housing 105 and the electronic components therein through a cable 137 and high voltage connector 112. Examples of treatment applicators are described in greater detail below. The high voltage system 100 may also include a handle 110 and storage drawer 108. The system 100 may also include a holder (e.g., holster, carrier, etc.) (not shown) which may be configured to hold the treatment applicator 102.

In some cases, the treatment applicator comprises a disposable treatment tip that may releasably couple to the handpiece of the treatment applicator. In some variations the treatment tip may be adapted to make an electrical, mechanical and a pressure connection, as will be described in greater detail below. In some examples the system may include, or may be configured to operate with, a source of negative pressure (e.g., suction, vacuum, etc.). In some examples the handpiece of the treatment applicator may include a self-contained source for generating suction that may be used to apply suction at the tip.

A human operator may select a number of pulses, an amplitude, a pulse duration, and/or frequency information, for example by inputting such parameters into a numeric keypad or a touch screen of interface 104. In some embodiments, the pulse width can be varied. A controller 144 (e.g., microcontroller) may send signals to pulse control elements within system 100. In FIG. 1, the controller (which may include one or more processors and other control circuitry, including memory) is shown within the housing 105, but it may be positioned anywhere in the system. The controller may be coupled to the pulse generator and/or power supply and may receive input from any of the input components. One or more processors (not shown) may be a separate processing unit or may be incorporated with the controller. The controller may comprise a plurality of controllers and the processor may comprise a plurality of processors. In some embodiments, fiber optic cables are used which allow control signaling while also electrically isolating the contents of the metal cabinet with sub-microsecond pulse generation system 100, e.g., the high voltage circuit, from the outside. In order to further electrically isolate the system, system 100 may be battery powered instead of being powered from a wall outlet.

The elongate treatment applicator tool may be hand-held (e.g., by a user) or it can be affixed to a movable arm of a robotic system, and its operation may be at least partially automated or fully automated, including computer controlled. In some implementations, a solenoid (not shown) may be used for deployment and/or retraction of the electrodes of the treatment applicator. For example, a foot pedal, a button or any other control mechanism may be used, for example, to apply current to the solenoid, which may force electrodes to deploy and/or to retract. Any other appropriate types of actuator devices may be used instead of the solenoid. The solenoid may be used in conjunction with a bias (e.g., spring). For example, any of these apparatuses may include a biased solenoid to deploy the electrodes, such as tissue penetrating electrodes, into the tissue when power is applied to the solenoid. When the user activates the solenoid, the electrode(s) may be driven into the tissue; driving the electrodes into the tissue may also apply load to the bias. Once the power to the solenoid is released (e.g., after applying the treatment) the power to the solenoid may be released, and the bias may withdraw the electrode(s) out of the tissue. Alternatively, the solenoid may be configured to withdraw the one or more electrodes and the bias may be configured to deploy the electrode(s) out of the tissue (loading the bias).

As mentioned, the methods and apparatuses described herein include treatment applicators that include one or more sets of electrodes for applying electrical energy to a tissue. The treatment applicator may include a tip portion and a handpiece portion. The tip and handpiece may be separate, or they may be a single, unitary treatment applicator. In some examples the tip is removable from the handpiece so that the multiple different tips, including different types of tips, can be coupled to the handpiece. The handpiece and/or the tip may include a source of negative pressure (e.g., suction or vacuum) that may be applied through the electrode in order to modify the contact between the tip, and in particular the electrode(s) of the tip, and the tissue. In particular, the handpiece may include a self-contained source of vacuum.

In any of the methods and apparatuses described herein suction may be controlled by one or more controls on the tip and/or handpiece portion of the treatment applicator. In some examples suction may be manually controlled by a user-activated bleed valve. When the valve is open, suction is drawn through the valve, and very little suction may be applied at the tissue-contacting region of the tip; however, closing or occluding the bleed valve, e.g., covering the bleed valve with a finger or hand, may increase suction through the suction port(s) at the tip.

Surface Treatment Applicators

A treatment applicator as described herein may be configured for delivery of electrical treatment or therapy to a surface of a tissue. These treatment applicators may include either penetrating electrodes or non-penetrating electrodes, or both. In some examples the treatment applicators of the present disclosure may include: an electrode housing extending from a distal end of a treatment tip, and one or more (e.g., a plurality) of suction ports opening into the electrode housing. In general, these treatment applicators may include a plurality of non-penetrating electrodes that extend from the electrode housing. The non-penetrating electrodes are configured not to penetrate the tissue and extend out of the treatment applicator housing. In some examples the electrodes extend out of suction ports of the electrode housing. In some examples the electrodes extend adjacent to one or more suction ports of the electrode housing; for example, the electrodes, or sets of electrodes may extend from an opening in the electrode housing that is adjacent to one or more (including surrounded by or partially surrounded by) suction ports. The non-penetrating electrodes may extend away from the treatment applicator distal face in an extended configuration. The non-penetrating electrodes may be configured to retract into the electrode housing when driven against the tissue, e.g., may be spring-loaded. For example, the non-penetrating electrodes may be connected to (or may include) a bias that pushes against the tissue when driven against the tissue to restore the non-penetrating electrode to the extended configuration. Examples of the non-penetrating electrodes may include surface or plate electrodes, blunt needle electrodes, cylindrical electrodes, wire, bar, coil, or blunt pin or bunt needle electrodes.

Figure 2A:
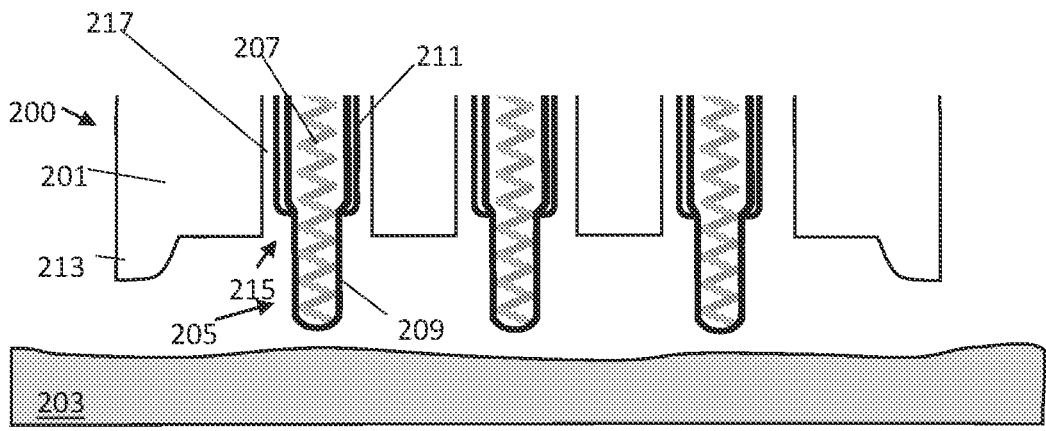
FIGS. 2A-2C illustrate the operation of one example of a treatment applicator including a tip region that includes spring-loaded non-penetrating electrodes that are biased to retract when driven against a tissue.

An example of a treatment applicator including a plurality of spring-loaded electrodes with suction ports is shown in FIG. 2A. In this example, the treatment applicator 200 is shown in section above a target tissue 203. The treatment applicator includes three spring-loaded, non-penetrating electrodes 205. Each electrode in this example is configured similar to a pogo pin, in which an internal bias (e.g., coil spring) 207 is held within the electrically conductive (e.g., gold-coated) pin body 209; the spring may be electrically insulated from the conductive body of the electrode. In this example, an outer body 211 is held fixed within the electrode housing 201, while the pin body 209 may be retracted when driven against the tissue, as shown in FIG. 2B.

Figure 2B:
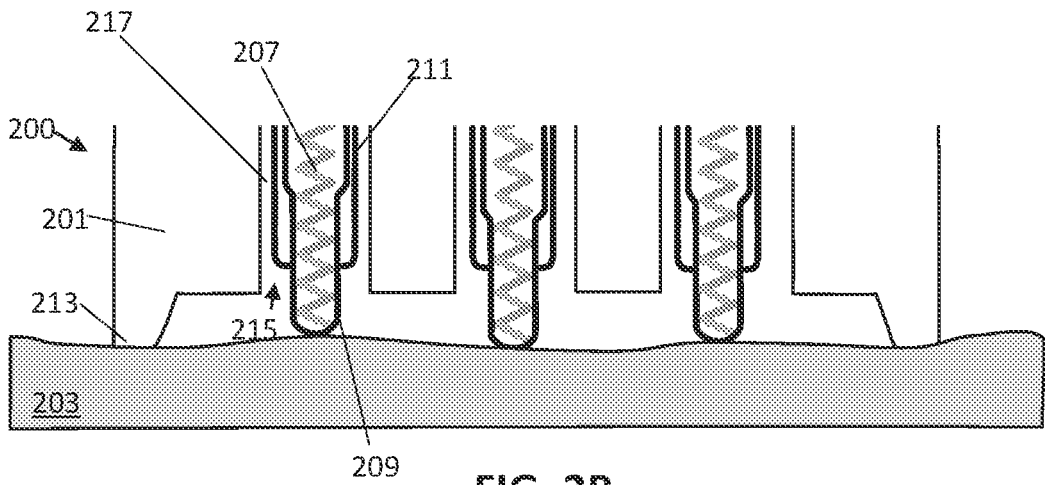
Figure 2C:
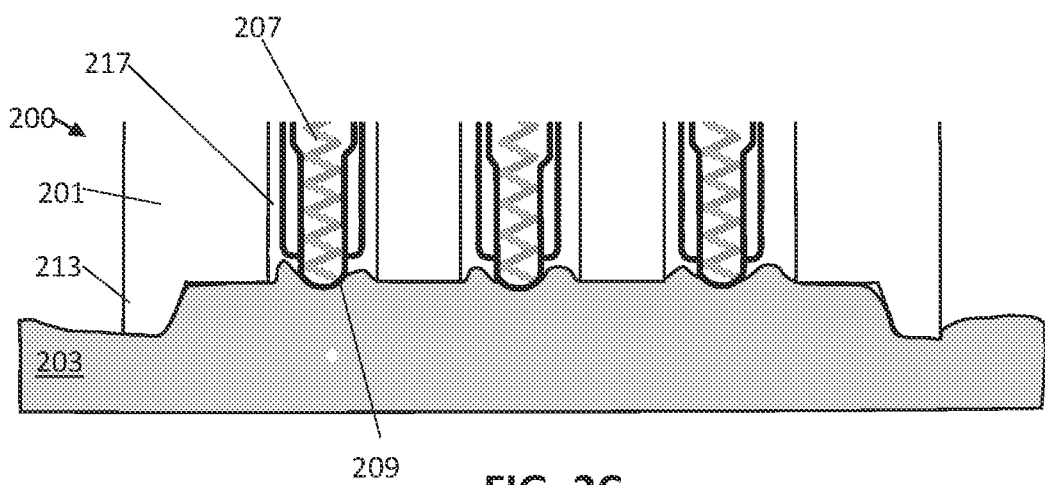

As shown in FIG. 2B, the distal face of the treatment applicator (e.g., the treatment tip) may be pressed against the tissue (e.g., skin) surface. The non-penetrating electrodes in this example are shown as rounded and relatively large diameter, so as not to penetrate the tissue. In some examples they may be dull and/or flat. The treatment applicator also includes a seal 213 around all or some of the electrodes. In FIGS. 2A-2C the seal is formed of a flange or rim that may be formed of a silicone material surrounding the electrodes. The seal may press against the skin. In FIG. 2B, as the device contacts the skin surface, each of the electrodes is individually (and independently) displaced proximally.

A negative pressure (e.g., vacuum, suction, etc.) may be applied thorough one or more suction ports 215 that are fluidly connected with a source of negative pressure through a suction channel 217. In some examples, the suction may be applied prior to contact with the tissue. Alternatively, in some examples, suction may be applied after contacting the tissue, and may be triggered by displacing one or more of the electrodes. FIG. 2C illustrates the tip shown in contact with the tissue, in which the tissue is pulled up and held in contact with each electrode by the combination of the suction applied through the suction ports and the force of the bias driving the electrodes against the tissue.

Any of the examples, including those of FIGS. 3A-3B, 4A-4B, 5A-5C, 6A-6C, 7A-7C, 8, 9, 10A-10F, 11A-11E, 12A-12C and 14A-14B may be implemented as treatment tips, similar to those described above, having non-penetrating electrodes that are biased (e.g., spring loaded) to apply force against the tissue in conjunction with suction.

For example, FIGS. 3A-3B illustrate a first example of a treatment tip including retractable non-penetrating electrodes for applying energy to a surface of a tissue. In FIGS. 3A-3B the treatment applicator 300 includes an electrode housing 301 that (in this example) also extends from a treatment applicator housing 302. In this example, four non-penetrating electrodes 305 are included in the tip, and each of these four electrodes is individually biased so that they may retract slightly when driven against the tissue. For example, each electrode may be internally biased (as shown in FIG. 2A-2C, above). Each electrode may extend from out of a suction port 315 (multiple electrodes may extend from the same suction port, as shown). Since in this example the electrodes are blunt smooth pins, they are less likely to arc and they do not require a protective retractable configuration of the needle housing to shield against unintentional poking.

FIGS. 4A-4B illustrate another example of a treatment tip 400 including an array (4x2) of non-penetrating electrodes 405 that are spring-loaded to retract into the 401 electrode housing similar to that described in FIGS. 2A-2C and 3A-4B, above. The electrode housing may be entirely or partially (e.g., an outer coating) electrically insulated, and/or formed of a soft or deformable material. The array of non-penetrating electrodes shown in FIGS. 4A-4B may cover, for example, an approximately 5 mm×5 mm square. The electrodes in this example may extend out of a suction port; each electrode may be surrounded by the suction port, or each of the two sets of electrodes may extend out of the same suction port 415.

Figure 5A:
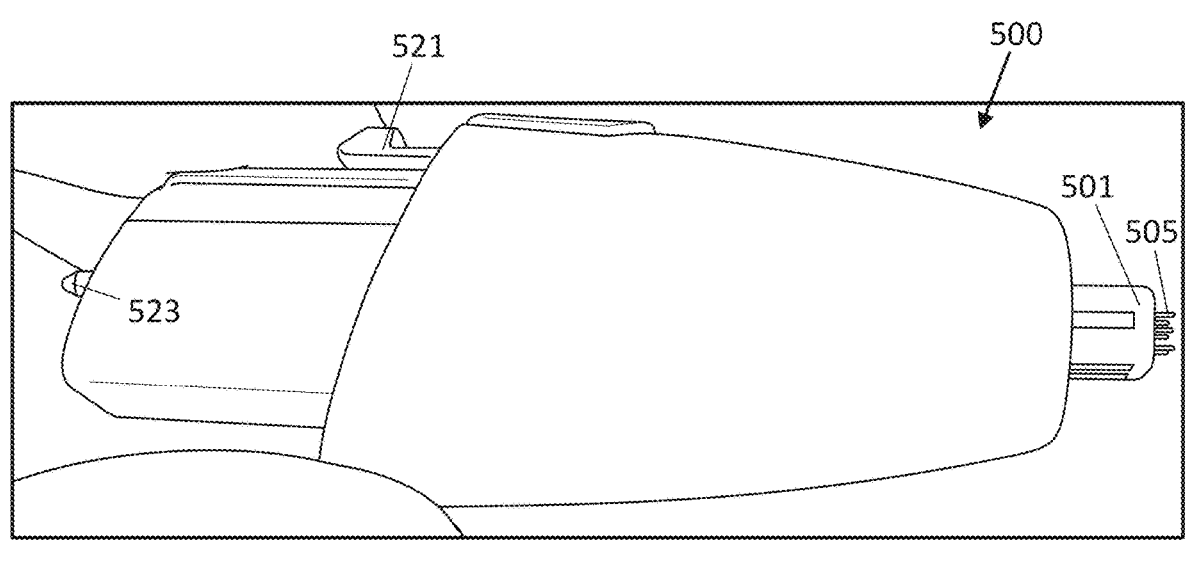
FIGS. 5A-5C illustrate another example of a treatment applicator as described herein.
Figure 5B:
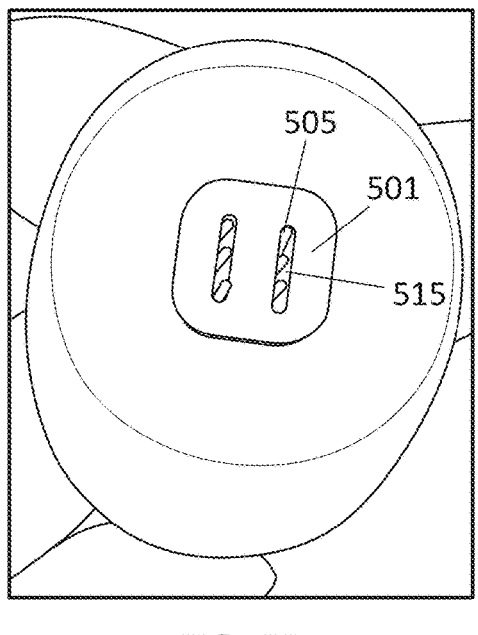
Figure 5C:
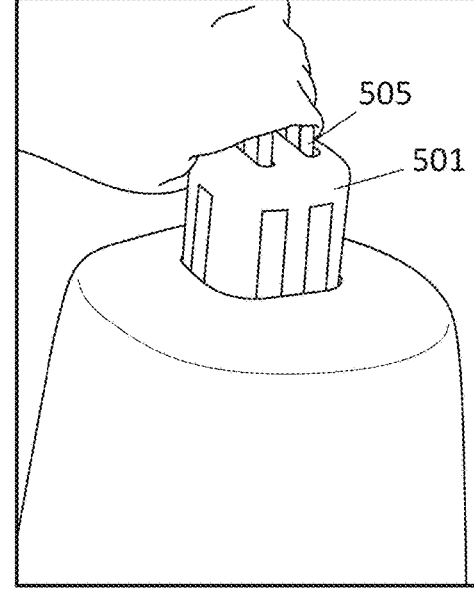

FIGS. 5A-5C illustrate another example of a treatment tip 500 including non-penetrating electrodes for delivering surface treatment. These electrodes 505 are each configured as described above, (e.g., spring-loaded retractable POGO pin type electrodes). The spring-loaded retractable electrodes may make contact and apply pressure to the tissue surface. The outer face of the electrode housing 501 may be made with a soft (e.g., low durometer) material that may help seal the tip to the tissue during treatment. In any of these examples the distal face of the electrode housing may include a seal configured to seal against the tissue when a vacuum is applied. The seal may separately encircle each electrode or set of electrodes, or it may encircle all of the electrodes (e.g., the distal end face of the treatment tip). The suction may be applied out of a suction port 515. In the example shown in FIGS. 5A-5C each of the two sets of electrodes extends out of a suction port 515 so that suction may be applied around the electrodes.

The smooth, round tips of the non-penetrating electrodes may be less likely to arc between the tips than electrodes having sharp points. As shown in FIG. 5A, the treatment tip may be configured to removably attach to a handpiece (not shown). In FIG. 5A, the tip includes one or more electrical connectors 523 at the proximal end that may engage a connector on the handpiece. The tip in this example also includes a mechanical connector and release 521 that may be used to reliably connect the tip to the handpiece.

FIGS. 6A-6C show another example of a treatment tip 600, similar to that shown in FIGS. 5A-5C. In FIG. 6A-6C electrodes 605 extend out of the electrode housing 601 in an array of 3 rows of 4 electrodes. As shown above, each electrode may be separately and independently biased. In some examples, groups of electrodes may be biased together (all or some, such as each row of electrodes, etc.). In the example shown in FIGS. 6A-6C each electrode extends out of (and is surrounded by) a suction port 615.

Any appropriate electrode may be used. For example, FIGS. 7A-7C illustrate an example of a treatment tip 700 having a non-penetrating wire electrode 705. The wire electrode (also referred to herein as a wire loop electrode) is configured as a loop of wire that is attached at either end within the electrode housing 701; one or both ends may be coupled to a bias (e.g., spring) that allows the electrode to be extended out and be pushed (retracted) against the bias force into the electrode housing when driven against the tissue (as illustrated in FIG. 7C). For example, the wire electrodes shown in FIGS. 7A-7C may incorporate internal springs that allow the electrodes to be retractable and function like the POGO style electrodes illustrated in FIGS. 3A-3B and may apply a constant force to tissue during application of the energy. Suction may be applied around the wire loop electrodes.

In FIGS. 7A-7C two wire non-penetrating electrodes are shown. In some examples fewer (e.g., one) or more than two (e.g., 3, 4, 5, etc.) non-penetrating wire electrodes may be included.

Figure 8:
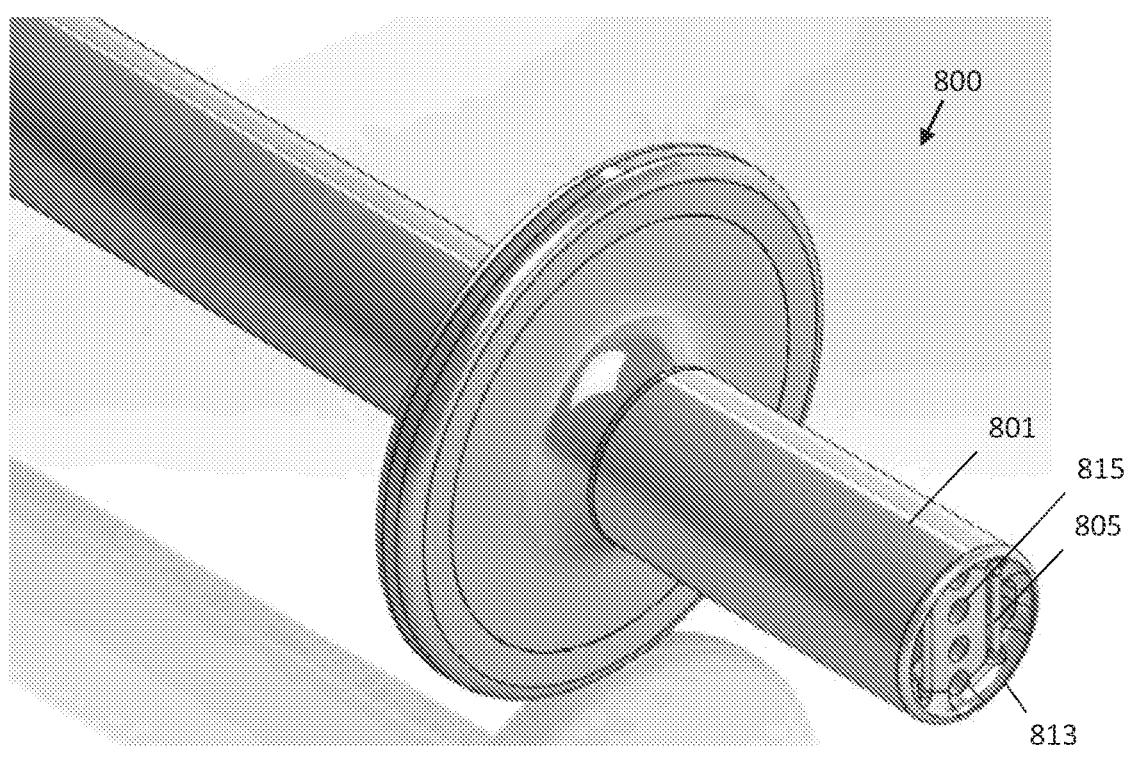
FIG. 8 shows another example of a portion (the distal end portion) of a vacuum-assisted treatment tip including bar or wire non-penetrating electrodes and suction ports.
Figure 9:
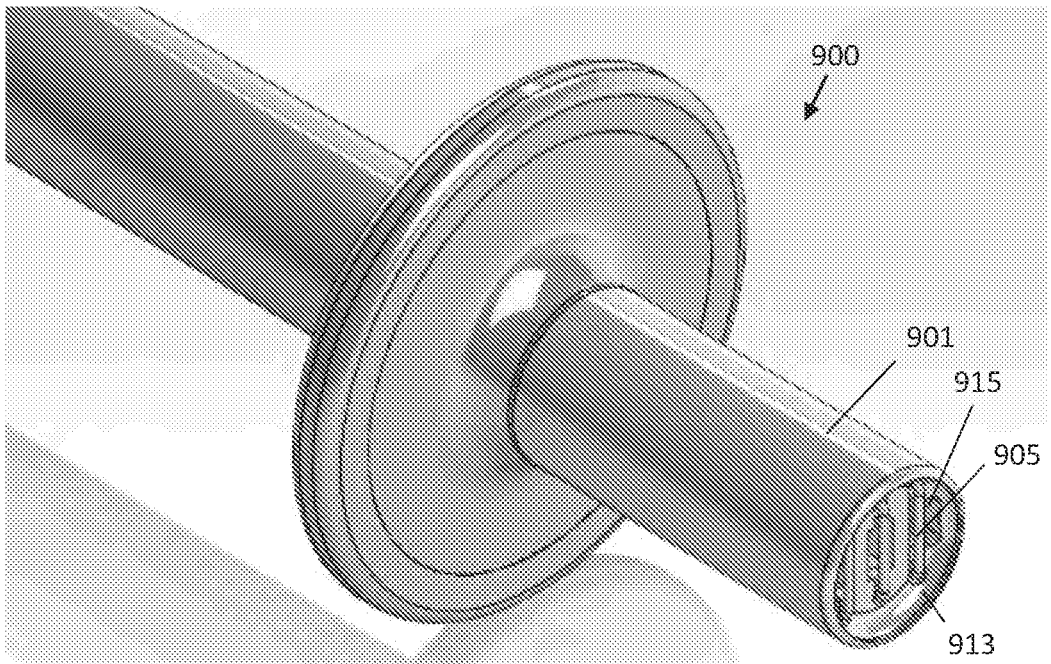
FIG. 9 shows another example of a portion (the distal end portion) of a treatment tip including spring-loaded non-penetrating electrodes and suction ports.

In general, any of these treatment tips may also be configured to apply suction, as described above. For example, suction may be applied to assist with continuous contact with the tissue. FIGS. 8 and 9 illustrate examples of tips (with the treatment applicator housing removed) including multiple suction ports and sealing rings. FIGS. 8 and 9 each illustrate treatment tips with wire (or "bar") electrodes in which the distal face of the treatment tip includes a sealing region (seal) around the electrodes and the suction ports. Although these examples show a single seal, in some examples multiple and/or different seals may be used around sub-sets of the electrodes and suction ports.

In FIG. 8, the treatment tip 800 includes a soft silicone material forming the seal 813 on the electrode housing 801 that may form a suction-cup like structure for securing to the tissue. Two wire (e.g., bar) electrodes 805 are included and a plurality of suction ports 815 including one or more suction ports beneath the length of the wire electrode is shown parallel with the distal face. The multiple suction ports may assist in removing air gaps between the electrodes and the tissue to make a better connection with the tissue and reduce or avoid arcing. In FIG. 8 the suction chamber is formed by the seal 813 (e.g., the lip of the seal), into which tissue (e.g., skin) may be drawn by applying negative pressure (suction).

As mentioned, in some variations the suction from the tip may be controlled by one or more suction controls that the user may manipulate. In some examples the suction control may include a bleed valve. For example, when the suction is turned on, and the bleed valve (suction control) is open, the suction ports 815 may provide only minimal (or no) suction. However, the user may occlude the bleed valve with a finger or hand (or it may be otherwise closed), causing suction to be preferentially applied from the suction port(s) 815 in the tip. In some examples, the application of suction may draw the tissue into contact with the electrode(s). Suction may be released by releasing or uncovering the bleed valve.

The example treatment tip 900 shown in FIG. 9 is similar to that shown in FIG. 8, including the electrode housing 901 and a soft, silicone seal 913 formed around the distal face of the treatment tip encircling the wire electrodes 905 and the suction ports 915. As in FIG. 8, the seal forms a suction chamber. In FIG. 9, three bar electrodes are shown, rather than the two shown in FIG. 8. In some examples the tip may be configured to include both anode and cathode electrodes or may be monopolar and a return electrode (e.g., a grounding pad) may be used. For example, the middle electrode may be the anode while the two outer electrodes are cathodes.

Figures 10A, 10B, 10C, 10D, 10E, 10F:
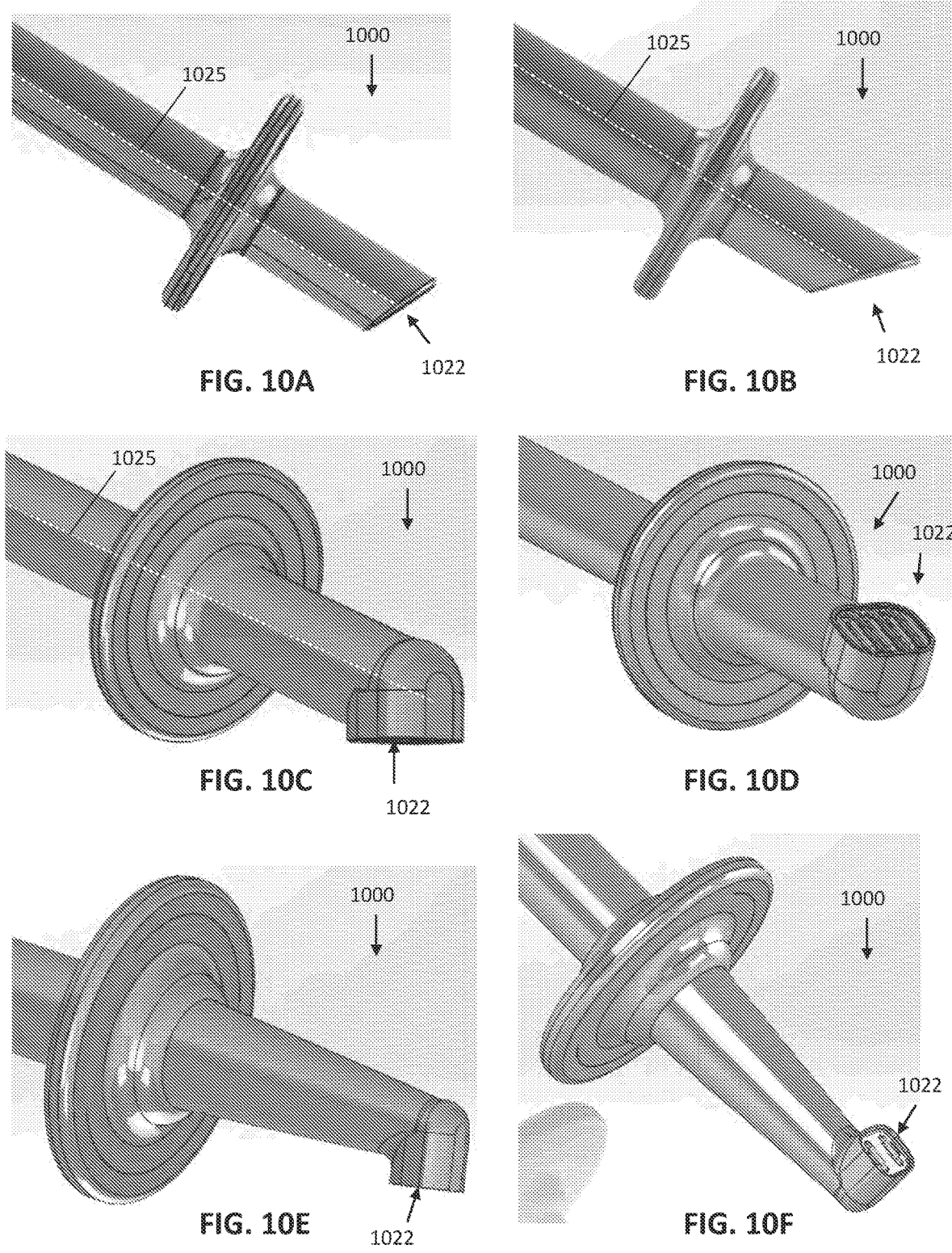
FIGS. 10A-10F illustrate examples of treatment applicators (e.g., shown as treatment tips) having differently angled distal faces, for making contact with the tissue to help with accessibility and visibility of difficult to reach target areas.

FIGS. 10A-10F illustrate examples of treatment tips 1000 that include bent or angled distal faces on which the non-penetrating electrodes and suction port(s) are arranged. The angled faces of the distal tips may help with accessibility and visibility for some lesions (particularly difficult to reach lesions), and the electrode tips can be configured with various angles for the treatment tips. For example, FIG. 10A shows an example of a distal tip in which the bent or angled distal face 1022 is angled approximately 20 degrees relative to the perpendicular face shown in FIGS. 8 and 9 (e.g., 80 degrees relative to the long axis 1025 of the tip). Similarly, FIG. 10B shows a treatment tip 1000 in which the distal face 1022 of the tip is angled approximately 45 degrees relative to the long axis 1025. In FIGS. 10C and 10D the distal face 1022 is angled by approximately 70 degrees relative to the perpendicular face (e.g., 20 degrees relative to the long axis 1025 of the treatment tip). Finally, in FIGS. 10E and 10F, the distal face 1022 of the treatment tip 1000 is parallel to the long axis of the treatment tip, (and angled approximately 90 degrees relative to a perpendicular face of the treatment tip).

Various configurations of non-penetrating electrodes, such as wire (e.g., bar) electrodes, pin electrodes, etc. may be used with suction ports and may include multiple rows and/or multiple poles (e.g., configured as anode/cathode pairs). For example, FIGS. 11A-12C illustrate another example of a treatment tip 1100 having a plurality of non-penetrating electrodes formed as elongate wires. For example, the non-penetrating wire (or bars) electrodes 1105 may be used with suction through one or more suction ports 1115 in larger surface electrodes that may include multiple rows and/or multiple poles extending from the electrode housing 1101, as shown. The dimensions may be, for example, between 10-30 mm (e.g., forming a 25 mm×25 mm square, 30 mm×30 mm square, or any rectangular configuration, etc.). The spring-loaded electrodes described herein may be particularly helpful for larger sized arrays, because the individually biased electrodes may more easily adjust to variations in the depth or height of the tissue surface, which may be curved and/or irregular.

Figure 11A:
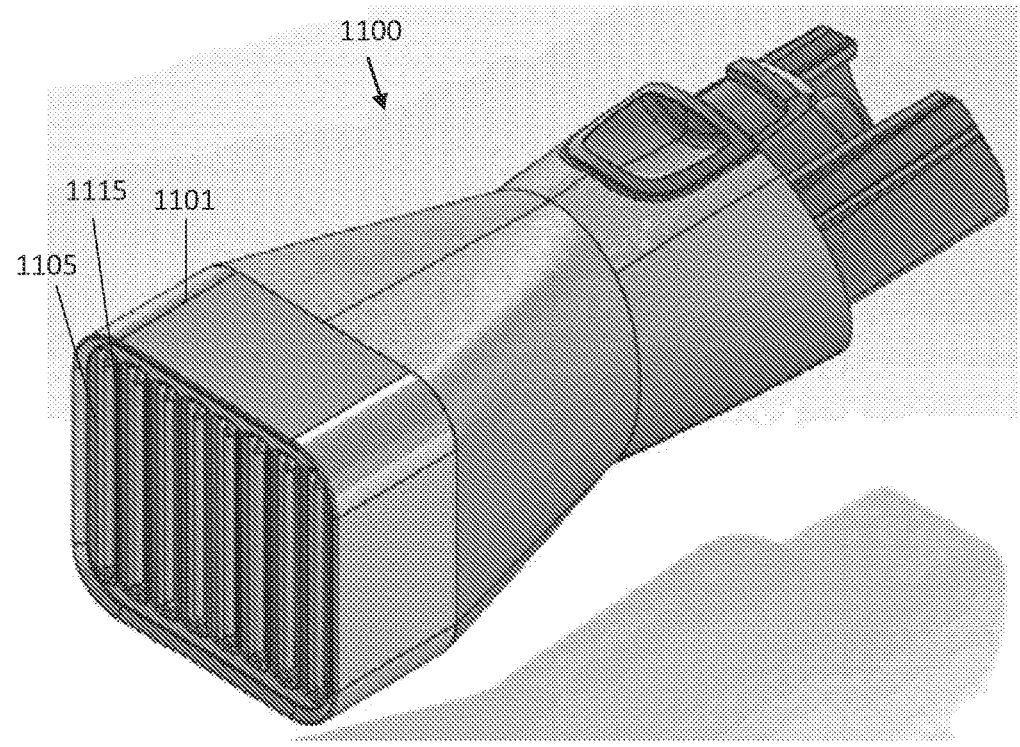
FIGS. 11A-11C show another example of a treatment applicator, configured as a treatment tip as described herein, having surface electrodes (that may be spring-biased) arranged in a relatively large array, and including multiple suction ports.
Figure 11B:
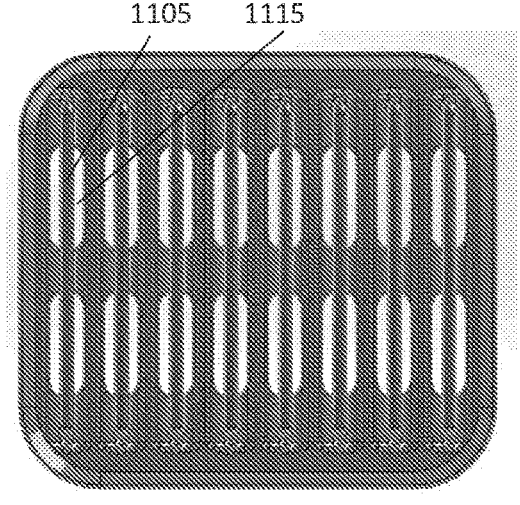
Figure 11C:
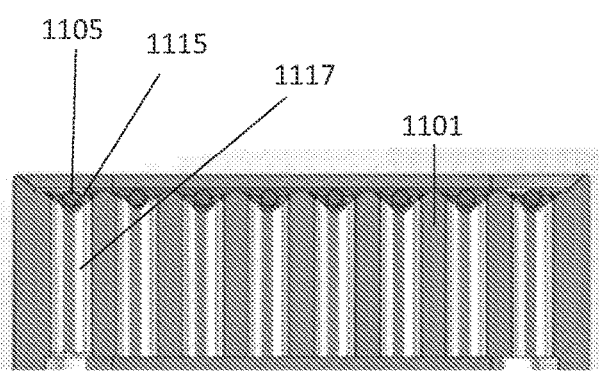

As shown in FIG. 11B, vacuum or suction applied through multiple suction ports 1115 under and/or around the wires or bars electrodes 1105 may help remove any air gaps making a better electrical connection between the electrodes and the tissue. FIG. 11C shows a sectional view through the distal tip region of the treatment tip, showing the suction channels 1117 formed through the electrode housing. The suction channels may be continuous with the suction ports 1115 and source of negative pressure.

Figure 12A:
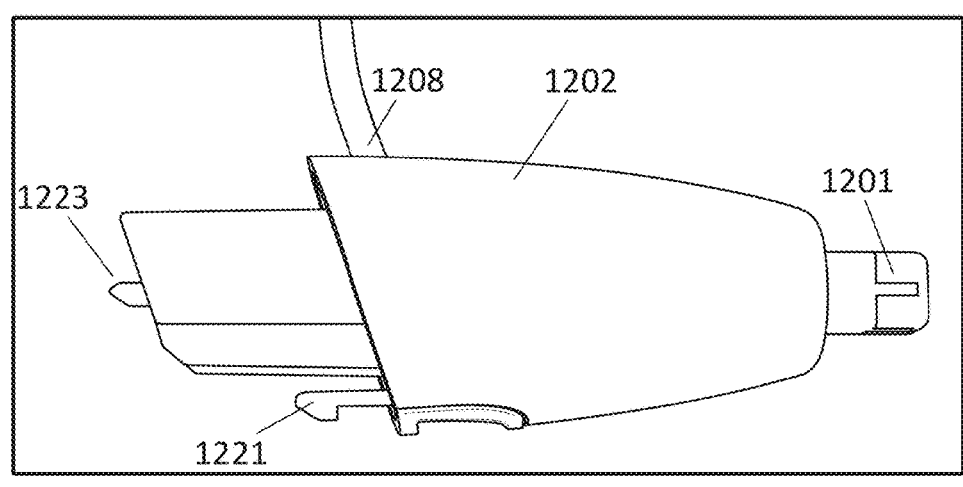
FIGS. 12A-12E illustrate different examples of treatment tips having wire or bar electrodes.
Figure 12B:
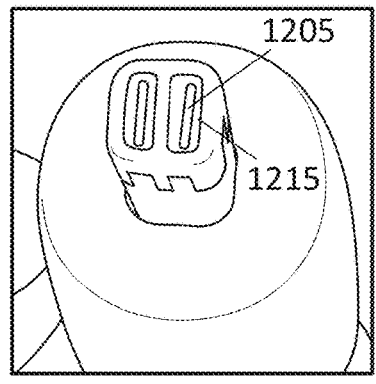
Figure 12C:
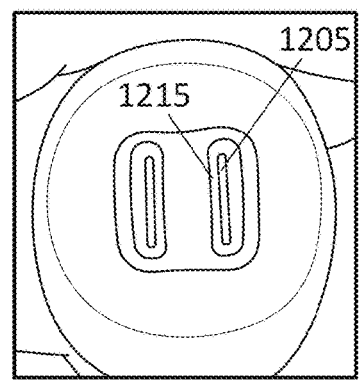
Figure 12D:
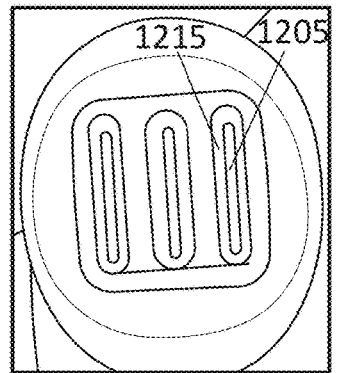
Figure 12E:
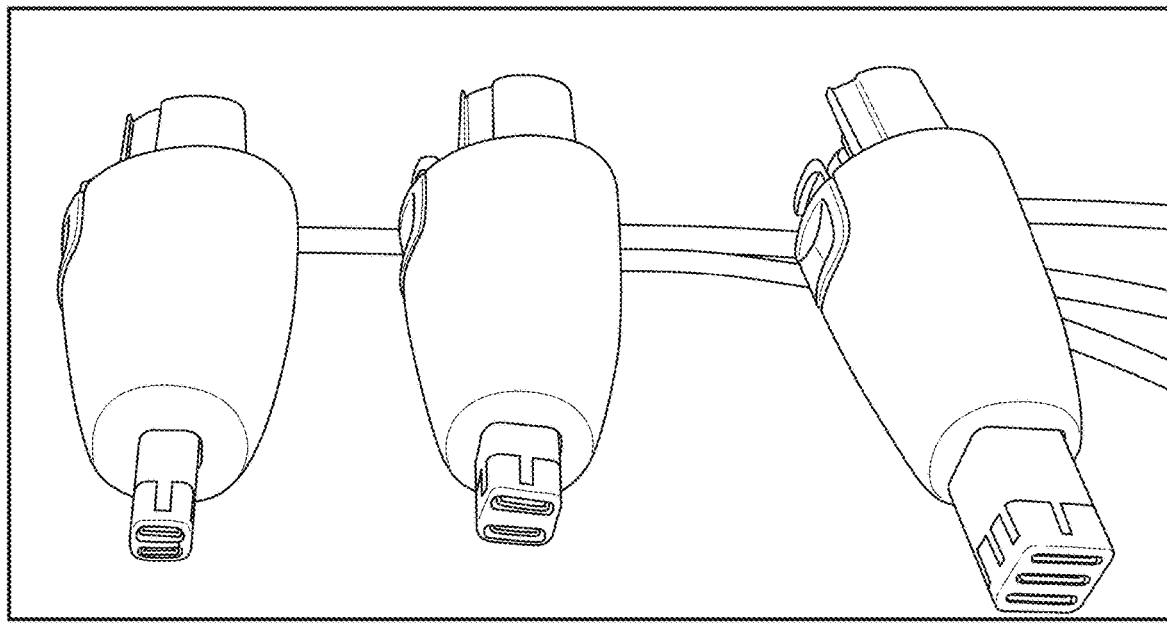

In any of these treatment tips of the present disclosure suction may be applied to assist the tissue in contacting the electrodes. Thus, the suction may be applied after contacting the tissue or before contacting the tissue. In some examples, the suction may be applied just during the period immediately before and during the application of the energy from the electrodes. FIGS. 12A-12E illustrate other examples of suction ports configuration that is especially beneficial in reducing arcing as explained below. FIGS. 12B-12C demonstrate three different sizes of treatment tips, each with non-penetrating electrodes and suction configured according to one or more aspects of the present disclosure. FIG. 12A shows a side perspective view of a treatment tip, showing a connection to a suction line (e.g., source of negative pressure) 1208 extending out of the treatment applicator body (e.g., treatment applicator housing 1202). An electrical connector 1223 extends from the proximal end of the tip, and a mechanical connector (release 1221) may releasably couple the tip to a handpiece. The distal end of the treatment tip includes the electrode housing 1201 from which a plurality of non-penetrating (e.g., spring loaded) electrodes extend. FIGS. 12B-12D shows different dimensions of tips, each shown with wire or bar electrodes that are biased to extend out and may retract when contacting the tissue, as described above. In this example, each of the tips in FIGS. 12B-12E includes suction ports 1215 around the electrodes 1205 each configured as a continuous channel that is extending longer than its respective electrode 1205 visible within the channel or port 1215. The individual suction ports may include individual seals around the electrodes. In the example of FIGS. 12A-12E, each electrode may be individually sealed to the tissue by a seal formed on the tip around each electrode and suction port(s). FIG. 12E shows examples of differently sized tips but all with similarly configured suction ports that extend beyond the electrodes far enough to reduce/avoid arcing; each of these tips may be used with the same handpiece to form the complete treatment applicator. This novel configuration of the suction port where it is located between the electrodes and extends beyond the two ends of each electrode may be incorporated into any of the examples and figures of the present disclosure, including, without limitation, in the design of the treatment applicators of FIGS. 13A-13B and 14A14C below.

In any of the apparatuses and methods described herein suction may be applied continuously, but may not be activated at the tip until the suction control, which may include a bleed valve is activated, focusing the suction to the one or more suction ports in the tip. Suction may be provided from a pump (vacuum pump, suction pump, etc.), or it may be provided from a suction chamber or other device, such as a syringe.

Figure 13A:
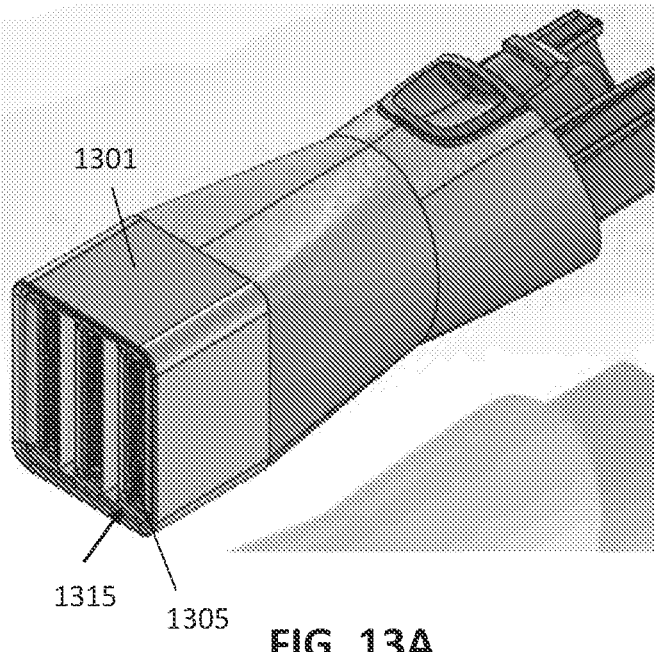
FIGS. 13A-13B illustrate another example of a treatment tip including a plurality of non-penetrating electrodes, configured as coil electrodes.
Figure 13B:
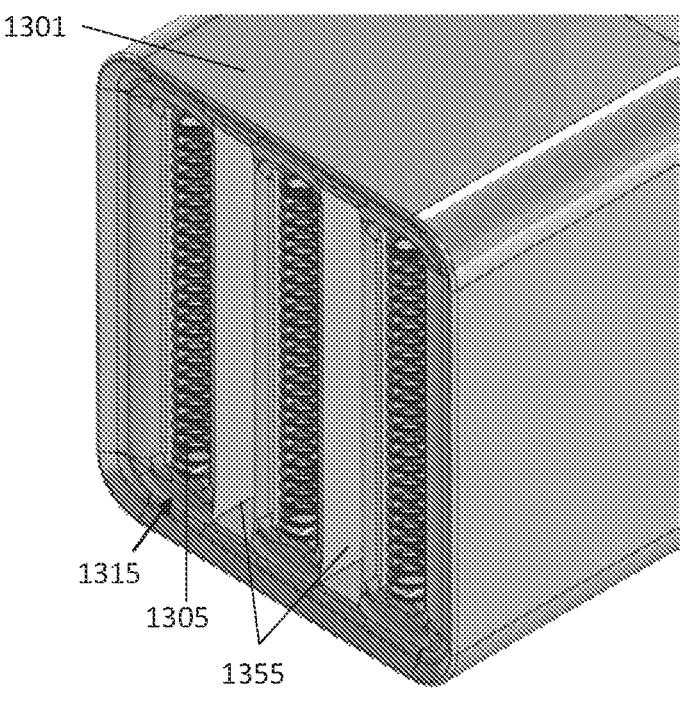

FIGS. 13A-13B illustrate another example of a treatment tip 1300 similar to that shown in FIGS. 12A-12B but with a spring or coil electrode as the non-penetrating electrode 1305. This electrode also extends from the housing 1301 and may be biased to be spring-loaded (e.g., may be biased to extend from the electrode housing and can be pushed back into the housing by the force of contacting the tissue. The suction port 1315 may be used to draw tissue against the non-penetrating electrode. FIG. 13B shows an enlarged view of the distal end of the treatment tip shown in FIG. 13B. The non-penetrating (spring) electrodes are each within a suction chamber that is bounded on its sides, but open on the top to allow tissue to be drawn into the suction chamber. In one example the two suction ports 1355 are positioned between the three electrodes shown. Alternatively or additionally, in some examples a vacuum may underlie each of the non-penetrating electrodes.

In the treatment applicator shown in FIGS. 13A-13B the electrodes are separated by a continuous suction port 1355 that may extend further than the length of each electrode, which may reduce or prevent arcing. As will be described in greater detail below in reference to FIGS. 15A-15D through 19A-19D, the shortest distance between the electrodes (or sets of electrodes) that goes around the continuous suction barrier between the electrodes (or sets of electrodes) may be 5% or greater (e.g., 10% or greater, 12% or greater, 15% or greater, 17% or greater, 20% or greater, 25% or greater, 30% or greater, etc.) than the minimum distance between the electrodes (or set of electrodes) ignoring the continuous suction barrier. The shortest distance between the electrodes (or sets of electrodes) that goes around the continuous suction barrier between the electrodes may be referred to as the strike distance.

Figure 14A:
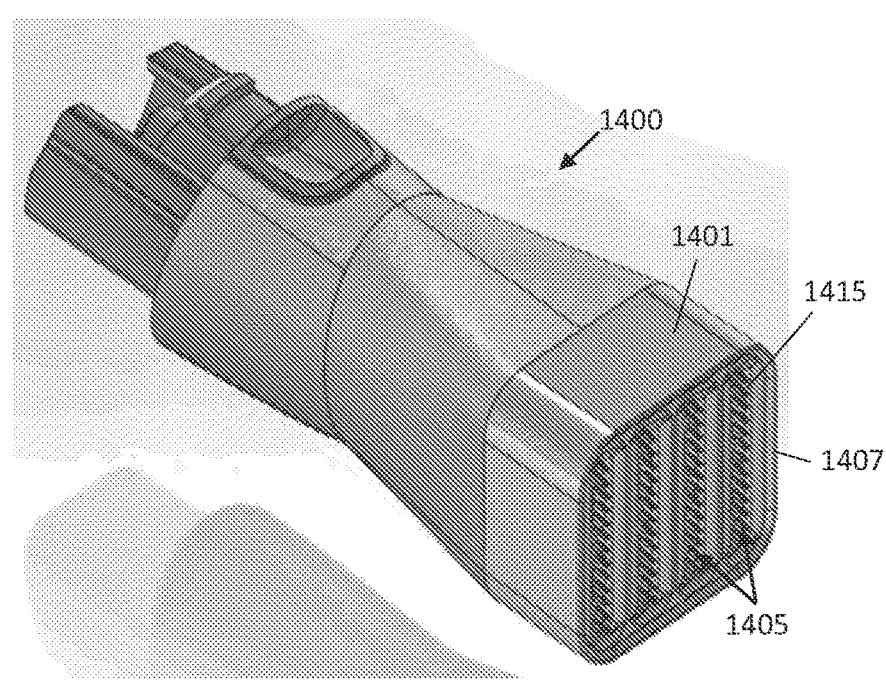
FIGS. 14A-14C show an example of a treatment tip including a plurality of electrodes, configured as elongate electrodes (which may be tissue penetrating or non-penetrating). Suction may be applied within the distal end chamber of the tip and the electrode may contact the tissue that is drawn into the tip.
Figure 14B:
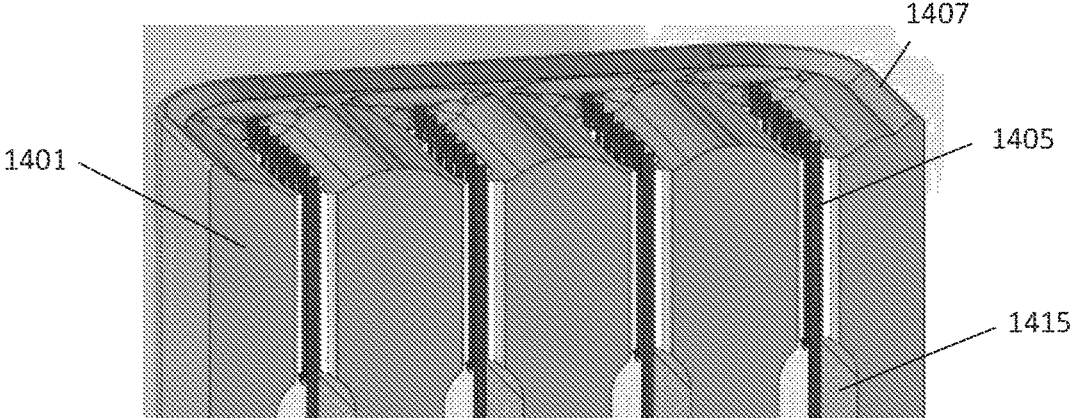
Figure 14C:
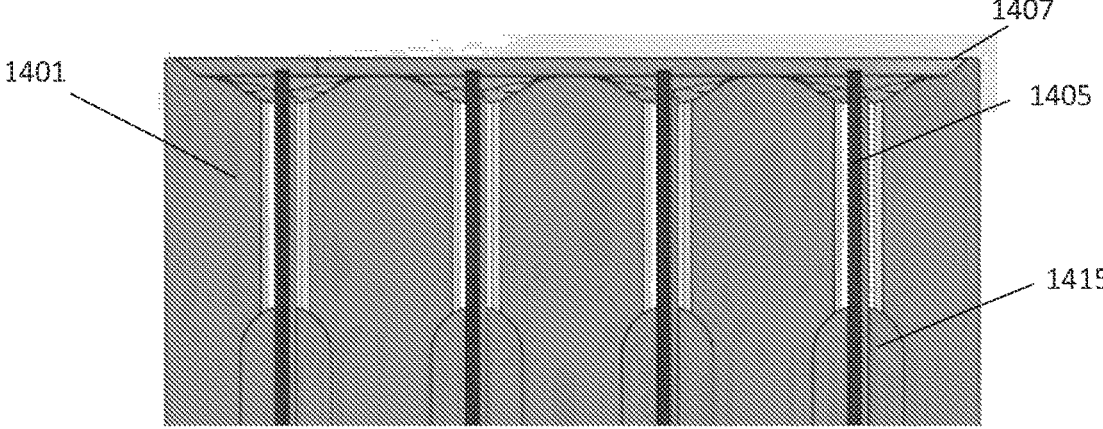

FIGS. 14A-14C illustrate another example of a treatment tip, which may be configured with penetrating or non-penetrating electrodes. In FIG. 14A the treatment tip 1400 includes a mechanical and electrical attachment (for attaching to a handpiece, not shown) and includes four rows of elongate electrodes 1405 extending into the electrode housing 1401. Each row in this example comprises a set of electrodes. The individual electrodes in each set may be electrically coupled, or they may be individually addressable. In FIGS. 14A-14C the sets of electrodes are each shown extending from a suction port 1415. Four suction ports are shown in FIG. 14A. The entire distal tip region of the electrode housing may form a suction chamber, and the outer perimeter 1407 may form a seal, so that tissue may be drawn into the suction chamber when suction is applied.

In any of the examples described herein the electrodes may be tissue-penetrating. For example, in FIGS. 14A-14C, the electrodes may be tissue-penetrating, needle electrodes. The suction ports 1415 are shown located around and under the set of needle electrodes of each row. Each suction port may surround all of the electrodes of its respective row and extend to be at least slightly longer than the row to achieve the benefit as discussed in reference to FIG. 12. In this example, the needle may be secured in position relative to the tip, so that when the suction is applied, the needles are inserted into the tissue as the tissue is pulled into the vacuum cavities. Alternatively or additionally, in some examples, the needles may be extendable/retractable. In some examples the needles may be individually biased and/or individually extendable or retractable.

In the example treatment applicator shown in FIGS. 14A-14C each of the electrodes (or in this example, sets of electrodes) of the pairs of electrodes that are activated to deliver the treatment are surrounded by suction. This may reduce arcing between the pairs of electrodes (or pairs of sets of electrodes). Alternatively, a continuous suction barrier may be applied between the electrodes or sets of electrodes of the pairs.

Any of the treatment applicators described herein may be configured to prevent or reduce arcing by including a region of continuous suction between the pairs of active electrodes (or pairs of sets of electrodes that are electrically coupled together) that extends between and beyond the length of the electrodes. Thus, the continuous suction barrier region may increase the strike distance between the active electrodes or sets of electrodes. For the voltage ranges commonly used by the methods and apparatuses described herein (e.g., between about 0.1 kV/cm and about 500 kV/cm) treatment applicators described herein may have a strike distance that is 10% (12% or more, 15% or more, 17% or more, 20% or more, 22% or more, 25% or more, 27% or more, 30% or more, etc.) or more than the minimum distance between the electrodes or sets of electrodes (ignoring the continuous suction barrier), where the strike distance is the shortest distance between the electrodes or sets of electrodes around the continuous suction barrier. In practice, the strike distance is the shortest route in which voltage can flash-over or arc from between the electrodes or sets of electrodes. The operating voltage of the tip may change the strike distance (e.g., at higher operating voltages, a greater strike distance may be used). Treatment tips such as those shown in FIGS. 2A-2C, 3A-3B, 4A-4B, 5A-5C, 6A-6C, and 7A-7C, in which each of the electrodes or sets of electrodes for delivery of treatment may be surrounded by suction, which may reduce or eliminate arcing. Alternatively or additionally, a continuous suction port may separate and extend beyond the electrodes or sets of electrodes to prevent or reduce arcing in addition to securing the tissue during the application of energy.

For example, FIGS. 15A-15D, 16A-16D, 17A-17D, 18A-18D and 19A-19D all illustrate examples of a treatment applicators (configured as treatment tips) in which a continuous suction port extends between the sets of electrodes delivering the treatment, instead of (or in addition to) surrounding the electrodes with suction. The continuous suction port may extend between the electrodes (or sets of electrodes) delivering the treatment so that the continuous suction port extends further than the length of the electrodes or sets of electrodes.

FIGS. 15A-15C illustrate another example of a treatment applicator configured as a removable/replaceable treatment tip 1500, including a plurality of tissue-penetrating electrodes 1505, 1505', for example, on either side of a suction port 1515. In this example the suction port 1515 is centrally located within the electrode housing. The first set of electrodes 1505 on the left of the central suction port, includes a plurality of individual needle electrodes that are multiplexed together. The second set of electrodes 1505' on the right side of the suction port are also multiplexed together. For example, the first set of electrodes may act as a cathode and the second set of electrodes may act as the anode. FIG. 15A shows the treatment tip with the needle electrodes retracted into the electrode housing 1501; in FIG. 15B the electrodes 1505, 1505' extended distally out of the electrode housing 1501 on either side of the suction port 1515. The suction port 1515 extends in a continuous line between the sets of electrodes 1505 so that the electrodes (which may be coupled or multiplexed together as mentioned above) forming the anodic electrode are continuously separated from the cathodic electrodes, and beyond the ends of the electrodes or sets of electrodes. The electrode housing is shown extending distally from the applicator housing 1503, and in some examples the electrode housing may retract into the applicator housing; a bias (e.g., spring) may tend to keep the electrode housing extended, but the user may drive the electrodes into the tissue by driving the applicator housing distally when the tissue is retained by the suction on the applicator housing, allowing the electrodes to penetrate into the tissue to the predetermined depth. In this example, the electrodes are each within channels 1518, in two separate sets. The electrodes are separated from the central suction port 1515 by sidewalls 1522, which may seal against tissue when suction is applied. Each electrode in the sets of electrodes may be electrically coupled, so that energy may be applied between the sets of electrodes.

As mentioned, the example shown in FIGS. 15A-15C includes a single suction port 1515 (e.g., vacuum port) between the sets of electrodes; this may help ensure that the tissue contacts the electrode housing. This continuous suction port extending between the electrodes and further than the ends of the electrodes, may also help prevent arcing during use. FIG. 15D illustrates the relative positions of the first set of electrodes, the second set of electrodes and the suction port 1515. In this example, the suction port 1515 forms a continuous suction barrier which increases the strike distance 1557 between the active electrodes or sets of electrodes so that it is 5-10% or more than the minimum distance 1555 between the sets of electrodes ignoring the continuous suction barrier. As mentioned above, the strike distance 1557 is the shortest distance between the electrodes or sets of electrodes around the continuous suction port and is shown as the longer dashed line in FIG. 15D. In these examples the strike distance and the minimum distance without the suction port may be measured along the surface of the electrode housing 1501, as shown in FIG. 15D.

FIGS. 16A-16C illustrate an example of a treatment tip 1600 with dual suction ports 1615 that each forms a continuous suction port between the two sets of electrodes 1605. Each set of electrodes is adjacent to an inner suction port (as indicated by 1622). The two sets of electrodes are each in a channel 1618 in the electrode housing 1601 and the electrode housing extends for the applicator housing 1603. The electrodes in FIG. 16A are shown retracted into the applicator housing; in FIG. 16B the electrodes are shown extended out of the applicator housing. As in FIGS. 15A-15C the electrodes are sharp, tissue-penetrating electrodes.

In FIG. 16C the distal end view of the tip shows that the elongate suction ports 1615 will each draw tissue between the sets of electrodes, preventing arcing, and securing the tissue against the tip so that the electrodes may penetrate into the tissue. As in FIGS. 15A-15C, the suction ports are not connected to the channels (slots) from which the electrodes extend and retract. The suction ports form a continuous suction port (barrier) between the sets of electrodes from which treatment is delivered, and each extends beyond the length of the sets of electrodes.

FIG. 16D illustrates the increase in the strike distance 1657 between the first set of electrodes 1605 and the second set of electrodes 1605' due to the continuous suction barrier 1515, so that the strike distance 1657 is 5% or more (in this example 15% or more) than the minimum distance 1655 between the sets of electrodes ignoring the continuous suction barrier. The strike distance 1657 is shown as the longer dashed line in FIG. 16D and the minimum distance 1655 without the suction port is shown as the shorter solid line, both of which may be measured along the surface of the electrode housing 1601, as shown in FIG. 16D.

Any number of suction ports may be positioned adjacent to (or between) the sets of electrodes. In some examples the suctions port may also be present on the opposite side(s) of the sets of electrodes, and/or around the sets of electrodes. For example, FIGS. 17A-17C illustrate a treatment tip 1700 in which two electrodes (or sets of electrodes) are bordered on two sides by suction ports 1715. In FIGS. 17A-17C, the electrodes are shown as non-penetrating plate electrodes 1705. The suction ports 1715 include a central suction port 1715' that is larger than two side suction ports 1715" and is longer than the length of the electrodes 1705, 1705'. The electrode housing 1701 extends from the applicator housing 1703.

FIG. 17D shows that this variation also include a continuous suction port 1715' between the electrodes 1705, 1705' and extending beyond the lengths of the electrodes so that the strike distance 1757 between the first set of electrodes 1705 and the second set of electrodes 1705' in this example is 10% or more than the minimum distance 1755 between the sets of electrodes ignoring the continuous suction barrier, thereby eliminating or reducing arcing between the electrodes, particularly when operating at relatively high voltages (e.g., between about 0.1 kV/cm and about 500 kV/cm, including between about 1 kV/cm and 500 kV/cm, between about 5 kV/cm and 500 kV/cm, between about 10 kV/cm and 500 kV/cm, etc.).

FIGS. 18A-18D show another example of a treatment applicator (e.g., a treatment tip) including a pair of C-shaped suction ports that extend partially around the electrodes 1805, 1805'. The treatment applicator 1800 in this example includes an electrode housing 1801 extending from the applicator housing 1803 and includes two sets of tissue-penetrating (e.g., needle) electrodes 1805, 1805' that may extend or retract into the electrode housing 1801. The first set of electrodes 1805 are partially surrounded by a C-shaped suction port 1815. The second set of electrodes 1805' is also partially surrounded by a C-shaped suction port 1815'. Both suction ports may be coupled to the same source of suction or may be coupled to separate suction. The electrodes may move relative to the applicator housing, or the applicator housing may move relative to the electrodes, or both. FIG. 18A shows the treatment applicator with the electrodes retracted into the applicator housing. FIG. 18B shows the treatment applicator with the electrodes extending from the applicator housing. FIG. 18C shows a front view of the treatment applicator. Although the electrodes shown in FIGS. 18A-18D are tissue-penetrating (e.g., needle) electrodes, this configuration may also be used with non-penetrating electrodes.

The treatment applicator shown in FIGS. 18A-18D is configured to reduce arcing between the first set of electrodes 1805 and the second set of electrodes 1805' when operating at relatively high voltages (e.g., between about 0.1 kV/cm and about 500 kV/cm, including between about 1 kV/cm and 500 kV/cm, between about 5 kV/cm and 500 kV/cm, between about 10 kV/cm and 500 kV/cm, etc.). For example, the strike distance 1857 between the first set of electrodes 1805 and the second set of electrodes 1805' is 5% or more (in this example, is more than 25%) than the minimum distance 1855 between the sets of electrodes ignoring the continuous suction barrier, as shown by the dashed line 1857 and the sold line 1855 in FIG. 18D. Each C-shaped suction port is continuous and extends beyond the length of the sets of electrodes.

FIGS. 19A-19C show another example of a treatment applicator including two sets of electrodes 1905, 1905' that are separated by a continuous suction port 1915 that extends beyond the length of the electrodes 1905, 1905'. In this example the suction port 1915 has an I-shape that extends partially around each of the sets of electrodes 1905, 1905'. As in the examples shown in FIGS. 15A-15D, 16A-16D, 17A-17D and 18A-18D, the treatment applicator 1900 in FIGS. 19A-19D also includes an electrode housing 1901 that extends from the applicator housing 1903.

The treatment applicator 1900 shown in FIGS. 19A-19D is also configured to reduce arcing between the first set of electrodes 1905 and the second set of electrodes 1905' when operating at relatively high voltages (e.g., between about 0.1 kV/cm and about 500 kV/cm, including between about 1 kV/cm and 500 kV/cm, between about 5 kV/cm and 500 kV/cm, between about 10 kV/cm and 500 kV/cm, etc.). In FIG. 19D, the strike distance 1957 (shown by the dashed lines) between the first set of electrodes 1905 and the second set of electrodes 1905' is 10% or more (in this example, is more than 25%) than the minimum distance 1955 between the sets of electrodes ignoring the continuous suction barrier of the suction port 1915, as shown in FIG. 19D.

The treatment applicators shown in FIGS. 3A-3B, 4A-4B, 5A-5C, 6A-6C, 7A-7C, 8, 9, 10A-10F, 11A-11C, 12A-12E, 13A-13B, 14A-14C, 15A-15D, 16A-16D, 17A-17D, 18A-18D, and 19A-19D all illustrate examples of treatment applicators configured as treatment tips. These treatment tips may be attached or otherwise coupled to a handpiece of a pulse generator, forming a treatment applicator assembly. Alternatively, any of these treatment applicators may be configured to include an integrated handpiece/handle.

Superficial Treatment Applicators

Also described herein are treatment applicators configured to be especially useful as superficial treatment applicators, where the overall treatment occurs below the surface of the tissue, for example, below the epidermis in case of the treatment of skin. While many of the examples disclosed below are shown to have penetrating electrodes, it should be understood that some of these examples can be implemented with the non-penetrating electrodes for example, by adjusting the energy levels. The treatment applicators with non-penetrating (e.g., surface) electrodes can deliver electrical energy, such as nanosecond pulses, below the surface, for example, between 1 mm and 5 mm deep. Any of these treatment applicators may include a suction chamber that is adapted to be held against the tissue surface (e.g., skin surface) and to draw tissue into the suction chamber; once in the chamber, one or more electrodes may then extend across suction chamber and into or against the tissue. In some examples the electrodes may be tissue-penetrating electrodes (e.g., needle electrodes) that are inserted substantially parallel to the tissue surface. The top of the suction chamber may be transparent so that the tissue (e.g., skin) may be visualized through it, and may include one or more markings what may guide the user. In some examples the one or more markings may indicate the path of the one or more electrodes. Thus, the upper surface may be a viewing window. In some examples the viewing window may include magnification for enlarging the view of the tissue. The one or more markings may include a crosshair, a bullseye, or the like. Such configurations provide an ability to see the targeted lesion or treatment area to improve proper positioning and targeting both during positioning of the treatment applicator and throughout the treatment.

The electrodes may extend completely or partially across the suction chamber. In some examples the electrodes may extend only partially across the chamber; in other examples the electrodes may extend completely across the chamber.

For example, FIGS. 20, 21, 22A-22C, 23A-23C, 24A-24D and 25A-25B illustrate examples of treatment applicators including a suction chamber and one or more needle electrodes adapted to extend across the suction chamber to penetrate in parallel to the bottom open surface of the suction chamber. Such treatment applicators with the penetrating electrodes are especially useful for various subsurface applications of tissue, including without limitation, for subsurface skin treatments where it is desired to avoid epidermis layer of the skin.

In general the suction chamber may be adapted to receive tissue that may be drawn into the suction chamber and retained by suction applied from the top or near the top of the chamber. The chamber may be sized to allow it to substantially fill with tissue (e.g., skins) when suction is applied. The chamber may include a top surface that may be flat or curved (and in some variation may include a window comprising an optically transparent material). The sides of the chamber may be angled or curved so that they are wider at the open bottom or base, and narrower near the top surface. The chamber may be rounded (e.g., circular or oval). In some examples the chamber may be longer (in diameter) than it is deep. The bottom of the chamber is open and may be placed on the tissue so that suction (negative pressure) applied to the chamber may draw the tissue into the suction chamber. The bottom opening into the suction chamber may include a seal, such as a flexible and/or compressible material (e.g., silicone, etc.) that may be scaled against the tissue when suction is applied, and tissue is drawn into the chamber.

As described above, any of these apparatuses, including apparatuses having a suction chamber as shown in FIGS. 20, 21, 22A-22C, 23A-23C, 24A-24D and 25A-25B, may include a suction control that may allow the suction to be turned on/off in the suction chamber. In any of these apparatuses suction (negative pressure) may be turned on but may be diverted from the suction chamber by one or more bleed valves that may be occluded by the user to turn suction on or off in the suction chamber. For example, manually occluding (e.g., using a finger, thumb, palm, etc.) may then cause suction to preferentially be applied to the suction chamber. Releasing the occlusion of the bleed valve may redirect the suction through the bleed valve and release suction from the suction chamber. Alternatively suction to the apparatus may be completely turned off.

Figure 20:
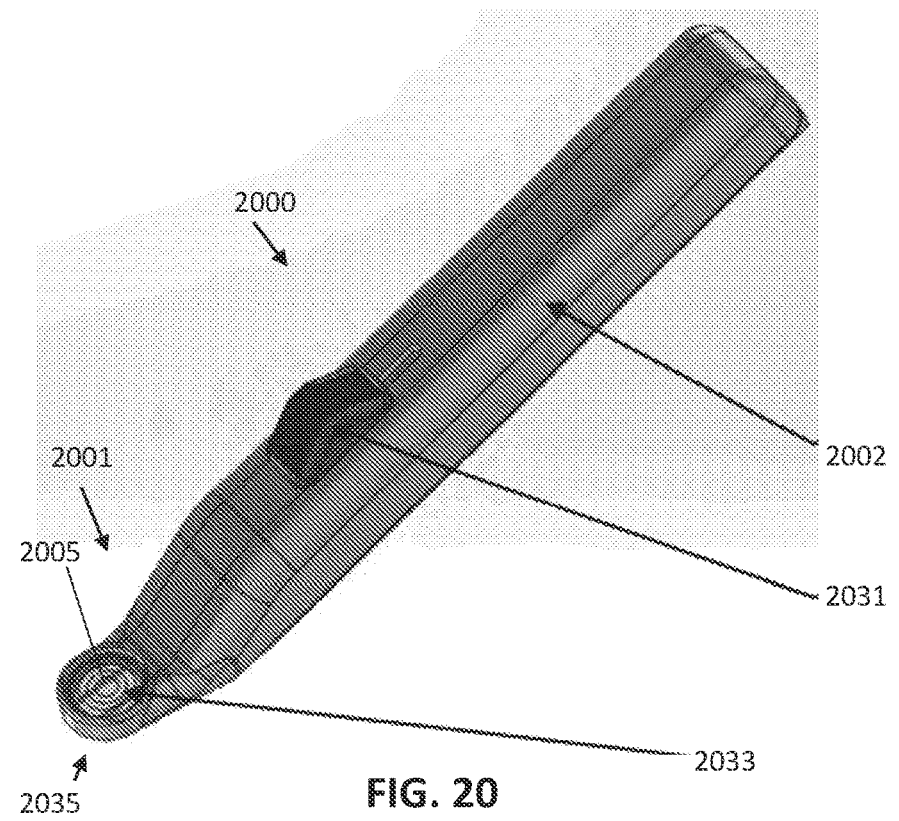
FIG. 20 is an example of a treatment applicator including a suction chamber with a transparent top surface that allows targeting of the transverse needle electrodes through a target tissue.

FIG. 20 shows one example of a treatment applicator 2000 including a handpiece 2002 which may be removably attached to a tip 2001 including the suction chamber 2035. In some examples, as shown in FIG. 20, the tip may be integrated with the handpiece. The handpiece may include one or more controls 2031 that may be used, for example, to trigger the application of vacuum and/or to extend or retract the needle electrodes 2005 across the suction chamber 2035, and/or apply the electrical energy to the needle electrodes. In FIG. 20, the treatment applicator may also include a viewing window 2033 through which the target tissue may be seen. The window may be transparent, as described above.

Figure 21:
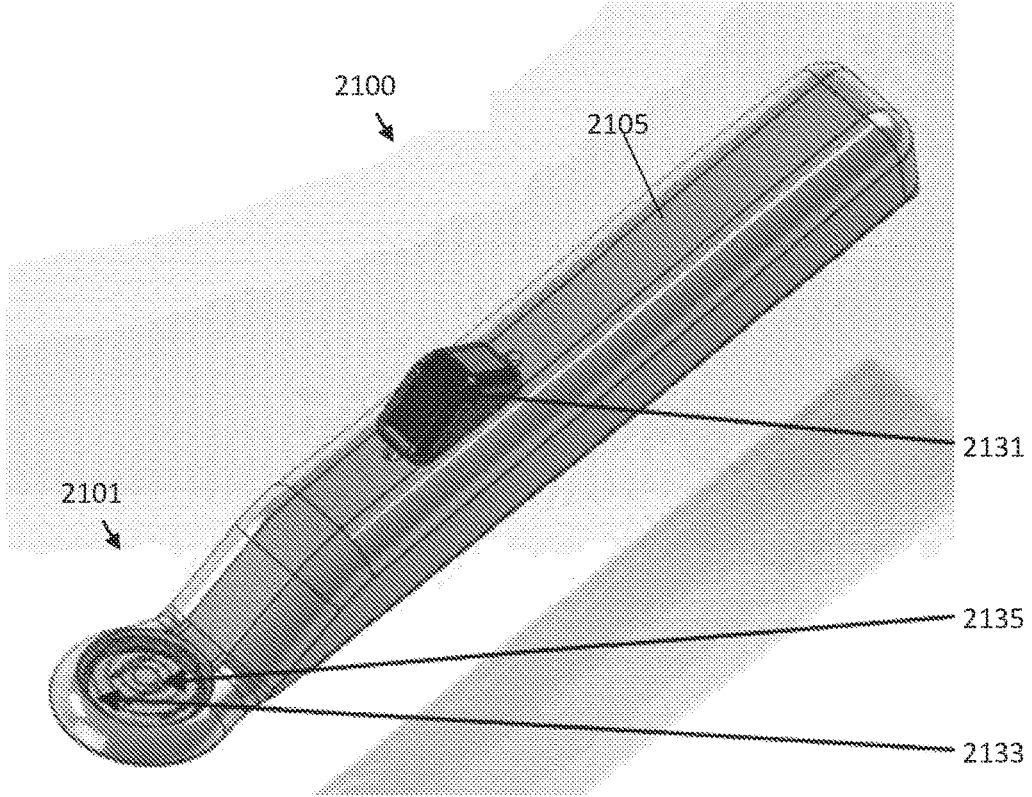
FIG. 21 is another example of a treatment applicator including a suction chamber with a transparent top surface that allows targeting of the transverse needle electrodes through a target tissue.

FIG. 21 illustrates another example of a treatment applicator 2100 that may be used for a larger size lesions or treatment areas. In this example, the treatment applicator 2100 includes a handpiece 2105 and a tip 2101 with 3 or more needle electrodes. In FIG. 21, the suction chamber 2135 includes a transparent upper surface that is configured as a viewing window 2133 and includes guides (shown as concentric, bullseye-like rings) that may assist the user in targeting the portion of tissue to be treated. The handpiece also includes one or more controls 2131, such as a slider to extend/retract the needle electrodes into the suction chamber. Suction may be applied to pull at least a superficial portion of the tissue (e.g., skin) into the suction chamber. In some examples the tip of the electrode may be removable from the handpiece and swapped out with another tip.

Figure 22A:
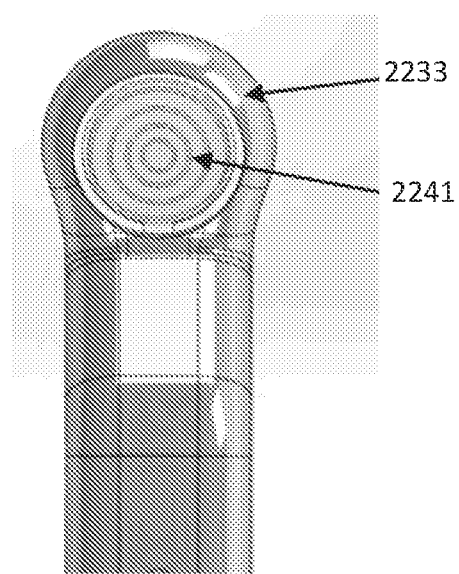
FIG. 22A shows a further example of a treatment tip with a vacuum chamber and a window (including a targeting lens).
Figure 22B:
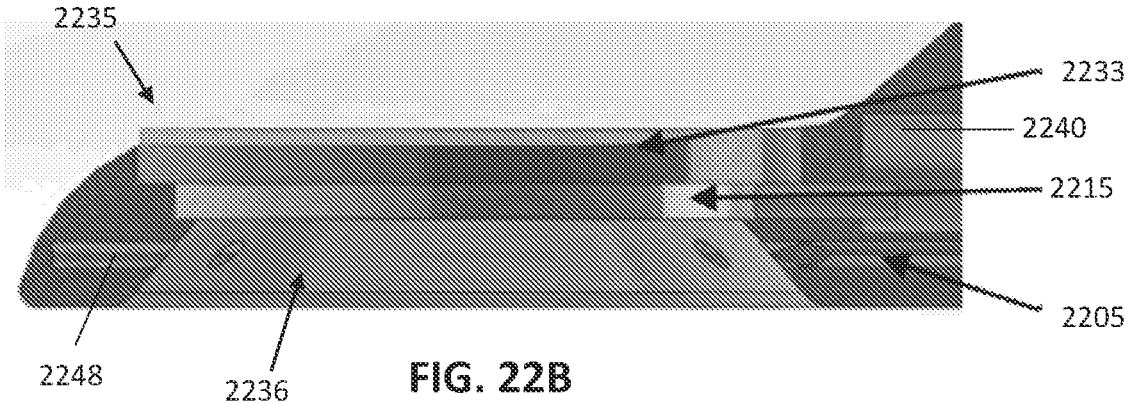
FIG. 22B shows a sectional view through the distal tip region of the treatment tip shown in FIG. 22A with a needle electrode retracted into the side wall of the suction chamber.
Figure 22C:
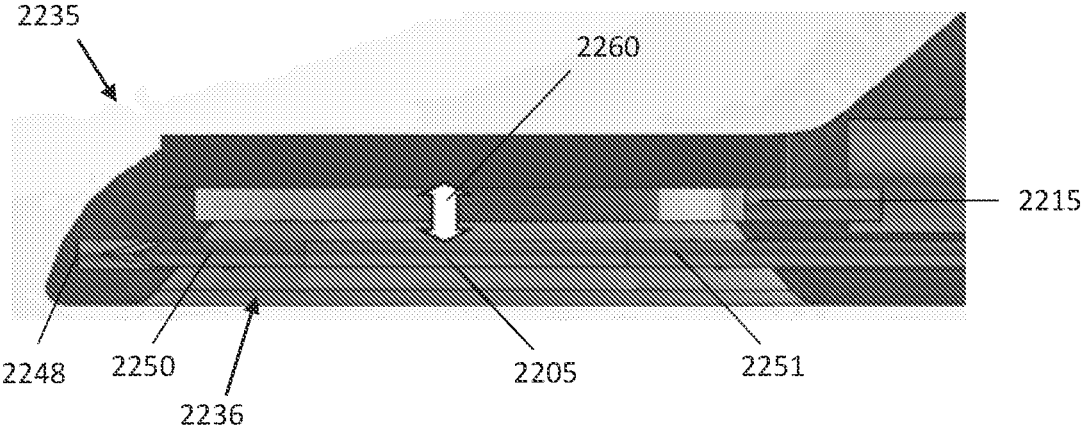
FIG. 22C shows a sectional view through the distal tip region of the treatment tip shown in FIG. 22A with a needle electrode extended transversely into the suction chamber, parallel to the open bottom of the suction chamber.

FIG. 22A illustrates one example of a top view of a treatment tip including a suction chamber. In FIG. 22A the suction chamber includes an optically transparent upper surface (e.g., viewing window 2233). In FIG. 22A, the viewing window includes a plurality of concentric targeting rings 2241. The viewing window may include or be configured as a magnifying lens to help the user see and target very small and hard to see lesions. The treatment applicator may include a light source (e.g., LED, light pipe, etc.) for illuminating the tissue, including the target tissue. In some examples the viewing window may include a filter. FIGS. 22B and 22C illustrate a sectional view through the suction chamber portion of the tip. As shown in FIG. 22B, the needle electrode(s) 2205 may be housed within the tip, retracted fully into the side of the suction chamber 2235. The bottom 2236 of the suction chamber is open, and the suction chamber includes one lone continuous conical wall. The wall includes an opening into the applicator housing 2240 out of which the needle electrode may be extended or into which it may be retracted. The top surface is a transparent viewing window 2233. One or more suction ports 2215 may also open into the suction chamber through the wall or from the top surface (or from the region between the top surface and the wall. In FIG. 22B the needle electrode is shown fully retracted into the wall of the suction chamber. In FIG. 22C the needle electrode is fully extended across the suction chamber so that it extends parallel to the bottom open end of the suction chamber and the tip of the needle electrode is engaged with the opposite wall from the opening out of which the needle extends in a receiving opening 2248. In this example, the needle is configured so that the distal end region (tip region) 2250 is insulated, as is the more proximal end region 2251, so that energy is delivered only from the lateral, uninsulated portion. In some examples, multiple regions along the length of the needle are insulated and exposed, allowing targeting to different regions.

Any of the suction chambers disclosed herein may be configured so that the depth of the suction chamber may be adjusted, which may allow adjustment of the depth of the treatment. The larger the distance between the lens and the electrodes, the deeper the treatment will be performed under the surface of tissue (e.g., under the epidermal layer of the skin). For example, a distance adjustment may be provided by an expandable region 2260 that may be included between the top surface and the opening through which the needle electrode retracts or extends. In FIGS. 22A-22C, the expandable region may be a threaded region that may be screwed in (to shorten the chamber) or out (to expand the chamber). In some examples the suction chamber may have a fixed depth.

FIGS. 23A-23C illustrate an example of a treatment tip in which three needle electrodes are shown. In this example, the top surface is a transparent viewing window through which the tissue can be viewed. Without tissue in the suction chamber, the three needle electrodes can be seen partially extended in FIG. 23A and fully extended in FIG. 23B. As described above, the needles electrodes 2305 may be insulated at the distal tip 2350 and more proximal region 2351, leaving an uninsulated region 2352 that may apply energy. The energy may be applied between two or more of the needle electrodes (in a bipolar or tripolar configuration) or a ground pad or other return electrode may be used (in a monopolar configuration). The electrical insulation may be any appropriate electrical insulating material, such as polyimide or equivalent. This insulation pattern may restrict the treatment area to the center of the targeting location shown through the transparent viewing window.

In FIG. 23A the control 2331 on the handpiece may be driven distally (as shown in FIG. 23B) to extend the needle electrodes across the suction chamber. The same control or a second control may be used to trigger the application of energy (e.g., nanosecond pulsed energy) to treat tissue. These devices can be used to treat multiple sizes and shapes of lesions. The dimensions of the suction chamber and the number of needle electrodes may be larger or smaller, e.g., the diameter of the suction chamber may be, e.g., between 4 mm and 60 mm (e.g., between 5 mm and 30 mm, between 5 mm and 25 mm, etc.). The depth may be, e.g., between 0.5 mm and 10 mm (e.g., between 1 mm and 5 mm, between 1 mm and 4 mm, between 1 mm and 3 mm, etc.). As mentioned above, in some examples the depth may be adjustable. FIG. 23C shows a bottom view of the suction chamber of the device of FIG. 23B with the tissue in the suction chamber and the needle electrodes fully deployed.

In some variations the needle electrode may be only partially extended across the suction chamber, and the distal end of the needle electrode may be configured to apply the electrical energy (e.g., may be the active region).

Figure 24A:
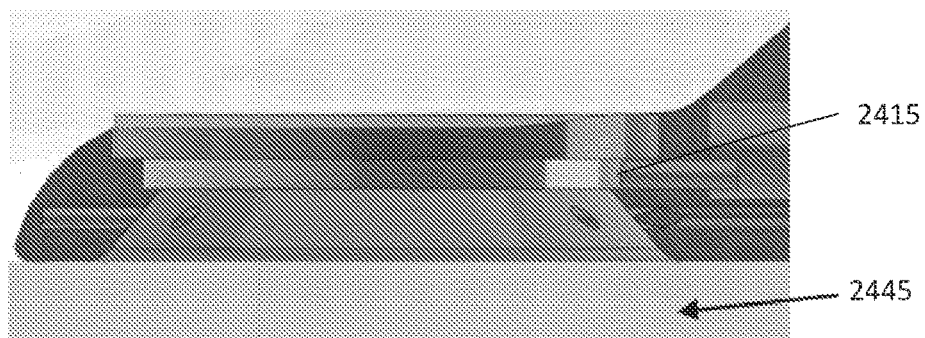
FIGS. 24A-24D illustrate the operation of one example of a treatment tip including a suction chamber and a plurality of needle electrodes.
Figure 24B:
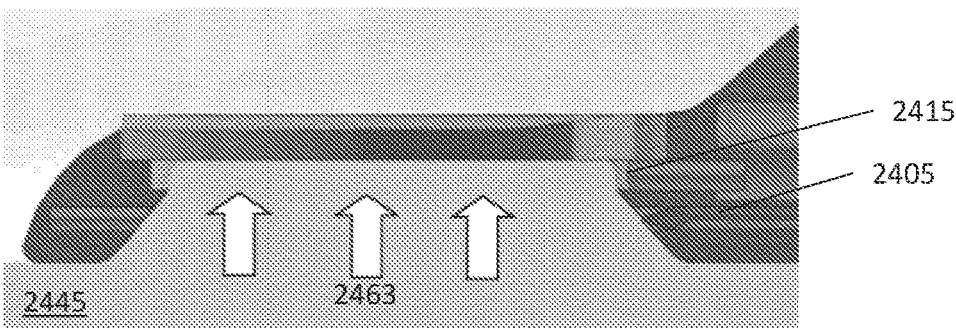
Figure 24C:
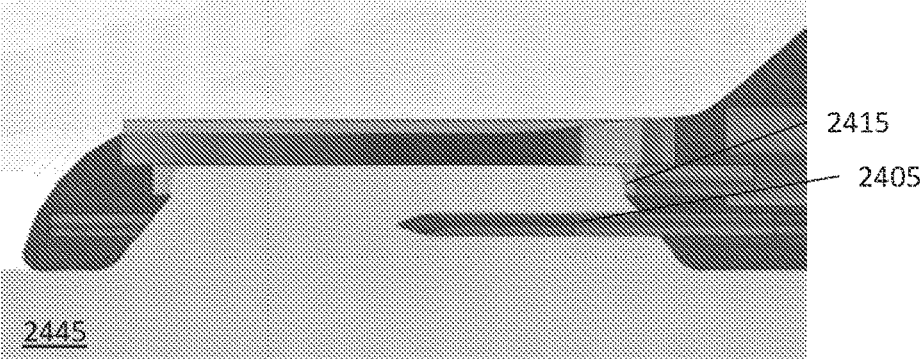
Figure 24D:
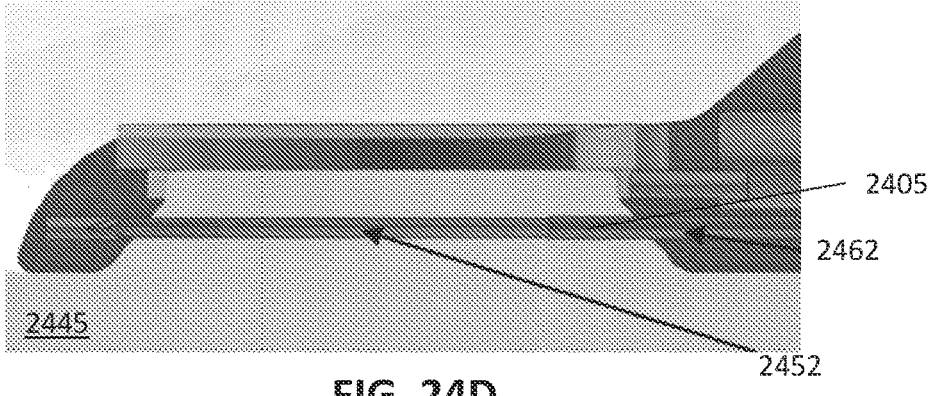

FIGS. 24A-24D illustrate the operation of one example of a treatment tip configured for treatment of superficial tissue using a suction chamber and needle electrodes traveling parallel to the open bottom surface. In FIG. 24A the section through the suction chamber shows the device applied onto the tissue (such as skin tissue) 2445 before any suction is applied. The open bottom side of the suction chamber may form a seal against the tissue (skin). In FIG. 24B a negative pressure (e.g., vacuum or suction) 2463 is applied from one or more vacuum ports in the suction chamber, drawing the tissue into the suction port 2415. The open bottom surface may include a peripheral scaling material (e.g., silicone) to seal against the tissue. The needle electrode(s) 2405 are fully retracted into the side of the suction chamber, as shown in FIGS. 24A-24B. In FIG. 24C, once the tissue is drawn into the suction chamber the needle electrodes may be driven into the tissue, so that they extend parallel to the bottom opening of the suction chamber, and therefore substantially parallel within a superficial region of the tissue, beneath the surface of the tissue. FIG. 24D shows the needle electrode fully extended, exposing a central active region 2452.

Energy may then be applied from the uninsulated middle region of the needle electrode. In some examples treatment may occur between the active region(s). The number of active regions (e.g., the number of needles with active regions) may be increased to increase the treatment area. In some examples the number of needles and/or active regions may be increased to increase the treatment area. Portions or regions of the needle may be insulated to form non-active regions 2462, such as the regions proximal and distal to the active region(s), as shown in FIG. 24D.

Figure 24E:
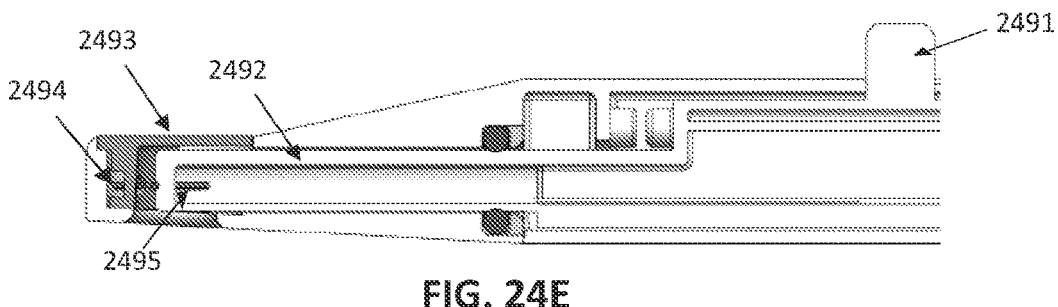
FIG. 24E illustrates one example of a treatment tip configured for treatment of superficial tissue using a suction chamber and surface electrodes.

FIG. 24E illustrates another example of a treatment tip configured for treatment of superficial tissue using a suction chamber that implements surface electrodes (rather than needle electrodes) that can be used, for example, to pinch the tissue. In the example of FIG. 24E, a static surface electrode 2494 (e.g., wire electrode) is mounted in the distal region of the treatment tip, and a dynamic surface electrode 2495 (e.g., wire electrode) is mounted on a sliding shaft 2492, which is coupled with the sliding button 2491. A vacuum may be pulled using a control, either manually or using a bleed valve as described above. In some examples the control (e.g., an opening that may be covered by the user's finger(s)) may be on the sliding button 2491. Once the tissue is drawn into the tip, e.g., by applying the vacuum, the user may slide the sliding button 2491 forward. The sliding button and/or the sliding shaft may be biased toward rear of the assembly with one or more biases (e.g., compression springs). As the user slides the sliding button 2491 forward, once the vacuum has drawn the tissue into the tip, the tissue can be pinched between the static surface electrode 2494 and the dynamic surface electrode 2495, which can be observed through a transparent viewing window 2493. Such treatment applicators with the surface electrodes are especially useful for various surface applications of tissue, including without limitation, for surface skin treatments. Each of the static surface electrode and the dynamic electrode may be a type of a wire, a bar, a spring and the like, and any appropriate number of surface electrodes may be used, for example, 2, 3, 4, etc.

Figure 25A:
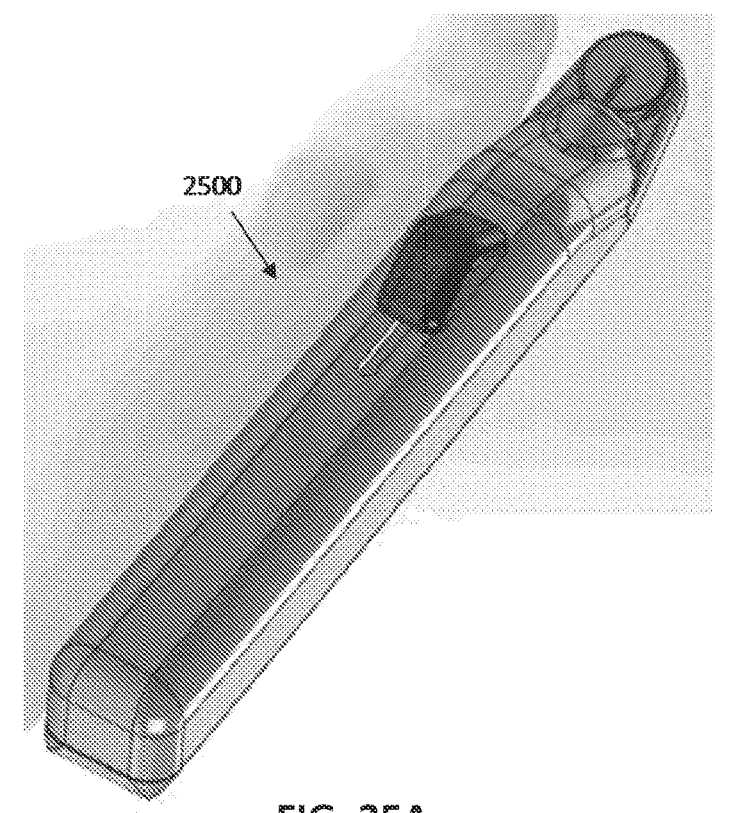
FIG. 25A is a top perspective view of another example of a treatment applicator including a distal tip portion that includes a suction chamber, in which the top of the suction chamber is configured as a return electrode.
Figure 25B:
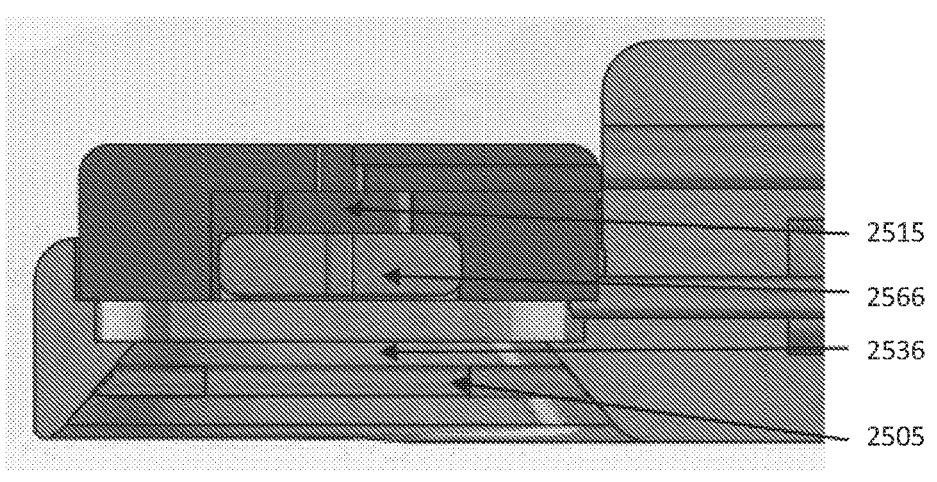
FIG. 25B shows a section through the suction chamber of the treatment tip of FIG. 25A.

In some examples, a return electrode may be part of the suction chamber, such as a part of the top surface. For example, FIGS. 25A-25B illustrate an example of a configuration in which the suction chamber includes a plate (one electrical pole) 2566 that will be in contact with the tissue, such as skin, at the top surface of the suction chamber. The needle electrodes 2505 may be inserted into the tissue held within the suction chamber and inserted below the top of the tissue or skin. The needle electrode, once extended across the suction chamber, or partially across the suction chamber, may be positioned opposite this upper electrode (e.g., plate electrode, or mesh electrode) 2566, which may act as a return electrode. In the example treatment applicator 2500 shown in FIG. 25B, the top surface of the suction chamber may include a viewing window as described above, or it may be replaced with the solid plate electrode. In this example, energy may be conducted between the needles just below the surface of the tissue and the plate electrode at the skin surface on the top of the suction chamber. The treatment tip may be placed on the tissue, the vacuum may pull the tissue or skin flush with top of the suction chamber, including the return electrode (e.g., plate or mesh) and then the needle electrodes may be inserted through the tissue, as shown in FIGS. 24A-24D).

In FIG. 25B, the vacuum may be applied from above the plate electrode through a suction port 2515 coupled to a suction channel. The open suction chamber 2536 may draw the tissue up and into contact with the return electrode.

Various example of the treatment applicators with the vacuum assisted side deploying electrodes disclosed herein not only provide benefits and advantages of the improved targeting, but they reduce pressure required to perform the treatment and also reduce the number of electrodes (e.g., needles) required to perform the treatment, which in turn minimizes any tissue trauma or pain that may be associated with the insertion of the needle electrodes.

Also described herein are treatment applicators that may be particularly well suited for treatment of skin tissue by isolating the region of skin to be treated within treatment applicator prior to applying the pulsed electrical treatment. Some of the apparatuses described herein may use suction to draw the tissue region to be treated into the chamber to isolate it for treatment. The treatment may be applied to the portion of the tissue (e.g., skin) drawn into the chamber by tissue penetrating or non-penetrating electrodes. The chamber may be configured to hold 0.2 cubic cm or more (e.g., 0.3 $cm^3$ or more, 0.4 $cm^3$ or more, 0.5 $cm^3$ or more, 0.6 $cm^3$ or more 0.7 $cm^3$ or more, 0.8 $cm^3$ or more, 0.9 $cm^3$ or more, 1 $cm^3$ or more, etc.) of tissue. The tissue may be drawn into the chamber of the treatment applicator and may be pulled above the plane of the tissue, away from the other tissue, nearby sensitive regions, such as the eyes, mucus membranes, etc. These apparatuses may include visualization, such as one or more windows into the chamber of the treatment applicator.

Any of the apparatuses and methods described herein may be used to treat conditions, lesions, or disorders such as syringoma, seborrheic keratosis, keloids, molluscum contagiosum, sebaceous hyperplasia, congenital capillary malformation (port-wine stain), melasma, actinic keratoses, dermatosis Papulosa nigra, angiofibroma, skin tumors, basal cell carcinoma (BCC) and warts. In some examples, it may be particularly beneficial to treat these conditions (including, but not limited to syringoma) with apparatuses and methods configured to draw the tissue to be treated into a chamber of the treatment applicator by suction, isolating it from potentially sensitive nearby tissue regions, before applying treatment.

For example, described herein are treatment application designs and corresponding methods that isolate the tissue to be treated by pulsed electrical treatment into the treatment applicator and away from nearby non-treatment region by suction to improve safety. For example, facial regions, including in particular regions around the eyes or intraorbital regions, and/or near mucus membranes may be beneficially isolated using these methods and apparatuses. In some of the treatment tips described herein, the suction chamber may be oriented so that the optical axis extends through the treatment tip in the same direction that the electrodes advance, relative to the tissue. For example, FIGS. 26A-26D illustrate an example of a treatment applicator that includes a chamber for drawing in the tissue to be treated and allowing visualization through the treatment applicator. In the apparatus shown in FIGS. 26A-26D, the treatment tip includes deployable electrodes that may be configured either as tissue-penetrating electrodes (e.g., needle or microneedle electrodes) or as non-penetrating electrodes (e.g., plate electrodes, wire electrodes, loop electrodes, etc.).

In this example, the user may position the distal end of the treatment applicator (the treatment tip) onto the treatment area and activate suction within the suction chamber of the tip. Suction may be applied by a suction pump to which the treatment applicator is connected, or in some examples by a vacuum or suction chamber within the treatment applicator;

negative pressure may be generated within the treatment applicator itself (e.g., by moving a plunger or other mechanism) to draw tissue into the suction chamber of the treatment tip. The tissue may be drawn into the treatment tip as far as the elasticity of the tissue to be treated may allow. In some examples, the midline of the treatment applicator may form a visual channel through which the tissue may be viewed. For example, the electrode housing may include a central passage through which the tissue may be viewed, between the electrodes. Alternatively, the electrodes may move in/out of the line of sight through the treatment applicator. In some cases the suction path through the electrode housing may also allow imaging through the electrode housing. Any of the apparatuses described herein may also include a light source for illuminating the tissue and/or magnifying optics for viewing the tissue.

In operation, the user may view the tissue through the treatment applicator and may apply suction to draw the tissue into the suction chamber, during, after or before applying suction. The treatment applicator may include an internal source of suction or may be coupled to an external source of suction. The user may then advance the retractable tip (within the body of the applicator housing) distally so that the electrodes are placed in contact with the tissue. If tissue-penetrating electrodes are used, the needles may be inserted distally into the tissue, rather than parallel, as shown in the examples above.

Figures 26A, 26B, 26C, 26D:
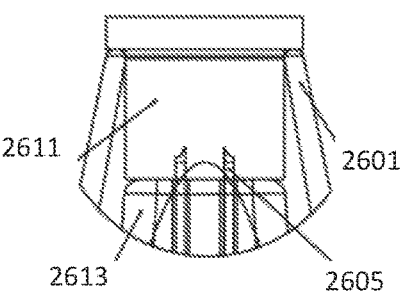
FIGS. 26A-26C illustrate operation of another example of a treatment applicator including a tip having a suction chamber and a plurality of electrodes with a viewing window allowing viewing of the tissue through the tip.
FIG. 26D shows an enlarged view of the distal end of the tip region.

For example, in FIG. 26A the treatment applicator 2600 includes a main body portion 2601 (configured as an applicator housing 2601 in FIGS. 26A-26D) forming a tip region 2603. The applicator housing forms an internal chamber (suction chamber) within the open distal end of the applicator housing into which tissue may be drawn by applying suction. The electrode housing 2613, which in FIG. 26A is internal to the applicator housing, include two or more (e.g., two sets) of electrodes 2605 that may extend distally of the electrode housing. In FIG. 26A the treatment applicator includes a bias (compression spring or just spring 2609) that is releasably locked in an undeployed state. The bias holds the retractable tip with the electrodes (e.g., needle electrodes) proximally until a control 2607 releases the electrode housing to drive the electrodes distally.

FIG. 26B shows the operation of the apparatus 2600 of FIG. 26A to draw tissue 2611 into the suction chamber. For example, a vacuum pump may draw tissue 2611 into the treatment tip, as shown. The user may then cause the electrodes from the electrode housing to advance distally and engage with the tissue held within the suction chamber, as shown in FIG. 26C. In some cases the user may actuate a control (e.g., a release control, an electrode advance control, etc.) 2607 to drive the electrodes distally. In some examples the control may allow the user to manually (at a controlled rate) advance the electrode(s) distally until the end of the electrode housing rests firmly against (for non-penetrating electrodes) or is inserted into (for tissue penetrating electrodes) the tissue within the suction chamber. For example, the user may slide a control (e.g., button, knob, slider, etc.) distally driving the tissue-penetrating electrodes into the tissue or rest firmly non-penetrating electrodes against the tissue. Once the electrodes are in or on the tissue within the suction chamber, treatment may be applied. For example, treatment may be applied from the one or more electrodes using a finger switch or foot pedal. This configuration may allow treatment of the target tissue from as far away as possible for safety of both the user and the patient. As stated above, this may be particularly useful where the target treatment tissue is facial, such as round the eyes or intra-orbital. The treatment applicator may be easy to use and may include visual guidance.

For example, FIG. 26D shows an enlarged view of the distal end of the treatment applicator of FIGS. 26A-26C, showing the applicator housing 2601 with tissue 2611 drawn therein. The inside of the applicator housing forms a suction chamber holding the tissue. In FIG. 26D the electrode 2605 are needle electrodes that extend proud of the electrode housing 2613 within the applicator housing. For example, in use, the treatment applicator may draw more than about 2 mm (e.g., more than 3 mm, more than 4 mm, more than 5 mm, etc.) into the suction chamber. In FIG. 26D the retractable/extendable electrode housing is advanced distally until it rests firmly against the target tissue distally. The tissue-penetrating electrodes in this example stand proud of the electrode housing by about 1 mm, thus, the apparatus may insert the electrode up to this length (e.g., 1 mm).

Figure 27A:
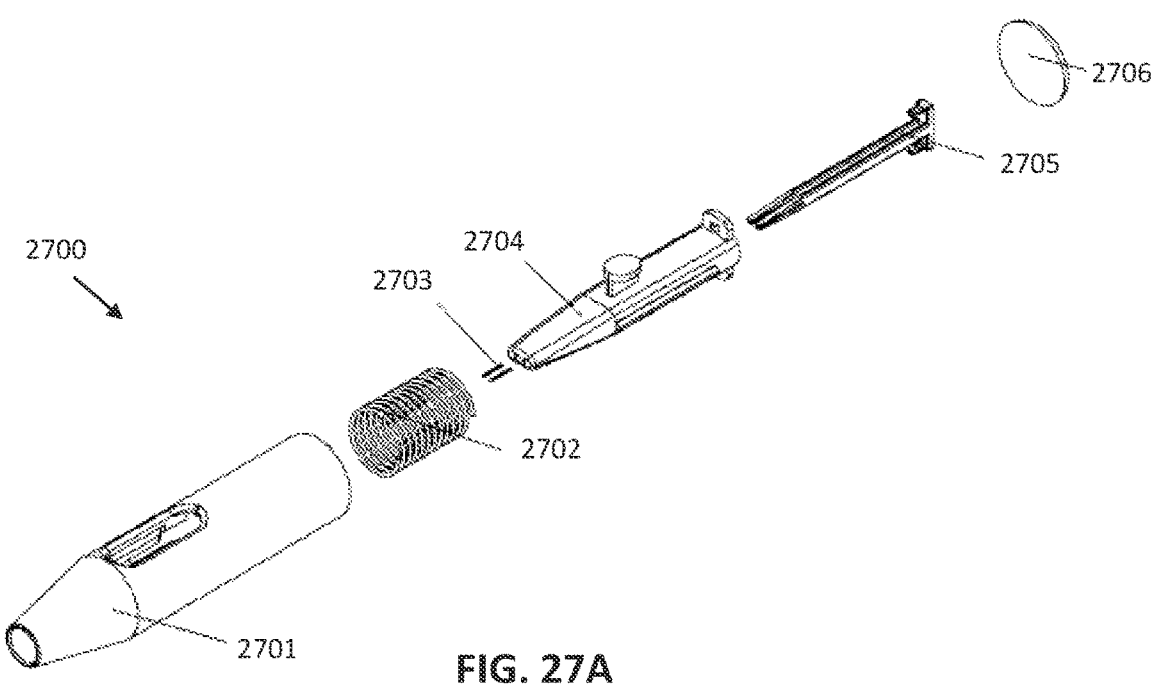
FIGS. 27A and 27B show examples of exploded views of a treatment applicator including a vacuum treatment tip having either tissue-penetrating electrodes (FIG. 27A) or non-penetrating electrodes (FIG. 27B) similar to those shown in FIGS. 26A-26D.
Figure 27B:
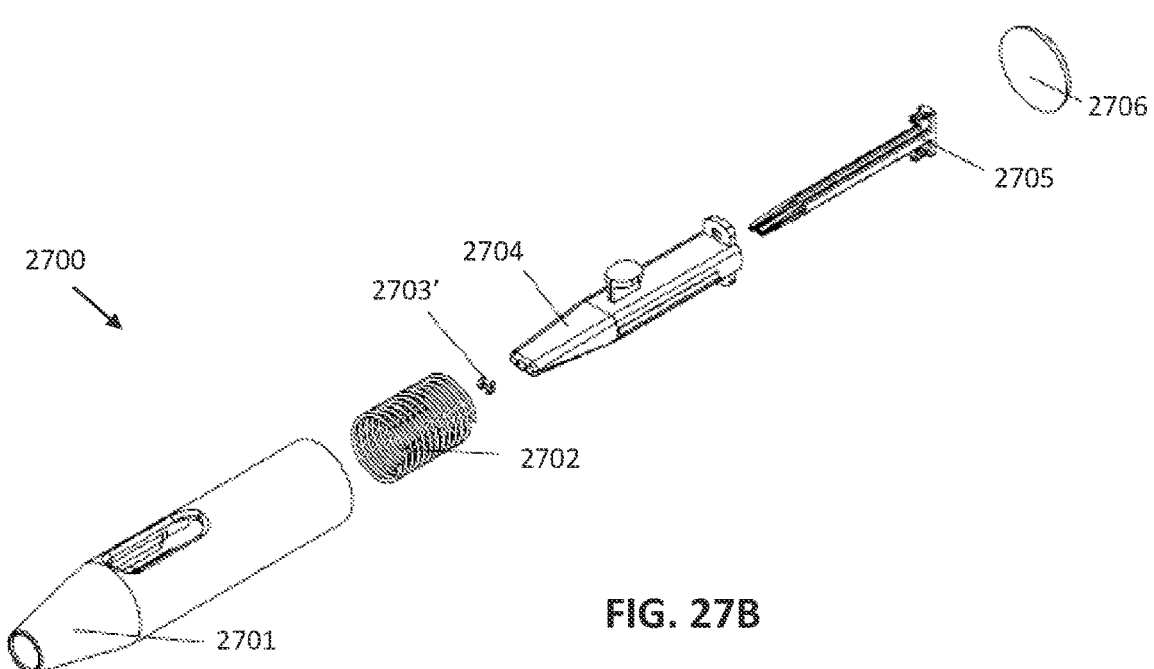

FIGS. 27A and 27B show examples of exploded views of an apparatus similar to that shown in FIGS. 26A-26D. In FIG. 27A the treatment applicator (treatment tip 2700) includes by example two tissue-penetrating electrodes 2703. In contrast, FIG. 27B shows a similar treatment apparatus with two non-penetrating electrodes 2703'. Both variations comprise elongate treatment applicators 2700 that include a main body 2701. The inside of the distal end of the main body 2701 (also referred to herein as the applicator housing) may form the suction chamber, as illustrated in FIGS. 26A-26C. The electrode housing 2704 is held within the inside of the main body in part by a bias (e.g., compression spring) 2702. The electrode housing 2704 holds the electrodes 2703 (FIG. 27A) or 2703' (FIG. 27B) and internal electrical connections via an electrode holder 2705. In some examples the electrode housing may be adapted or configured to allow the user to view down the inside of the treatment applicator and out of the distal end, so that a target tissue can be identified, as described above. The back of the apparatus may include a cap or cover 2706.

FIGS. 28A-28D illustrate another example of a treatment applicator including a suction chamber within the applicator housing and distally biased electrodes. As in FIGS. 26A-26D, the example shown in FIG. 28A-28D also includes a plurality of electrodes (either tissue penetrating or non-penetrating).

Figure 28A:
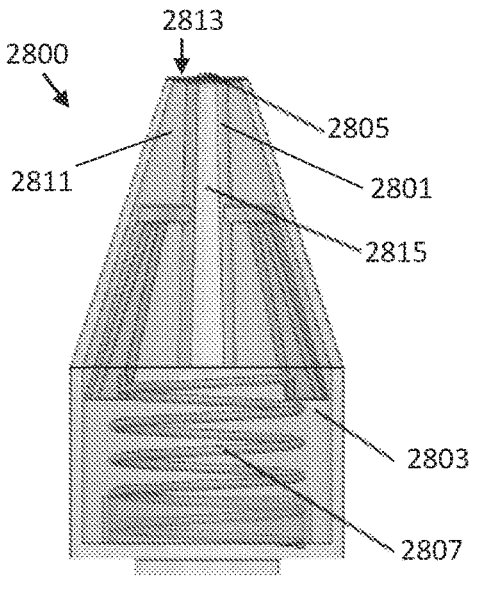
FIGS. 28A-28B illustrate operation of another example of a treatment tip including a suction chamber as described herein.

FIG. 28A shows a distal end of the treatment applicator 2800, including an applicator housing 2803. The inside of the applicator housing at the distal end may form a suction chamber 2811. An internal electrode housing 2801 may be axially biased by a bias (e.g., compression spring 2807). The electrode housing 2801 may be driven all the way up to the opening 2813 of the applicator housing or it may be just proximal to it; typically space around the electrode housing within the opening allows suction to draw tissue into the suction chamber and drive the electrode housing proximally against the bias (compression spring). This may drive the electrodes 2805 on the electrode housing distally against the tissue.

Figure 28B:
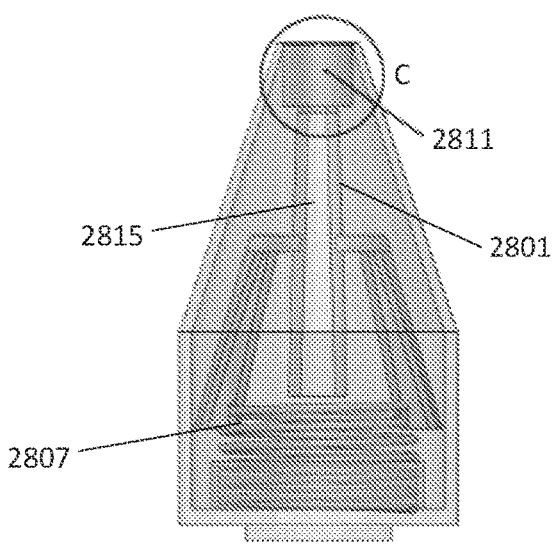
Figure 28C:
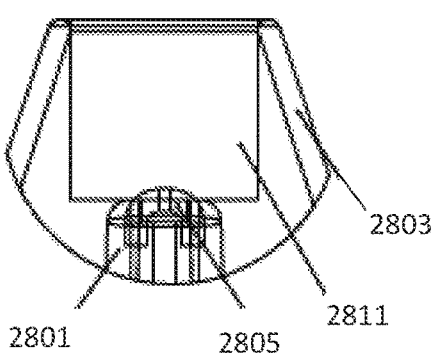
FIG. 28C shows an enlarged view of the distal end of the treatment tip of FIG. 28B.

As is shown in FIGS. 28A-28B there is an optical channel 2815 through the treatment applicator extending from a proximal end of the treatment applicator to the distal end opening 2813; this optical channel passes through the electrode housing, and through the applicator housing. FIG. 28B shows the treatment applicator with tissue drawn into the suction chamber 2811 formed within the end of the applicator housing. As suction draws the tissue into the suction chamber, it compresses the bias 2807 proximally, driving the electrodes on the electrode housing into the tissue, while driving the electrode housing proximally. FIG. 28C shows an enlarged view of region C from FIG. 28B. In FIG. 28C the suction chamber portion 2811 holding tissue drives against the non-penetrating (loop) electrode 2805 on the electrode housing 2801 as it is displaced proximally. In this example, the tissue may be drawn into the suction chamber by about 2 mm or greater (e.g., 3 mm or greater, 4 mm or greater, 4.5 mm or greater, 5 mm or greater, etc.).

Figure 28D:
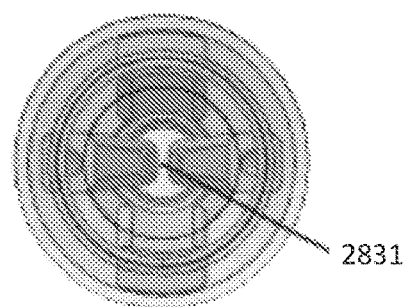
FIG. 28D shows a view of the distal end of the treatment tip of FIGS. 28A-28C.

FIG. 28D shows an example of a window 2831 including magnifying optics for viewing through the treatment applicator to position it on the tissue. A user may locate the distal end of the treatment tip and optimally locate the treatment location by viewing the treatment area through an illuminated window. The window may include a magnifying lens at the proximal end of the treatment applicator.

In use, the user may place the distal end of the treatment tip of the treatment applicator in position on the tissue by viewing the treatment area through the proximal end of the apparatus. In this example, the proximal end includes a LED that illuminates the viewing window and magnifying optics to assist in targeting. Once the distal end of the treatment tip has been positioned on the tissue, the user may apply suction to the suction chamber within the applicator housing. In some examples the user may actuate a vacuum pump; alternatively the user may move a control on the handpiece portion of the treatment applicator to generate suction within the treatment tip. Tissue is then drawn into the inside of the applicator housing (e.g., the suction chamber portion) as far as the elasticity of the tissue will allow. As the tissue is drawn in, the compression spring may compress, maintaining a constant pressure against the distal end of the electrode housing and the tissue drawn into the applicator housing (e.g., the suction chamber). This may seal the tissue within the suction housing and against the electrodes on the electrode housing. If the electrodes are tissue penetrating electrodes, they may be driven fully into the tissue. If the electrodes are non-penetrating electrodes, they may be secured against the tissue. Once the tissue is fully within the suction chamber, the treatment may be applied. For example, a foot petal or hand control (e.g., finger switch) may be used to activate the application of pulsed electromagnetic energy (e.g., sub-microsecond pulsing, nanosecond pulsing, etc.).

FIGS. 29A and 29B show exploded views of a treatment applicator similar to that shown in FIG. 28A-28D. FIG. 29A shows the exploded view of an apparatus including tissue penetrating electrodes 2902 while FIG. 29B shows the exploded view of an apparatus with non-penetrating electrodes 2902'. Both exploded views include the outer applicator housing 2901, an inner electrode housing 2903, a bias (e.g., compression spring 2904), a proximal cover 2905 as well as a magnifying window 2906.

In any of the examples described herein one or more electrodes may be present in or near the suction chamber, while the second electrode (or set(s) of electrodes) may be on the inner electrode housing. For example, FIG. 30 shows another example of a treatment applicator including an internal suction chamber within which one or more electrodes may be applied against tissue drawn into the suction chamber. In FIG. 30 the applicator housing 3001 is a tubular enclosure the outer edge of which includes an electrode 3005. One or more central electrodes (shown in this example as a non-penetrating, cylindrical electrode) 3005' may be positioned at different relative positions within the applicator housing 3001 and may allow suction to be applied around the inner electrode(s). Tissue may be drawn into the inside of the applicator housing by applying suction through the space between the distal end opening of the applicator housing 3009 and the cylindrical center electrode(s) 3005'. As tissue is suctioned into the suction chamber at the distal end of the treatment applicator, the tissue will seal between the outer electrode 3005 and the inner cylindrical electrode (s) 3005'.

Figure 31A:
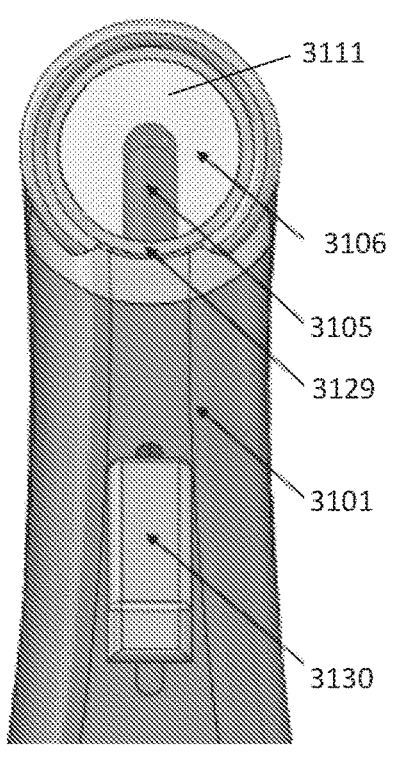
FIG. 31A-31D illustrate another example of a treatment tip having a suction chamber with a transparent window for viewing the target tissue as well as an example of a cylindrical electrode.
Figure 31B:
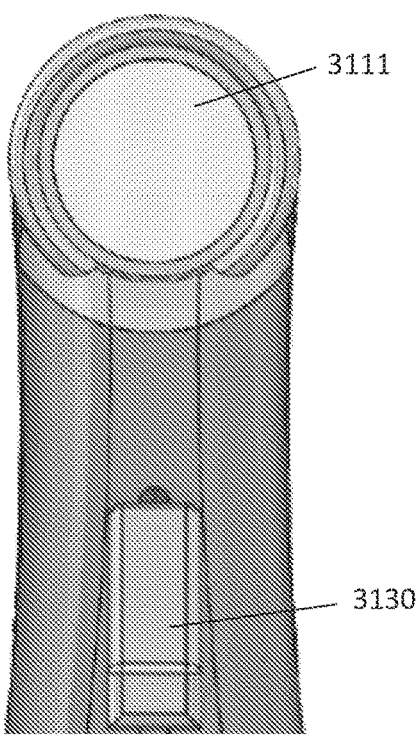
Figure 31C:
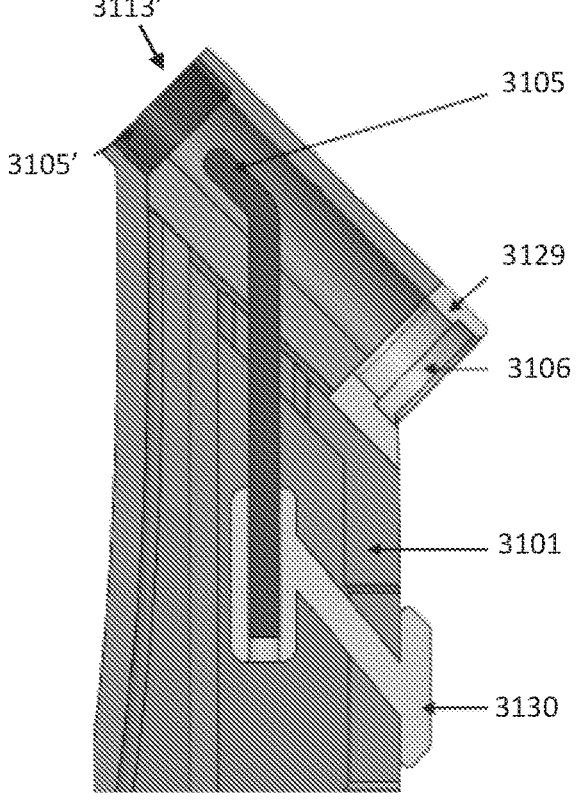
Figure 31D:
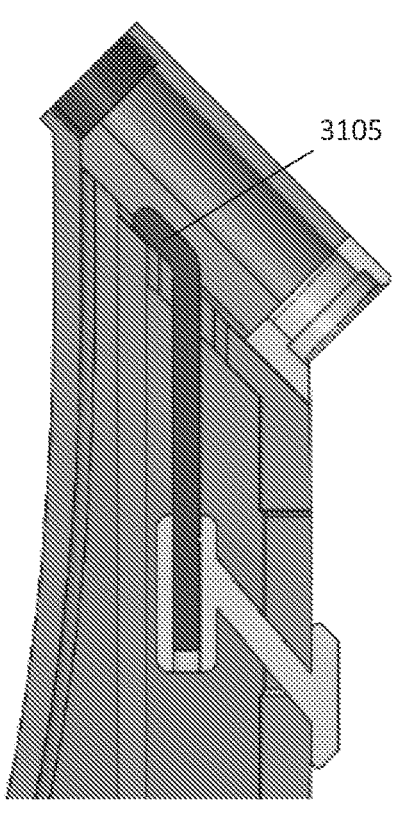

FIGS. 31A-31D illustrate another example in which the treatment applicator is configured to allow viewing through the tissue to be treated and to allow positioning of the electrode(s). FIG. 31A shows a treatment applicator that includes an outer applicator housing 3101 and a window 3106 through the applicator housing and out of the distal opening into the applicator housing. This example also includes a light source and a light pipe 3129 for illuminating the tissue to be treated. One or more electrodes 3105 may be positioned within the applicator housing. In this example, the electrode 3105 is configured as a non-penetrative, e.g., cylindrical, electrode. A second electrode or set of electrodes 3105' may be positioned around the periphery of the distal end opening into the applicator housing, as shown in FIG. 31C. It may be attached to an electrode housing or other structure within the device that may allow it to be moved. For example, as shown in FIGS. 31B-31D the control 3130 (shown as a button or slider in this example) may slide distally to advance the electrode more centrally into the inner chamber (e.g., vacuum chamber 3111) of the applicator housing. Thus, one electrode or sets of electrodes may be moved relative to the distal end opening, including moving in/out of the field of view.

FIGS. 31C and 31D show side sectional views through the apparatuses of FIGS. 31A and 31B, respectively. In FIG. 31C the electrode 3105 is centered in the field of view and may contact tissue drawn into the suction chamber when suction is applied. A second electrode or set of electrodes 3105" is positioned on the periphery of the distal opening 3113' into the applicator housing 3101. In FIG. 31D the control 3130 has been moved proximally, moving the electrode 3105 out of the field of view through the window 3106, as shown in FIG. 31B. As mentioned, the apparatus may include a light source (e.g., LED, light pipe, etc.) 3129.

In the example shown in FIGS. 31A-31D, the control 3130 is attached to the cylindrical electrode to allow the user to control the position of the electrode relative to the tissue. For example, the electrode may be moved out of the way of the viewing window for unobstructed viewing. In some examples the control may also or alternatively move the electrode closer or into contact with the tissue. Once targeting is complete, the control may allow the electrode to be moved distally, locking into place for treatment. In some examples the viewing window is plastic or glass, and may be a lens (e.g., may magnify). The negative pressure (e.g., vacuum) may be applied once positioned. The suction may be applied after moving the electrode into position.

Figure 31E:
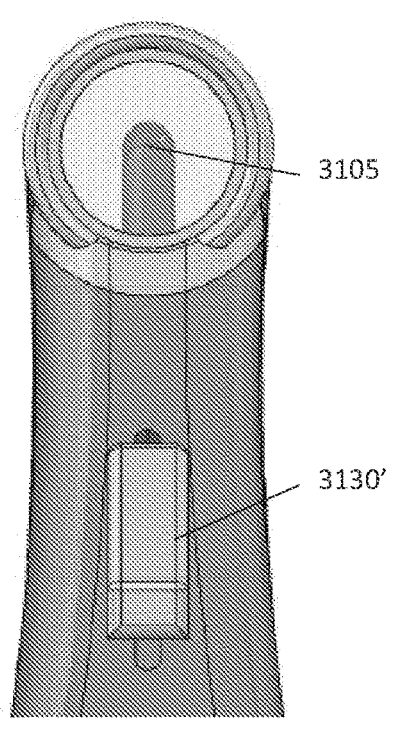
FIG. 31E shows a view of an alternative example of a treatment tip similar to that shown in FIG. 31A, but with the control configured to apply negative pressure to the suction chamber.

FIG. 31E is another example of a treatment applicator similar to that shown in FIGS. 31A-31D. In this example the control (button 3130') may instead serve as a control for an internal source of negative pressure, such as a plunger. The viewing window may be used to target, and a second control may be used to move and/or position the central electrode 3105, or it may be maintained in a fixed position.

Figure 32A:
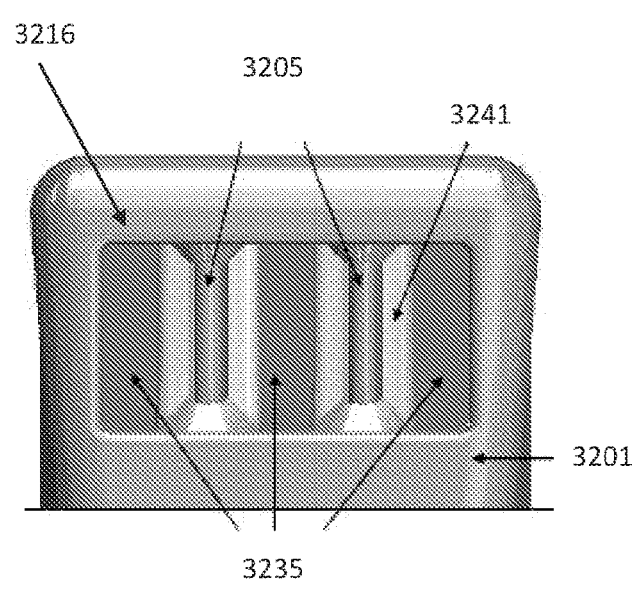
FIG. 32A illustrates an example of a distal end region of a treatment tip having a plurality of electrodes (in this example, non-penetrating electrodes) including adjacent suction regions.
Figure 32B:
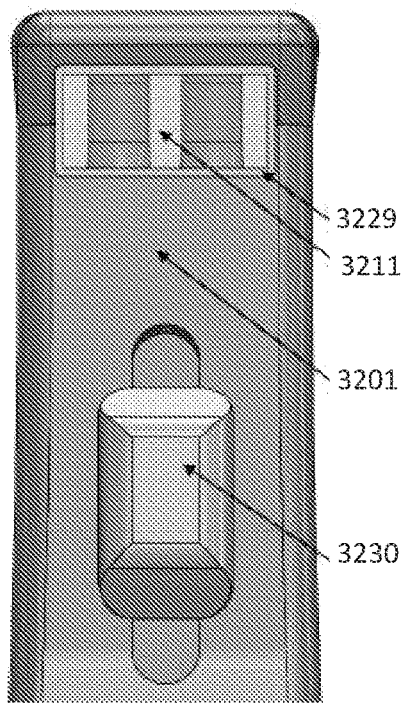
FIG. 32B shows an electrode holder and a main body of the treatment tip shown in FIG. 32A.
Figure 32C:
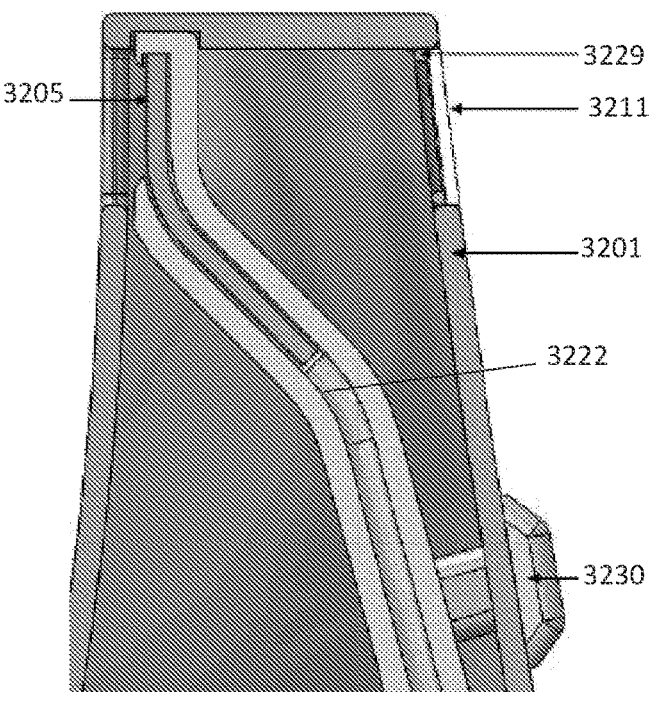
FIG. 32C is a side, sectional view of the treatment tip of FIGS. 32A-32B with the electrodes extended.

FIGS. 32A-32F illustrate another example of a treatment applicator. In this example a plurality of electrodes is positionable within an applicator housing that also includes a suction chamber at the distal opening. A window of the applicator housing 3201 of the device allows the user to view the tissue and the electrodes 3205 before applying suction and/or applying pulsed electrical treatment. In FIG. 32A, a portion showing the distal end opening 3216 of the treatment applicator is shown. Two electrodes are coupled to an electrode housing 3241 that include gaps (spaces) to allow airflow (airway 3235). FIG. 32B shows a control 3230, the applicator housing body 3201, the viewing window 3211, and light pipe 3229. FIG. 32C shows a side view through the treatment applicator, illustrating the control of the electrode housing 3222 by a control 3230 to adjust the position of the electrode(s) over the distal end opening of the applicator housing 3201. The two or more non-penetrating electrodes shown may be configured as cylindrical electrodes and the electrode holder (electrode housing 3222) may be surrounded by one or more agents to provide a seal. As shown in FIG. 32A, three or more openings for air (suction) are provided around the electrodes when the electrodes are deployed.

FIG. 32D shows a side view of the device of FIG. 32C with the electrode(s) moved proximally outside of the viewing window and FIG. 32E shows the front view of the viewing window 3211 with the electrode(s) moved proximally outside of the viewing window. FIG. 32F illustrate an alternative embodiment in which the control 3230 may control an internal source of suction (e.g., plunger) and the electrodes may be in a fixed position or may be controlled by a separate control.

As discussed above, the treatment applicators shown in FIGS. 26A-26D, 27A-27B, 28A-28D, 29A-29B, 30, 31A-31E, and 32A-32F all include features, including one or more of suction chambers, tissue penetrating or non-penetrating electrodes, and visualization, that may be particularly well suited for treating skin conditions such as syringoma, a benign growth of the sweat gland, which is typically arise around the eyes or on the neck, or other sensitive areas. In general, the use of the penetrating and/or non-penetrating electrodes, vacuum chamber and a viewing window as described herein may be especially beneficial for protection of such potentially sensitive areas, including around the eyes. The treatment applicators described herein may improve targeting and correct placement of even a very small (e.g., 1-3 mm) syringoma growth with the use of the viewing window while reducing or eliminating affecting nearby sensitive skin (including protecting from arcing) with the use of the vacuum chamber. This may beneficially avoid damage to the area around the eyes, for example.

In one example a region of tissue including syringoma may be treated by applying a treatment applicator (such as, for example, the treatment applicator of any of FIGS. 26A-26D, 27A-27B, 28A-28D, 29A-29B, 30, 31A-31E, and 32A-32F) against the skin so that the lesion (e.g., the syringoma) is visible within the viewing area (e.g., window) of the treatment applicator. The window into the treatment applicator may look into a suction chamber. The suction chamber may be positioned over the lesion. In some examples the suction chamber and treatment applicator may be used adjacent to the patient's eyes. Suction may then be applied to draw the tissue including the lesion, into the suction chamber. The positioning of the lesion within the chamber may be confirmed visually through the window. The tissue may be drawn into the suction chamber so that it is pulled out of the plane of the adjacent tissue by 1 mm or more (e.g., 1.5 mm or more, 2 mm or more, 3 mm or more, 4 mm or more, 5 mm or more, 6 mm or more, 7 mm or more, 8 mm or more, 9 mm or more, 1 cm or more, etc.). The tissue may be held in the suction chamber by suction while pulsed electrical energy is applied, as described herein. For example, the pulsed energy may be sub-microsecond pulsed energy, including relatively high voltage pulsed energy, such as between about 100 volts per centimeter (e.g., 0.1 kV/cm)

and about 500 kV/cm (e.g., between about 0.5 kV/cm and about 500 kV/cm, between about 1 kV/cm and about 500 kV/cm, greater than about 0.1 kV/cm, greater than about 0.5 kV/cm, greater than about 1 kV/cm, etc.). One or more treatments (e.g., train of pulses) may be applied. After application, the tissue may be released from the suction chamber. In some examples, suction may be turned off to release the tissue. In some examples, positive pressure may be applied to release the suction and therefore the tissue from the suction chamber. Optionally, the same treatment applicator may then be moved to another lesion to be treated.

For example, the apparatuses described herein may be used to treat tissue in which deployment of the electrodes and/or the application of suction at the tip may be manually and/or automatically controlled. In some examples the apparatuses described herein may include a footswitch to activate (turn on/off) vacuum, however even with the vacuum "on", suction from the tip, e.g., into a suction chamber, may be diverted by a bleed valve away from the suction chamber and/or tip; the user may apply suction at the suction chamber and/or tip by occluding the bleed valve. For convenience, the bleed valve may be present on the handle of the apparatus.

Similarly, any of these apparatuses described herein may automatically or semi-automatically deploy and/or retract the electrodes using one or more of a bias, a solenoid, or any other appropriate actuator. For example, the electrodes may be coupled to the moving shaft of the solenoid that may be controlled, e.g., by the user, to deploy the electrodes through or into the tissue when a trigger is activated.

For example, the user may initiate a vacuum by triggering a foot switch; the user may use a suction control including a bleed valve to position and reposition the treatment tip. Once the tip is placed, the bleed valve may be covered (e.g., occluded) so that suction is applied; in some examples the suction may draw the tissue into the suction chamber for treatment. For example, once the tissue is drawn into the suction chamber, the user may trigger deployment of the one or more electrodes by energizing a solenoid to drive the electrode(s) into or against the tissue. Once the treatment is complete, the solenoid may be de-energized and the microneedles may retract, e.g., manually or by triggering a solenoid or releasing a bias (e.g., spring). The user may then open the bleed valve (e.g., uncover the bleed valve opening) so that the suction in the suction chamber or tip may be released, allowing the user to remove or move the tip.

Alternatively, in some examples the user may turn on the suction so that the tissue is drawn into the suction chamber and/or tip and the user may then manually deploy, e.g., one or more spring-loaded electrode(s), such as but not limited to needle electrodes. Once the treatment is complete, the user may reset the electrode(s) into an original or storage configuration and may terminate the vacuum (e.g., by activating a foot switch).

Any of these methods, including those described above, may be used to treat various cosmetic defects, as well as seborrheic keratosis, keloids, molluscum contagiosum, sebaceous hyperplasia, congenital capillary malformation (port-wine stain), melasma, actinic keratoses, dermatosis *Papulosa nigra*, angiofibroma, skin tumors, basal cell carcinoma (BCC) and warts, instead of or in addition to syringoma.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for case of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that throughout the application, data is provided in a number of different formats, and that this data represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the disclosure. For example, the order in which various described method steps are performed may often be changed in alternative embodiments, and in other alternative embodiments one or more method steps may be skipped altogether. Optional features of various device and system embodiments may be included in some embodiments and not in others. Further, various features described in some embodiments may be included in other embodiments and combined with other features of various examples. Therefore, the foregoing description is provided primarily for exemplary purposes and should not be interpreted to limit the scope of the invention as it is set forth in the claims.

Various embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A device for delivery of electrical treatment, the device comprising:

an electrode housing extending from a distal end of the device;

a first electrode or set of electrodes on or configured to extend from a distal outer face of the electrode housing, wherein the first electrode or set of electrodes are arranged about a first length along the distal outer face of the electrode housing;

a second electrode or set of electrodes on or configured to extend from the distal outer face of the electrode housing, wherein the second electrode or set of electrodes are arranged about a second length along the distal outer face of the electrode housing that is parallel to the first length; and a suction port through the electrode housing and extending continuously along the distal outer face of the electrode housing between the first electrode or set of electrodes and the second electrode or set of electrodes, wherein the suction port extends further than the first length and the second length along the distal outer face of the electrode housing so as to prevent arcing between the first electrode or set of electrodes and the second electrode or set of electrodes.

2. The device of claim 1, wherein a strike distance, comprising a minimum path length between the first electrode or set of electrodes and the second electrode or set of electrodes around the suction port, is 5% or more longer than a minimum distance between the first electrode or sets of electrodes and the second electrode or set of electrodes extending across the suction port.

3. The device of claim 1, wherein a strike distance, comprising a minimum path length between the first electrode or set of electrodes and the second electrode or set of electrodes and around the suction port, is 10% or more longer than a minimum distance between the first electrode or sets of electrodes and the second electrode or set of electrodes extending across the suction port.

4. The device of claim 1, wherein the suction port at least partially surrounds the first electrode or set of electrodes.

5. The device of claim 1, further comprising a second suction port through the electrode housing and extending continuously between the first electrode or set of electrodes and the second electrode or set of electrodes.

6. The device of claim 1, further comprising a first outer suction port arranged along the distal outer face on a side of the first electrode or set of electrodes opposite from the suction port, and a second outer suction port arranged along the distal outer face on a side of the second electrode or set of electrodes opposite from the suction port.

7. The device of claim 1, wherein the suction port comprises a C-shaped opening through the distal outer face of the electrode housing.

8. The device of claim 1, wherein the suction port comprises an I-shaped opening through the distal outer face of the electrode housing.

9. The device of claim 1, wherein the electrode housing is configured to extend and retract relative to the distal end of the device.

10. The device of claim 1, wherein the first electrode or set of electrodes and the second electrode or set of electrodes comprise non-penetrating electrodes.

11. The device of claim 1, wherein the first electrode or set of electrodes and the second electrode or set of electrodes comprise tissue penetrating electrodes.

12. The device of claim 1, further comprising one or more circumferential seals around the suction port and configured to seal the distal end of the device against a target tissue when suction is applied through the suction port.

13. The device of claim 1, further comprising a suction channel within the electrode housing in fluid communication with the suction port.

14. The device of claim 1, wherein the device is configured as a treatment tip, further wherein the device comprises a mechanical and/or electrical connector at a proximal end of the treatment tip configured to removably couple to a handpiece.

15. The device of claim 1, wherein the device comprises a reusable handpiece and a replaceable treatment tip, wherein the replaceable treatment tip is configured to releasably couple to the reusable handpiece through one or more electrical connectors and a vacuum connector.

16. The device of claim 15, further comprising a pulse generator configured to couple to the reusable handpiece and a source of negative pressure within the reusable handpiece.

17. A method, the method comprising:

applying a distal end of a treatment applicator against a tissue;

contacting the tissue with a first electrode or first set of electrodes positioned about a first length along a distal outer face of an electrode housing and a second electrode or second set of electrodes positioned about a second length along the distal outer face of the electrode housing of the treatment applicator;

preventing arcing between the first electrode or first set of electrodes and the second electrode or second set of electrodes by applying suction through a suction port extending continuously along the distal outer face between the first electrode or first set of electrodes and the second electrode or second set of electrodes and longer than the first length and the second length so that the tissue contacts the suction port between and extending beyond on either side of the first electrode or first set of electrodes and the second electrode or second set of electrodes; and applying a pulsed electrical treatment to the tissue from the first electrode or first set of electrodes and the second electrode or second set of electrodes.

18. The method of claim 17, wherein preventing arcing comprises applying suction through the suction port configured such that a minimum path length between the first electrode or first set of electrodes and the second electrode or second set of electrodes around the suction port is 5% or more longer than a minimum distance between the first electrode or first sets of electrodes and the second electrode or second set of electrodes that extends across the suction port.

19. The method of claim 17, wherein contacting the tissue comprises penetrating the tissue with the first electrode or first set of electrodes and the second electrode or second set of electrodes.

20. The method of claim 17, wherein contacting the tissue comprises applying the first electrode or first set of electrodes and the second electrode or second set of electrodes to the tissue without penetrating the tissue.

21. The method of claim 17, wherein contacting the tissue comprises driving the distal end of the treatment applicator against the tissue to retract the electrode housing into an applicator housing of the treatment applicator against a housing bias force.

22. The method of claim 17, further comprising sealing the distal end of the treatment applicator against the tissue.

23. The method of claim 17, further comprising coupling a treatment tip to a reusable handpiece to assemble the treatment applicator before applying the distal end of the treatment applicator against the tissue.

24. A device for delivery of electrical treatment, the device comprising:

a first electrode or set of electrodes on or configured to extend from a tip portion of the device, wherein the first electrode or set of electrodes have a first length configured to be in contact with tissue when the tip portion of the device is positioned for electrical treatment;

a second electrode or set of electrodes on or configured to extend from the tip portion of the device, wherein the second electrode or set of electrodes have a different polarity from the first electrode or set of electrodes; and a suction barrier extending continuously along and further than the first length and partially or fully surrounding the first electrode or set of electrodes so as to increase a strike distance between electrodes of different polarity and prevent arcing between the first electrode or set of electrodes and the second electrode or set of electrodes.

25. The device of claim 24, wherein the second electrode or set of electrodes have a second length configured to be in contact with tissue when the tip portion of the device is positioned for tissue treatment.

26. The device of claim 25, wherein the second length is parallel to the first length.

27. The device of claim 25, further comprising a second suction barrier extending continuously along the second length and partially or fully surrounding the second electrode or set of electrodes.

28. The device of claim 24, wherein the suction barrier comprises one or more suction ports positioned adjacent to and separating the first electrode or the set of electrodes from the second electrode or the sets of electrodes.

29. The device of claim 27, wherein the suction barrier and/or the second suction barrier has a C-shaped opening.

30. The device of claim 24, the device comprising a distal end angled relative to a long axis of the device.

31. The device of claim 24, wherein the device is configured to reduce arcing between the first electrode or set of electrodes and the second electrode or set of electrodes when operating at high voltages of 1kV/cm or more.

32. The device of claim 24, wherein the first electrode or set of electrodes and the second electrode or set of electrodes comprise non-penetrating electrodes.

33. The device of claim 24, further comprising a suction connector configured to couple with a source of negative pressure.

34. The device of claim 24, wherein the strike distance, comprising a shortest path between the first electrode or set of electrodes and the second electrode or set of electrodes that goes around the suction barrier, is 5% or more longer than a minimum distance between the first electrode or set of electrodes and the second electrode or set of electrodes extending across and ignoring the suction barrier.

\* \* \* \* \*